United States Patent
Weber

(10) Patent No.: US 11,198,139 B2
(45) Date of Patent: Dec. 14, 2021

(54) ANALYTE DETECTION METHODS AND APPARATUS USING DIELECTROPHORESIS AND ELECTROOSMOSIS

(71) Applicant: Fluid-Screen, Inc., Beverly, MA (US)

(72) Inventor: Monika Weber, Fredericksburg, VA (US)

(73) Assignee: Fluid-Screen, Inc., Beverly, MA (US)

( * ) Notice: Subject to any disclaimer, the term of this patent is extended or adjusted under 35 U.S.C. 154(b) by 0 days.

(21) Appl. No.: 16/093,883

(22) PCT Filed: Apr. 14, 2017

(86) PCT No.: PCT/US2017/027659
§ 371 (c)(1),
(2) Date: Oct. 15, 2018

(87) PCT Pub. No.: WO2017/181030
PCT Pub. Date: Oct. 19, 2017

(65) Prior Publication Data
US 2020/0179947 A1    Jun. 11, 2020

Related U.S. Application Data

(60) Provisional application No. 62/326,665, filed on Apr. 22, 2016, provisional application No. 62/323,549, filed on Apr. 15, 2016.

(51) Int. Cl.
*B01L 3/00* (2006.01)
*G01N 15/10* (2006.01)
(Continued)

(52) U.S. Cl.
CPC ........ *B03C 5/005* (2013.01); *B01L 3/502753* (2013.01); *B01L 3/502761* (2013.01);
(Continued)

(58) Field of Classification Search
CPC ..... B01L 2400/0421; B01L 2400/0424; B01L 2400/0418; B01L 2200/0652; B03C 5/00;
(Continued)

(56) References Cited

U.S. PATENT DOCUMENTS 4,970,154 A    11/1990  Chang
5,622,588 A    4/1997   Weber
(Continued)

FOREIGN PATENT DOCUMENTS

WO    WO 2012/048230 A2    4/2012

OTHER PUBLICATIONS

U.S. Appl. No. 14/582,525, filed Dec. 24, 2014, Weber et al.
(Continued)

*Primary Examiner* — Gurpreet Kaur
(74) *Attorney, Agent, or Firm* — Wolf, Greenfield & Sacks, P.C.

(57) ABSTRACT

Methods and apparatus for detection and/or identification of analytes including bacteria using dielectrophoresis and electroosmotic traps. Switching between different frequencies of an applied electric field results in movement of the analyte between dielectrophoresis and electroosmotic trapping states. The use of edge-based sensing techniques enables the use of electrodes with a larger form factor than nanowire sensors. Signal modulation based on analyte contact with the electrode edge is also described.

19 Claims, 72 Drawing Sheets

(51) Int. Cl.
*B03C 5/00* (2006.01)
*B03C 5/02* (2006.01)

(52) U.S. Cl.
CPC ......... *B03C 5/026* (2013.01); *G01N 15/1031* (2013.01); *B01L 2400/0418* (2013.01); *B01L 2400/0424* (2013.01)

(58) Field of Classification Search
CPC ......... B03C 5/005; B03C 5/022; B03C 5/024; B03C 5/026; F04F 1/00; B01D 61/427
See application file for complete search history.

(56) References Cited

U.S. PATENT DOCUMENTS

| | | | |
|---|---|---|---|
| 5,814,200 | A | 9/1998 | Pethig et al. |
| 6,071,394 | A | 6/2000 | Cheng et al. |
| 6,264,815 | B1 | 7/2001 | Pethig et al. |
| 6,280,590 | B1 | 8/2001 | Cheng et al. |
| 6,576,459 | B2 | 6/2003 | Miles et al. |
| 6,875,329 | B2 | 4/2005 | Washizu et al. |
| 6,887,362 | B2 | 5/2005 | Huang et al. |
| 6,989,086 | B2 | 1/2006 | Cheng et al. |
| 7,081,192 | B1 | 7/2006 | Wang et al. |
| 7,115,422 | B1 * | 10/2006 | Gilton ............... G01N 1/40 436/178 |
| 7,153,648 | B2 | 12/2006 | Jing et al. |
| 7,169,282 | B2 | 1/2007 | Talary et al. |
| 7,198,702 | B1 | 4/2007 | Washizu et al. |
| 7,384,791 | B2 | 6/2008 | Tyvoll et al. |
| 7,390,387 | B2 | 6/2008 | Childers et al. |
| 7,390,388 | B2 | 6/2008 | Childers et al. |
| 7,470,533 | B2 | 12/2008 | Xu et al. |
| 7,534,334 | B1 | 5/2009 | Fiechtner et al. |
| 7,615,762 | B2 | 11/2009 | Satyanarayana et al. |
| 7,658,829 | B2 | 2/2010 | Kanagasabapathi et al. |
| 7,666,289 | B2 | 2/2010 | Simmons et al. |
| 7,686,934 | B2 | 3/2010 | Hodko et al. |
| 7,744,738 | B1 | 6/2010 | Gagnon et al. |
| 8,029,657 | B1 | 10/2011 | Wu |
| 9,120,105 | B2 | 9/2015 | Weber et al. |
| 2002/0036142 | A1 | 3/2002 | Gascoyne et al. |
| 2003/0022393 | A1 | 1/2003 | Seul et al. |
| 2003/0146100 | A1 | 8/2003 | Huang et al. |
| 2004/0011651 | A1 | 1/2004 | Becker et al. |
| 2004/0077074 | A1 | 4/2004 | Ackley et al. |
| 2004/0109793 | A1 | 6/2004 | McNeely et al. |
| 2004/0226819 | A1 | 11/2004 | Talary et al. |
| 2005/0112544 | A1 | 5/2005 | Xu et al. |
| 2005/0158704 | A1 | 7/2005 | Tyvoll et al. |
| 2006/0226012 | A1 | 10/2006 | Kanagasabapathi et al. |
| 2007/0125650 | A1 | 6/2007 | Scurati et al. |
| 2008/0105565 | A1 | 5/2008 | Davalos et al. |
| 2008/0134792 | A1 | 6/2008 | Lee et al. |
| 2008/0221806 | A1 | 9/2008 | Bryant et al. |
| 2009/0020428 | A1 | 1/2009 | Levitan et al. |
| 2009/0294291 | A1 | 12/2009 | Voidman et al. |
| 2009/0304644 | A1 | 12/2009 | Hedrick et al. |
| 2010/0219075 | A1 | 9/2010 | Furusawa |
| 2010/0297608 | A1 | 11/2010 | Stern et al. |
| 2011/0123979 | A1 | 5/2011 | Salmon et al. |
| 2011/0147917 | A1 | 6/2011 | England et al. |
| 2012/0088295 | A1 | 4/2012 | Yasuda et al. |
| 2013/0105317 | A1 | 5/2013 | Weber et al. |
| 2013/0118904 | A1 | 5/2013 | Dickerson et al. |
| 2013/0292247 | A1 * | 11/2013 | Peyrade ............... B03C 5/005 204/518 |
| 2014/0083855 | A1 | 3/2014 | Cheng et al. |
| 2014/0166483 | A1 | 6/2014 | Chow et al. |
| 2015/0107999 | A1 * | 4/2015 | Weber ............... B01L 3/502753 204/603 |
| 2015/0283553 | A1 * | 10/2015 | Chariot ............... B03C 5/026 204/547 |
| 2015/0318161 | A1 | 11/2015 | Brown et al. |
| 2016/0339423 | A1 | 11/2016 | Quake et al. |
| 2017/0028408 | A1 | 2/2017 | Menachery et al. |
| 2018/0080020 | A1 | 3/2018 | Link et al. |
| 2018/0106759 | A1 * | 4/2018 | de Oliveira Botelho ............... G01N 21/27 |
| 2021/0039098 | A1 | 2/2021 | Weber et al. |
| 2021/0039099 | A1 | 2/2021 | Weber et al. |

OTHER PUBLICATIONS

EP 15874123.1, Aug. 27, 2018, Extended European Search Report.
PCT/US2017/027659, Feb. 12, 2018, International Search Report and Written Opinion.
PCT/US2015/65229, Feb. 16, 2016, International Search Report and Written Opinion.
PCT/US2015/65229, Jul. 6, 2017, International Preliminary Report on Patentability.
Extended European Search Report for European Application No. 15874123.1 dated Aug. 27, 2018.
International Search Report and Written Opinion for International Application No. PCT/US2017/027659 dated Feb. 12, 2018.
International Search Report and Written Opinion for International Application No. PCT/US2015/65229 dated Feb. 16, 2016.
International Preliminary Report on Patentability for International Application No. PCT/US2015/065229 dated Jul. 6, 2017.
Beving et al., Dielectric Properties Of Human Blood And Erythrocytes at Radio Frequencies (0.2-10 MHz); Dependence On Cell Volume Fraction and Medium Composition. Eur Biophys J. 1994;23:207-15.
Carstensen, Passive Electrical Properties Of Microorganisms. Biophysical Journal. 1967;7:493-503.
Chang et al., A Continuous Size-Dependent Particle Separator Using A Negative Dielectrophoretic Virtual Pillar Array †. Lab Chip. 2008;8:1930-6.
Cheng et al., An Integrated Dielectrophoretic Chip for Continuous Bioparticle Filtering, Focusing, Sorting, Trapping, and Detecting. Biomicrofluidics. 1, 021503. 2007. 15 pages.
Cho et al., Creating, Transporting, Cutting, and Merging Liquid Droplets by Electrowetting-Based Actuation for Digital Microfluidic Circuits. Journal of Microelectromechanical Systems. 2003;12(1):70-80.
Choi et al., 3-Dimensional Electrode Patterning Within A Micro fluidic Channel Using Metal ION Implantation. Lab Chip. 2010;10(6):783-8.
Cociancich et al., Insect Defensin, an Inducible Antibacterial Peptide, Forms Voltage-Dependent Channels In Micrococcus Luteus* The Journal Of Biological Chemistry. 1993;268(26);19239-45.
Fritz, Anomalous Diffusion of Erythocytes in the Presence of Polyvinylpyrrolidone. Biophys. J. Society. 1984;46:219-228.
Huang et al., Differences In The AC Electrodynamics Of Viable And Non-Viable Yeast Cells Determined Through Combined Dielectrophoresis And Electrorotation Studies. Phys. Med. Biol. 1992;37(7):1499-517.
Kuczenski et al., Dielectrophoretic Microfluidic Device for the Continuous Sorting of *Escherichia coli* From Blood Cells. Biomicrofluidics. 2011;5:032005. 16 pages.
Lee et al., Electrowetting and Electrowetting-On-Dielectric for Microscale Liquid Handling. Sensors And Actuators A. 95. 2002:259-68.
Markx et al., Dielectrophoretic Characterization and Separation of Micro-Organisms. Microbiology. 1994;140:585-91.
Pethig, Review Article-Dielectrophoresis: Status of the Theory, Technology, and Applications. Biomicrofluidics. 2010;4:022811. 36 pages.
Pohl et al., The Continuous Positive and Negative Dielectrophoresis of Microorganisms. Forum Press, Inc. J. Biol. Phys. 1981;9:67-86.
Pohl, Separation Of Living And Dead Cells By Dielectrophoresis. Science. 1968;152:647-9.
Pollack et al., Electrowetting-Based Actuation of Liquid Droplets for Microfluidic Applications. Appl. Phys. Lett. 2000;77(11):1725-6.
Pollack et al., Electrowetting-Based Actuation of Droplets for Integrated Microftuidics. Lab Chip. 2002;2:96-101.

(56) References Cited

OTHER PUBLICATIONS

Printen et al., Membrane Changes In Lipopolysaccharide-Stimulaled Murine B Lymphocytes Associated With Cell Activation. Biochimica et Biophysica Acta. 1993;1148:91-96.
Shah et al., Specific binding and magnetic concentration of CD8+ T-lymphocytes on electrowetting-on-dielectric platform. Biomicrofluidics. 2010;4:044106. 13 pages.
Sher, Dielectrophoresis in Lossy Dielectric Media. Nature. 1968;220:695-6.
Stern et al., Label-free biomarker detection from whole blood. Nature Nanotechnology. 2010;5:138-42.
Stern et al., Label-free Electronic Detection of the Antigen-Specific T-Cell Immune Response. Nano Lett. 2008;8(10):3310-4.
Surowiect et al., Dielectric Properties Of Human B And T Lymphocytes Al Frequencies From 20 kHz To 100 MHz. Phys. Med. Biol. 1986;31(1):43-53.
Unni et al., Characterization and Separation of Cryptosporidium and Giardia Cells Using On-Chip Dielectrophoresis. Biomicrofluidics 6, 012805. 2012. 25 pages.
Urdaneta et al., Multiple frequency dielectrophoresis. Electrophoresis. 2007;28:3145-55.
Vacic et al., Multiplexed SOI BioFETs. Biosens. Bioelectron. 2011;28:239-42.
Vahey et al., High-Throughput Cell and Particle Characterization Using Isodielectric Separation. Anal. Chemistry. 2009;81(7):2446-55.
Voldman, Electrical Forces for Microscale Cell Manipulation. Annual Review of Biomedical Engineering. 2006;8:425-54.
Xie et al., A three-phased circular electrode array for electro-osmotic microfluidic pumping. Microsyst Technol. 2011;17:367-72.
Yang et al., Dielectric Properties of Human Leukocyte Subpopulations Determined By Electrorotation as a Cell Separation Criterion. Biophysical Journal. 1999;76:3307-14.
Yang et al., Differential Analysis Of Human Leukocytes By Dielectrophoretic Field-Flow-Fractionation. Biophysical Journal. 2000;78:2680-89.
Extended European Search Report for European Application No. 17783251.6 dated Oct. 24, 2019.
International Preliminary Report on Patentability for International Application No. PCT/US2017/027659 dated Oct. 25, 2018.
Ho et al., Rapid heterogeneous liver-cell on-chip patterning via the enhanced field-induced dielectrophoresis trap. Lab on a Chip. 2006;6:724-734. doi: 10.1039/b602036d.
Wu, Biased AC Electro-Osmosis for On-Chip Bioparticle Processing. IEEE Transactions on Nanotechnology. 2006;5(2):84-89.
Invitation to Pay Additional Fees dated Jan. 25, 2021 in connection with International Application No. PCT/US2020/060412.
Invitation to Pay Additional Fees dated Feb. 17, 2021 in connection with International Application No. PCT/US2020/060147.
International Search Report and Written Opinion dated Apr. 12, 2021 in connection with International Application No. PCT/US2020/060412.
International Search Report and Written Opinion dated Apr. 22, 2021 in connection with International Application No. PCT/US2020/060147.
Green et al., Manipulation and trapping of sub-micron bioparticles using dielectrophoresis. Journal of Biochemical and Biophysical Methods. Sep. 25, 1997;35(2):89-102.
Kim et al., Multitarget dielectrophoresis activated cell sorter. Analytical Chemistry. Nov. 15, 2008;80(22):8656-61. [NIH Public Access Author Manuscript].
Extended European Search Report dated Oct. 19, 2021 in connection with European Application No. 20205400.3.

\* cited by examiner

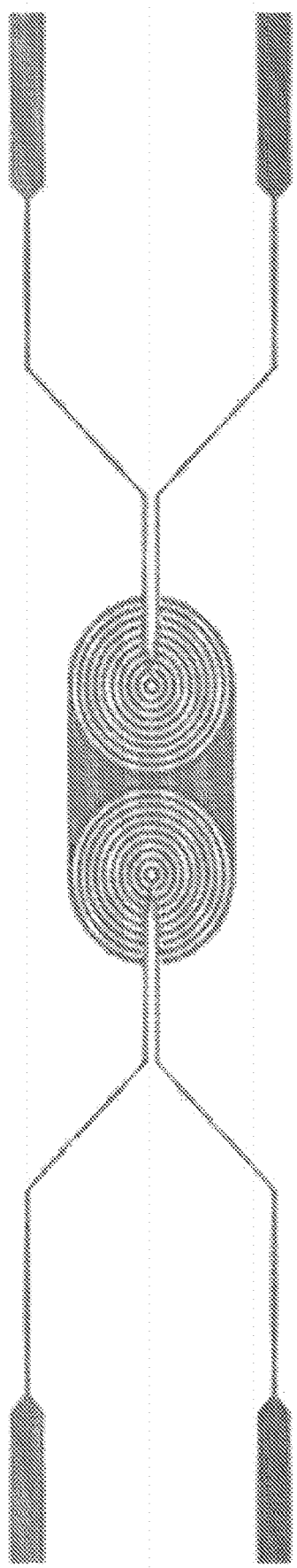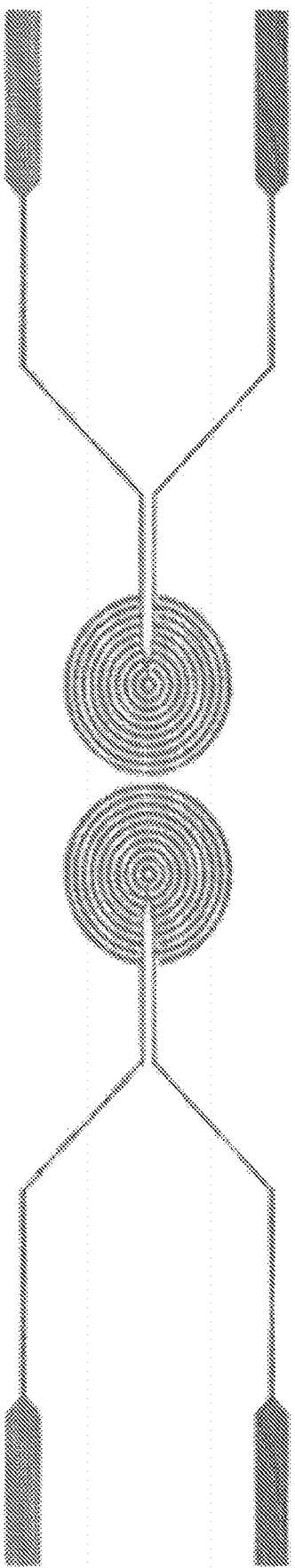

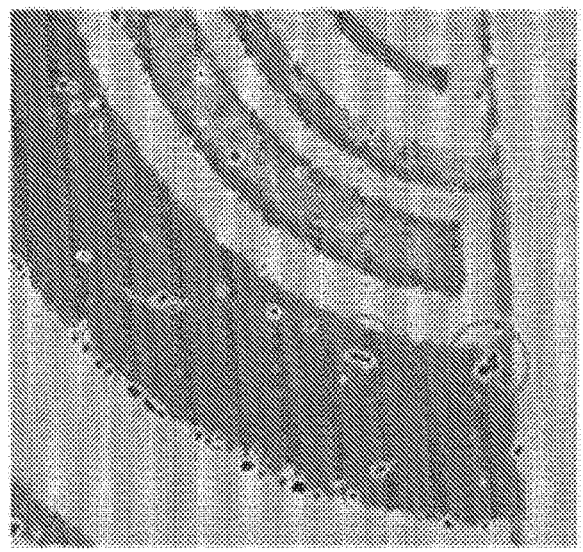
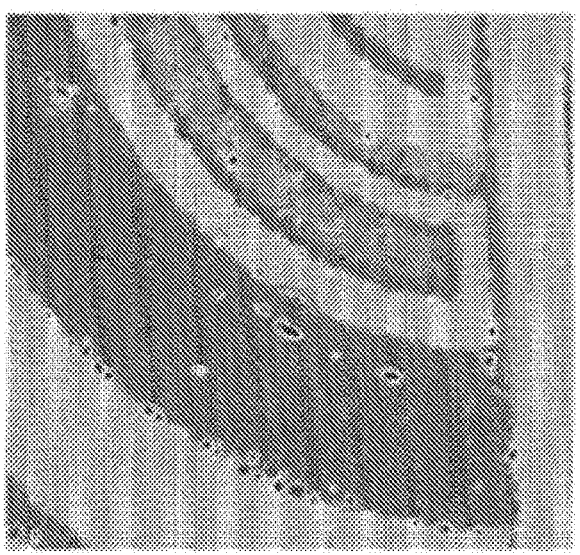
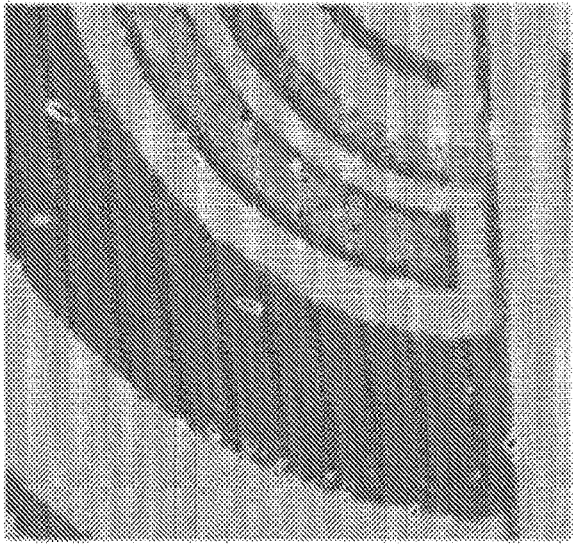
FIG. 17A
FIG. 17B
FIG. 17C

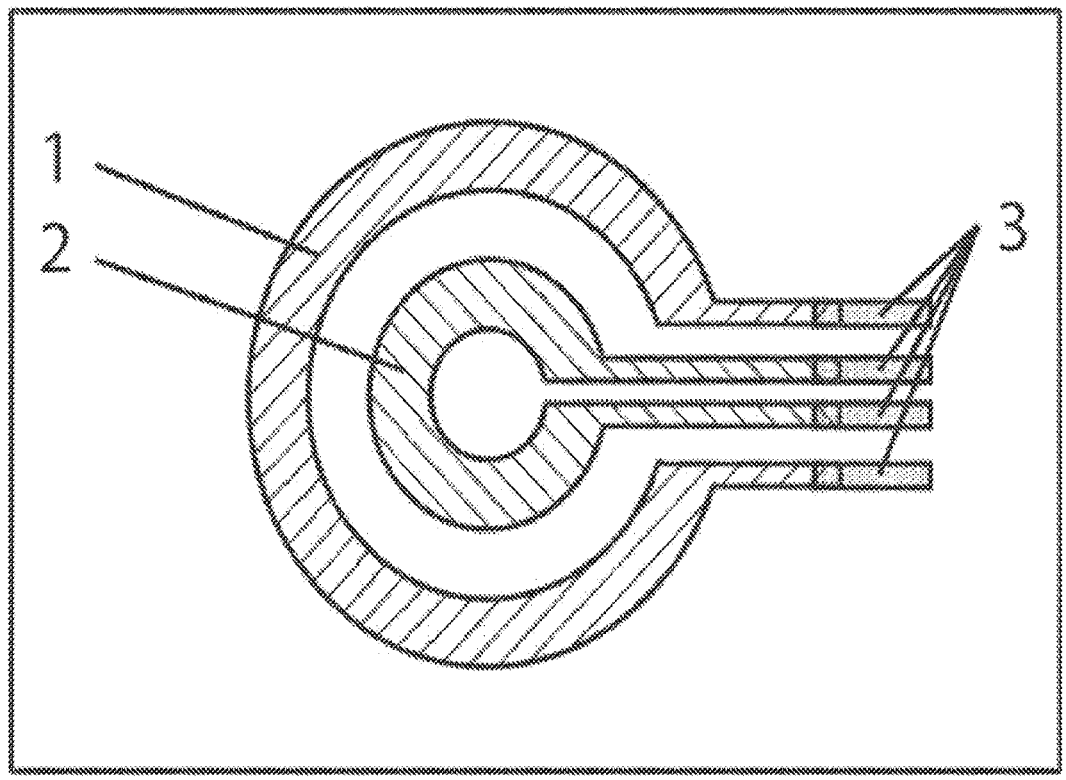
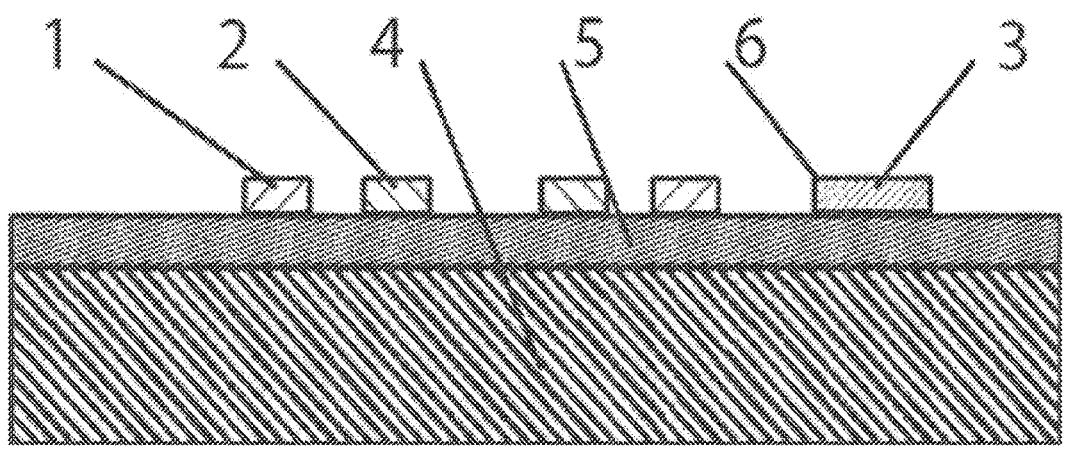
FIG. 37

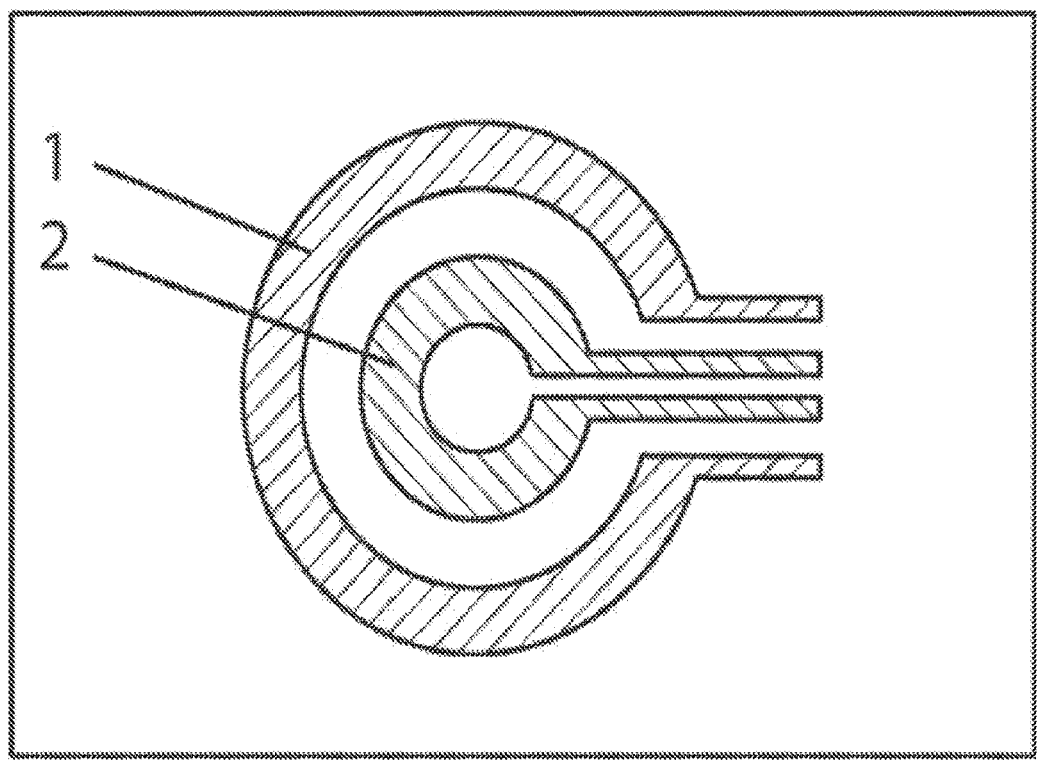
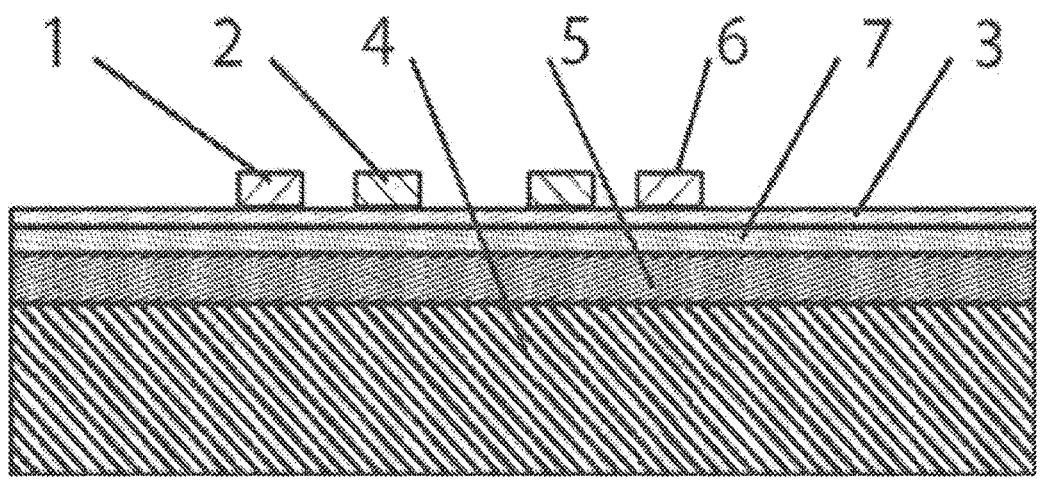
FIG. 38

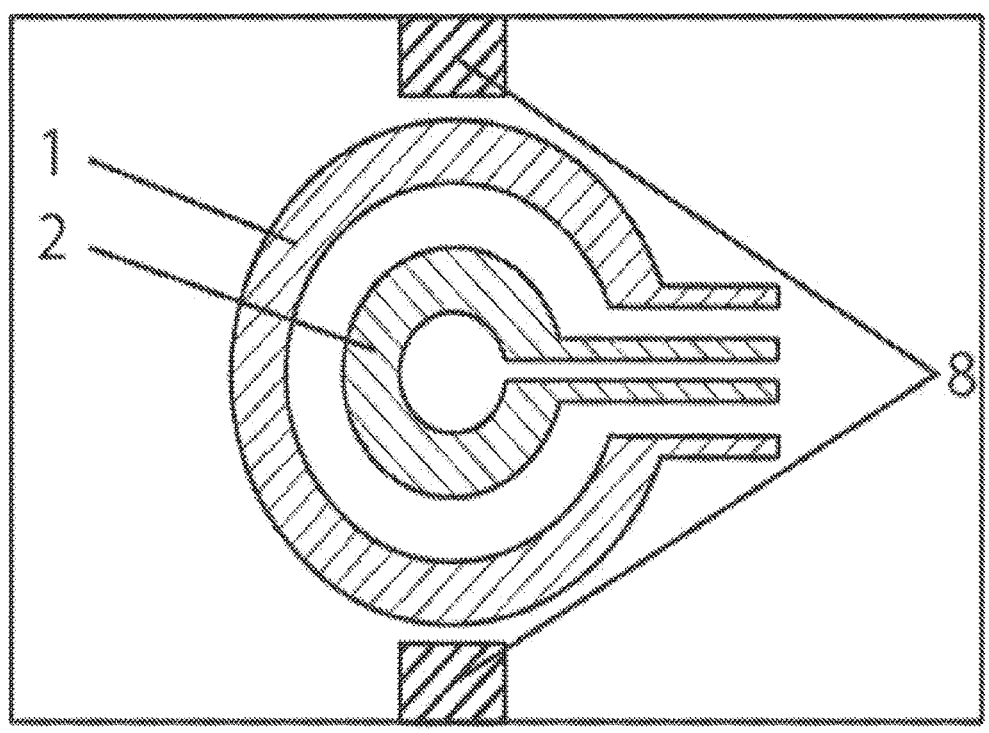
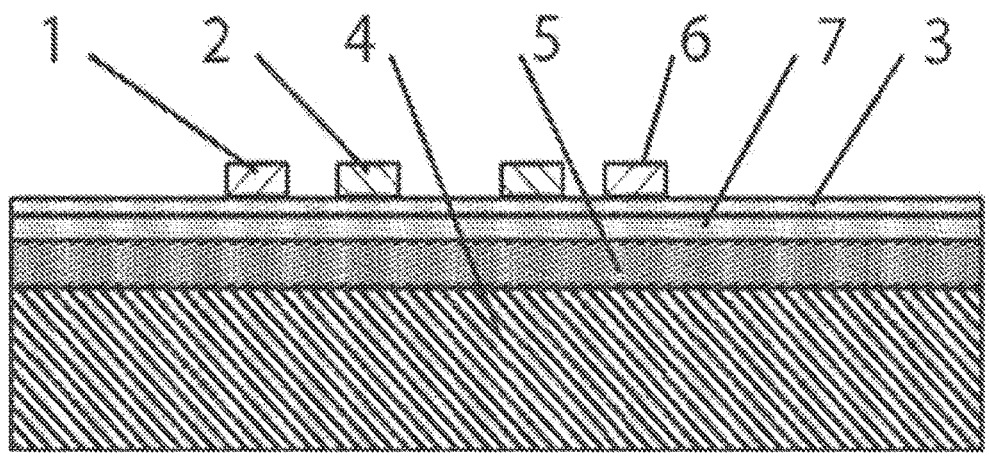
FIG. 41

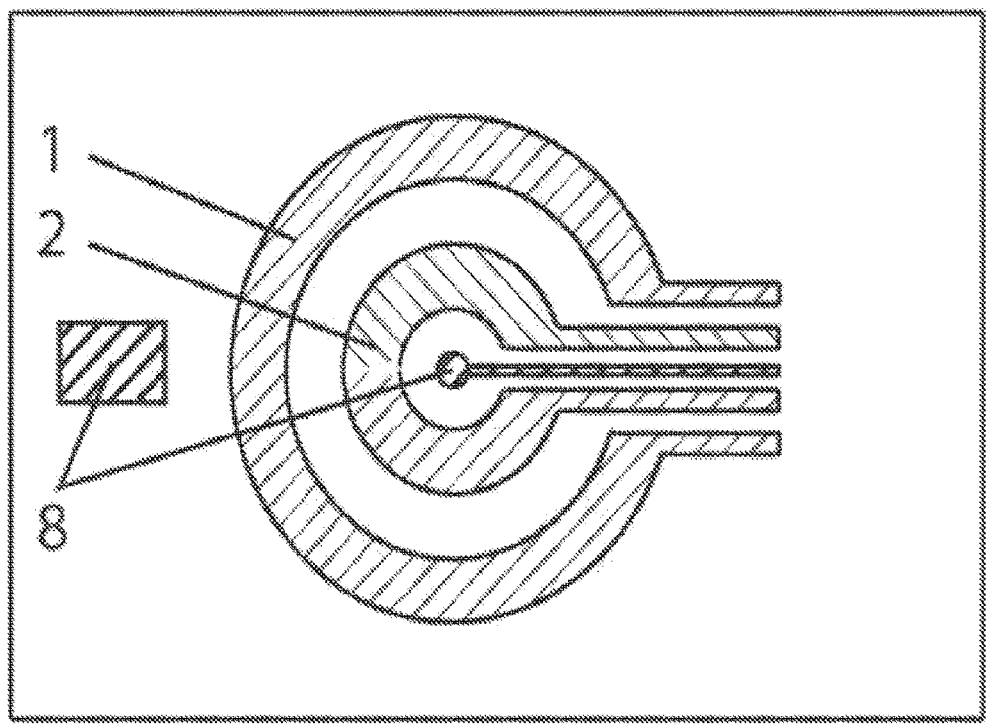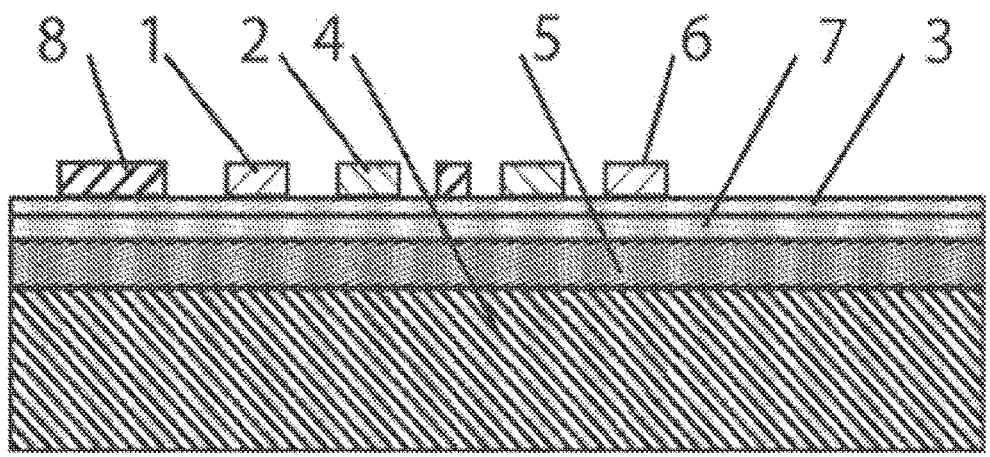
FIG. 42

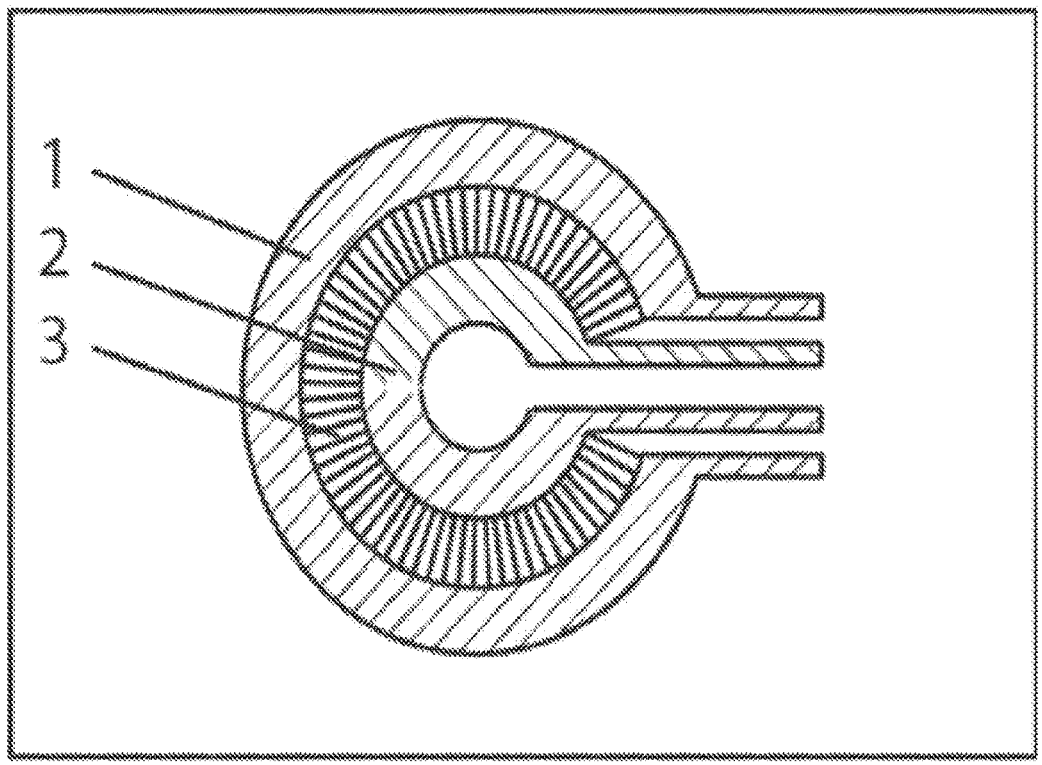
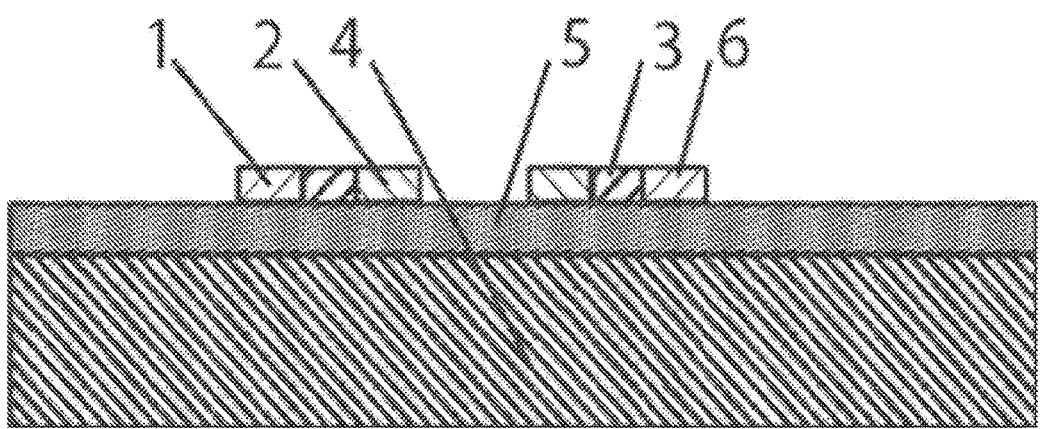
FIG. 43

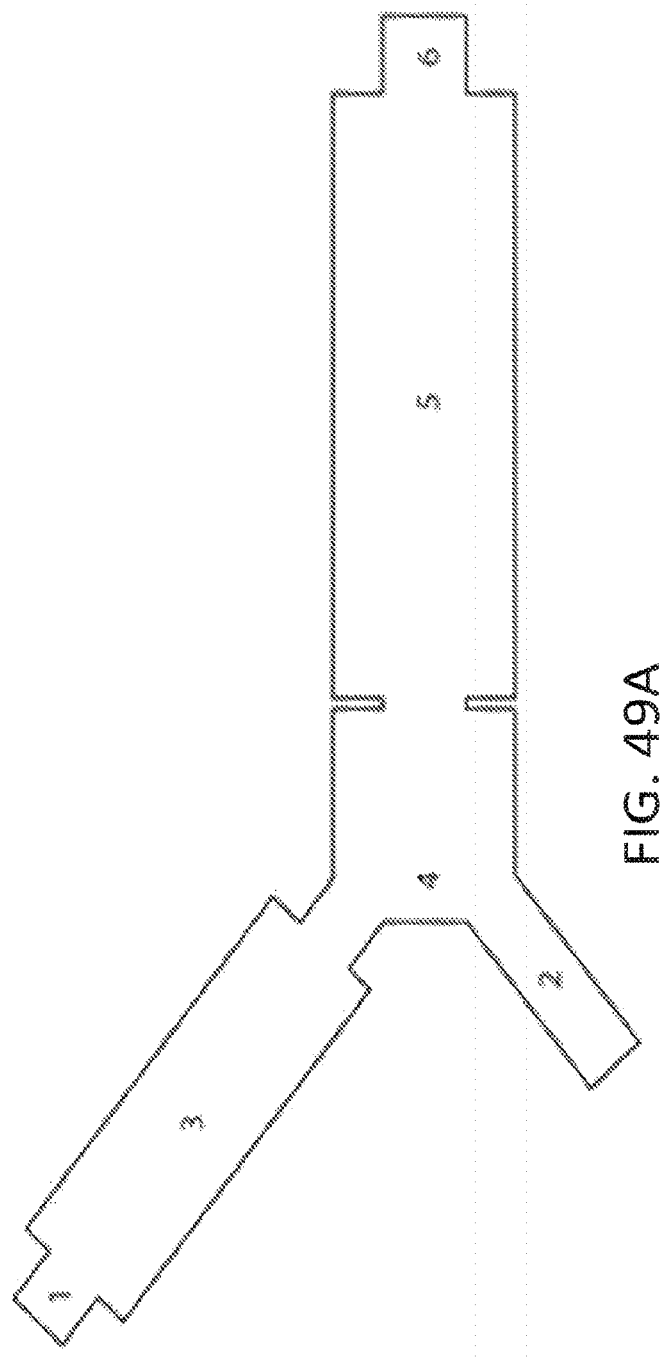

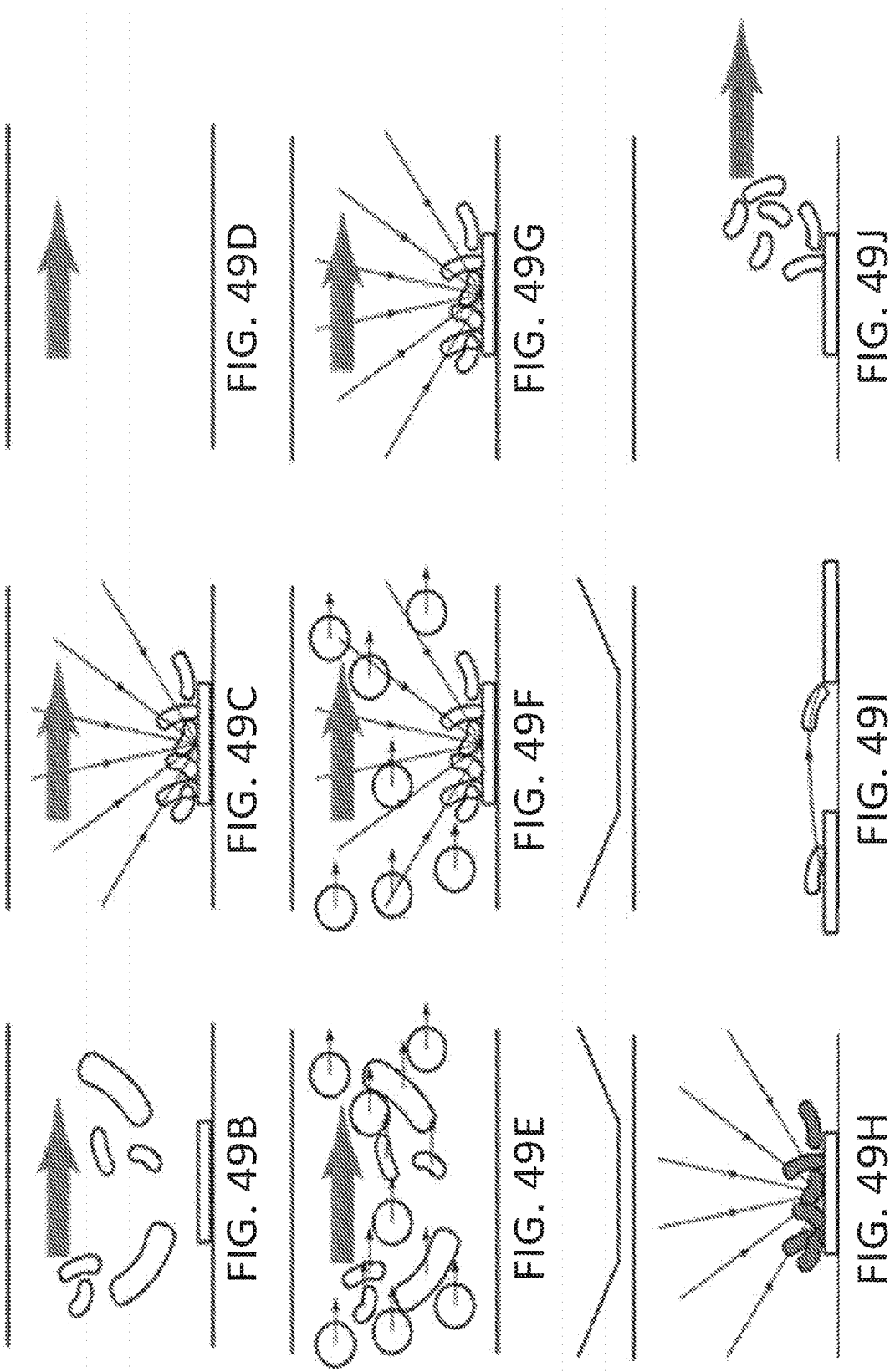

ANALYTE DETECTION METHODS AND APPARATUS USING DIELECTROPHORESIS AND ELECTROOSMOSIS

CROSS REFERENCE TO RELATED APPLICATIONS

This Application is a national stage filing under 35 U.S.C. § 371 of International Patent Application No. PCT/US2017/027659, filed Apr. 14, 2017, which was published under PCT Article 21(2) in English and claims the benefit under 35 USC § 119(e) of U.S. Provisional Application Ser. No. 62/326,665, filed Apr. 22, 2016, and U.S. Provisional Application Ser. No. 62/323,549, filed Apr. 15, 2016, each of which is herein incorporated herein by reference in its entirety.

BACKGROUND

This disclosure relates to the fields of microfluidics, AC kinetics and dielectrophoresis, for purposes of bacteria, viruses or other microscale component capture, separation, detection, identification and filtration.

Detection of even a few microorganisms or biomarkers in cerebrospinal fluid (CSF) by a standardized protocol is a critical matter for diagnosis of such diseases including Alzheimer's disease, multiple sclerosis (MS) as well as bacterial and viral infections or contamination.

Detection and identification of bacterial and viral pathogens present in cell containing solutions (e.g., blood, urine, CSF), protein containing solutions (e.g., for quality control in pharmaceuticals during manufacturing), analyte extraction from microbiome samples, water, sterile fluids and other fluids is possible by employing isolation on cultural media and metabolic fingerprinting methods. Isozome analysis, direct colony thin layer chromatography and gel electrophoresis techniques have been successfully applied for the detection of some bacterial pathogens. Immunoassay and nucleic acid-based assays are now widely accepted techniques, providing more sensitive and specific detection and quantification of bacterial pathogens affecting a wide range of host plant species. Polymerase Chain Reaction (PCR) is used for pathogens that are difficult to culture.

SUMMARY

Existing techniques for capture, separation, filtration, detection and/or identification of microorganisms (e.g., bacteria, viruses) or other microscale components (collectively referred to herein as "analytes") in solution lack broad applicability. For example, techniques for bacterial or viral pathogen isolation on cultural media and metabolic fingerprinting are labor- and time-intensive, and results often are inconclusive; molecular techniques such as isozome analysis cannot discriminate living cells from dead cells; and the application of PCR to clinical specimens has many potential pitfalls due to the susceptibility of PCR to inhibitions and contamination. It is known for instance that the sensitivity and specificity of a PCR assay is dependent on target genes, primer sequences, PCR techniques, DNA extraction procedures, and PCR product detection methods.

Since PCR is based on DNA amplification, false positive and false negative outcomes often occur. Carryover contamination of reagents, pipetting devices, laboratory surfaces, or even the skin of workers can yield false-positive results, for example.

Separation of various confounding elements such as red blood cells, white blood cells, other types of cells or microscopic fluid components and dead bacteria presents a challenge to current detection systems, which often rely on such separation for correct operation. Close to real-time separation of low levels of bacteria or viruses from complex sample matrices such as environmental water, protein and cell matrices (e.g., drugs made in bioreactors), body fluids, patient samples, e.g., blood, microbiome, has not been achieved yet.

Some embodiments are directed to a spectrometer configured to determine an identity of analyte particles in solution. The spectrometer comprises a circular-shaped or partially-center-symmetric electrode configured to be placed in an AC electric field; a controller configured to switch at least one property of the AC electric field from a first condition to a second condition, wherein when the AC electric field is in the first condition, the analyte particles are trapped in a first AC kinetic trap on the electrode and wherein when the AC electric field is in the second condition, the analyte particles trapped in a second AC kinetic trap on the electrode; a detector configured to determine at least one motion characteristic of the analyte particles from the first AC kinetic trap to the second AC kinetic trap in response to switching the at least one property of the AC electric field; and at least one processor programmed to determine an identity of the analyte particles based, at least in part, on the determined at least one motion characteristic.

Some embodiments are directed to a method of determining an identity of analyte particles in a solution. The method comprises placing a spiral-shaped or partially-center symmetric electrode in an AC electric field; switching at least one property of the AC electric field from a first condition to a second condition, wherein when the AC electric field is in the first condition, the analyte particles are trapped in a first AC kinetic trap on the electrode and wherein when the AC electric field is in the second condition, the analyte particles trapped in a second AC kinetic trap on the electrode; determining at least one motion characteristic of the analyte particles from the first AC kinetic trap to the second AC kinetic trap in response to switching the at least one property of the AC electric field; and determining an identity of the analyte particles based, at least in part, on the determined at least one motion characteristic.

Some embodiments are directed to an apparatus, comprising at least one electrode configured to be placed in an AC electric field; and a controller configured to control at least one characteristic of the AC electric field to identify, based on dynamics of induced motion, analyte particles in a solution located adjacent to the at least one electrode.

Some embodiments are directed to in a microfluidic device including a microfluidic chamber adapted for filtering and analyzing analytes from entities to be eliminated from analysis, said device comprising dielectrophoresis (DEP) and/or electroosmosis (EO) electrodes, a method for highly selective filtration. The method comprises compiling data including a Clausius-Mossotti (CM) factor as a function of frequency and conductivity for said analytes and said entities to be eliminated; for each entity to be eliminated, identifying, based on the data, a frequency and conductivity having a largest difference for said CM factor for said analyte and said CM factor for said entity to be eliminated; filtering said entity to be eliminated by introducing a solution of the identified conductivity and by imposing an electric field of the identified frequency so as to separate said entity to be eliminated; wherein separation for each entity to be eliminated is used to achieve said highly selective filtration.

Some embodiments are directed to a device for capture, separation, and/or filtering of analytes in a fluid sample containing said analytes and entities to be eliminated. The device comprises a pump configured to force said fluid sample past a dielectrophoresis (DEP) filter or an electroosmosis (EO) filter, said filter comprising electrodes adapted to produce a force or motion on said analytes that is different than the force on said entities to be eliminated; a concentrating electrode adapted to attract said analytes after filtration and hold them while said pump replaces said solution with a buffer solution; a microwire field effect transistor (FET) comprising a source, a drain, and a microwire connecting the source and the drain, wherein the source, the drain, and the microwire are disposed on an insulating substrate formed on a semiconducting bottom gate layer; and secondary electrodes arranged adjacent to said microwire FET and being adapted to attract said analytes to contact said microwire.

Some embodiments are directed to a method for selective functionalization of a microwire field effect transistor (FET) array, wherein each FET in the microwire FET array includes a source, a drain, and a microwire connecting the source and the drain. The method comprises (a) coating said microwire FET array with a passivating layer; (b) applying an electric field of sufficient intensity to sources and drains of a subset of the FETs in said FET array so as to overcome a breakdown voltage of said passivating layer, thereby removing said passivating layer from said subset of said FET array; (c) introducing a solution containing a functionalizing element onto said microwire FET array, allowing said solution to contact the microwires of the FETs in said subset while all microwires of the FETs not in said subset remain protected by said passivating layer, and flushing said solution; and (d) repeating acts (b) and (c) for each subset of FETs in said FET array requiring a different functional layer; wherein a set of differently functionalized FET microwires are obtained without requiring micropositioning.

Some embodiments are directed to a method for selective functionalization of a microwire field effect transistor (FET) array in contact with individually addressable dielectrophoresis (DEP) electrodes, wherein each FET in the microwire FET array includes a source, a drain, and a microwire connecting the source and the drain. The method comprises (a) activating a subset of said DEP/EO electrodes; (b) introducing a solution containing a functionalizing element onto said array so as to allow said solution to contact the microwires of the FETs in contact with said subset; (c) flushing said solution; and (d) repeating acts (b) and (c) for each subset of FETs of said FET array requiring a different functional layer; wherein a set of differently functionalized FET microwires are obtained without requiring micropositioning.

Some embodiments are directed to a method of analyte detection. The method comprises providing a test sample including an analyte together with a waste product; providing at least one reference solution; transporting said test sample through a plurality of microfluidic channels; generating dielectrophoretic forces on said test sample as said test sample is transported through said plurality of microfluidic channels; separating said waste product from said analyte by said dielectrophoretic forces; directing said waste product away from said analyte; directing said analyte to a condensing area; condensing said analyte in a localized area; flushing said analyte with said reference solution to remove substantially all of remaining waste product from said condensed analyte; and detecting low amounts of analyte using a microfluidic sensor.

Some embodiments are directed to an apparatus for analyte detection. The apparatus comprises a first chamber configured to store a reference solution; a pump configured to pump a test sample and said reference solution; at least one injection chamber configured to introduce said reference solution and said test sample to a microfluidic separator; said microfluidic separator separating said product to be analyzed from microscaled components, said microfluidic separator including at least one microfluidic channel. The microfluidic channel includes electrodes for producing a force on said test sample when said test sample is pumped through said at least one microfluidic channel to separate said product to be analyzed from said microscaled components; and at least one channel for transporting said microscaled components away from said product to be analyzed.

Some embodiments are directed to a filtration system for analyte detection. The filtration system comprises microchannels for fluid transport; a dielectrophoretic separator for separating said fluid into constituent components; a dielectrophoretic condenser for condensing at least one constituent component of said fluid; a dielectrophoretic transport module; and a field effect based sensor, nanowire sensor, nanoribbon sensor, or ion sensitive field effect transistor, or any combination thereof, for detecting said at least one constituent component of said fluid.

Some embodiments are directed to a fluidic device that separates particles from unwanted components in a fluid by a force on the particles and/or the unwanted components in the fluid arising from an AC electric field in the fluid as the fluid transverses a channel where the frequency of the AC field has at least two independent frequencies.

Some embodiments are directed to a fluidic device that separates particles from unwanted components in a fluid by a force on the particles and/or the unwanted components in the fluid arising from an AC electric field in the fluid as the fluid transverses one or more channels, wherein the AC electric field is applied by a plurality of electrodes for delivering force to the particles or the unwanted components as the fluid traverses the one or more channels, and wherein the electrodes are configured as an arc, a ring, or a circle, and wherein the arc, ring, or circle has approximately a constant radius of curvature.

Some embodiments are directed to in a microfluidic device adapted for filtering and analyzing microorganisms from an entity to be eliminated, said device comprising dielectrophoresis (DEP) and/or electroosmosis (EO) electrodes, a method for highly selective filtration. The method comprises identifying a frequency and conductivity having a difference for a Clausius-Mossotti (CM) factor for said microorganisms and a CM factor for said entity to be eliminated; and filtering said entity to be eliminated by introducing a solution of the identified conductivity and by imposing an electric field having the identified frequency so as to separate said entity to be eliminated from said microorganisms.

Some embodiments are directed to a detection method. The method comprising transporting a test sample including an analyte and a waste product through a plurality of microfluidic channels; generating dielectrophoretic forces on said test sample as said test sample is transported through said plurality of microfluidic channels to separate said waste product from said analyte; directing said waste product away from said analyte; condensing said analyte; flushing said condensed analyte with a reference solution to remove substantially all remaining waste product from said condensed analyte; and analyzing, with a microfluidic sensor, the condensed analyte to detect the analyte.

Some embodiments are directed to a filtration system for analyte detection. The filtration system comprises a dielectrophoretic separator comprising at least one channel, wherein the dielectrophoretic separator is configured to separate constituent components of a fluid using dielectrophoresis as the fluid flows through the at least one channel; a dielectrophoretic condenser configured to condense at least one constituent component separated from said fluid by said dielectrophoretic separator; a dielectrophoretic transport module configured to transport the condensed at least one constituent component; and a field effect based sensor, nanowire sensor, nanoribbon sensor, or ion sensitive field effect transistor, or any combination thereof, configured to receive the condensed at least one constituent component from the dielectrophoretic transport module and detect said at least one constituent component.

Some embodiments are directed to a method of detecting the presence of a analyte in a sample. The method comprises monitoring a change in a noise levels or a change in a noise spectrum of a detected signal between a first signal when the analyte is not in close proximity to a sensor and a second signal when the analyte is in close proximity to the sensor.

Some embodiments are directed to a method of signal modulation, the method comprising performing signal modulation based on analyte contact with an electrode edge.

Some embodiments are directed to a device, comprising an electrode configured to be placed in an AC electric field, the electrode configured to operate as a virtual valve by preventing, using an AC kinetic trap, an analyte in solution flowing past the electrode from continuing past the electrode.

Some embodiments are directed to an apparatus, comprising at least one electrode configured to be placed in an AC electric field; and a controller configured to control at least one characteristic of the AC electric field to identify, without the use of labels, analyte particles in a solution located adjacent to the at least one electrode.

Some embodiments are directed to a switching technique for performing label-free spectral detection of analytes in a solution. Some embodiments are directed to an actionable spectrometer configured to measure a spectrum of a solution, then separate, isolate, detect, and/or identify an analyte in the solution. Switching between different frequencies of an applied electric field invokes dielectrophoresis or electroosmotic trapping. Such a technique may be used to measure a Clausius-Mossotti (CM factor) of an analyte.

Some embodiments are directed to using dielectrophoresis to trap analytes (e.g., bacteria) only at the edge of a sensor. Such a technique enables the use of sensors with a larger form factor than nanowire sensors and may result in improved reliability of manufacturing with a decreased manufacturing cost. Additionally, since the dielectrophoresis force traps bacteria on the edge of the electrode, causing a contact between the bacterium and the electrode, bacterial presence changes potential on the electrode or sensor surface and causes a measurable difference in the current or capacity.

Some embodiments are directed to a technique for applying an AC electric field directly to the terminals of a device.

Some embodiments are directed to a technique for integrating of high surface coverage electrodes with the sensor (where the sensor is e.g., electrical or optical) to effectively overcome diffusion limitations in analyte transport. One aspect allows for the use of the geometry of the active channel chosen such as to have a high surface coverage to increase the probability of analyte interaction with the sensor surface or confinement within proximity to the sensor and analyte detection. Some embodiments are directed to a technique to adjust the shape of the electrodes with center symmetric structures or structures with covered or partially covered non-center symmetric regions to enhance efficiency of EO streamline formation, EO trapping and capture.

Some embodiments are directed to a technique for controlling induced analyte motion between trapping centers.

Some embodiments are directed to a technique for detecting the motion of an analyte in a solution. The detected motion may be used to indirectly determine the presence/absence of the analyte in the solution by analyzing an output signal over time.

Some embodiments are directed to sensitive, accurate, rapid detection and identification of bacteria, viruses, analyte, and microscale components in liquid suspensions.

Some embodiments are directed to a device and method for highly sensitive, accurate detection and identification of bacteria, viruses, analyte, and microscale components in fluid samples. In one aspect, embodiments may perform general separation and detection functions.

A device in accordance with some embodiments uses an RF electric field, AC kinetics and dielectrophoresis for purposes of separation in a novel manner, namely by choosing values of frequency and conductivity causing maximal separation force between the analyte and other elements in the incoming solution being tested.

One aspect allows for selective treatment of individual sensors, such as nanowires or FET based sensors in a sensor array, such that each sensor or group of sensors can be made sensitive to a particular bacteria, viruses, analyte, or microscale components or family of bacteria, viruses, analyte, or microscale components.

Another aspect involves the use of electroosmosis in addition to dielectrophoresis for transport.

Yet another aspect allows for use of a net-connected device for purposes of transmitting diagnostic information to a server adapted to store and analyze trends involving many diagnoses from multiple locations. This allows for tracking of the spread of disease, for example.

Yet another aspect allows for testing of a cellular response to antibiotics and/or chemicals. By using a highly specific separation technique in accordance with some embodiments, isolation of particular bacteria, viruses, analyte, or other microscale components is performed and these are subject to particular antibiotics. The cell lysis products are then analyzed by a microwire array sensor, optically, or using another suitable sensing method.

Yet another aspect allows for detection of viruses and/or proteins by coating a subset of the active element of the sensor array with appropriate binders as used in PCR or immunoassays.

Another aspect is directed to implementing a database configured to track bacterial resistance. A particular patient's bacterial fingerprint may be sensed and compared to this database allowing for treatment with specific antibiotics or other drugs (e.g., microbiome therapies) known to be effective and the particular spectrum of bacteria present in this patient. The resistance of bacteria over time and geographically may further be monitored with such a database.

Applications of systems and methods in accordance with some embodiments include inline sensors for IV lines, for early detection of infection and/or monitoring of bacteria, viruses, analyte, microscale components toxins such as endotoxins. Such applications are suitable, for example, for inline glucose sensors or dialysis machines which are prone to bacterial infection. Another application of such a system is blood purification from bacteria and viruses.

A further application is directed to detection of sulfate-reducing bacteria, for indirect measurement of sulfur levels.

A further application is directed to analyzing the levels of metabolic byproducts, such as glucose, ATP, pH etc. in time using the sensor system. By using a highly specific separation technique in accordance with some embodiments, isolation of particular bacteria, viruses, analyte, or other microscale components is performed. Then detection or analysis of metabolic byproducts may be performed.

A further application is directed to purifying water or other fluids from contaminants.

A further application is directed to water or fluid filtration and/or testing in a continuous mode.

A further application is directed to purifying water and using the purified water to dilute the original sample to extract, capture, separate or detect contaminants or analytes.

Yet another aspect allows for processing the sample in one connected chamber.

Yet another aspect allows for processing the sample without the use of valves.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF THE DRAWINGS

Various non-limiting embodiments of the technology will be described with reference to the following figures. It should be appreciated that the figures are not necessarily drawn to scale.

FIGS. 11A-D illustrate electrodes with different geometries in accordance with some embodiments;

FIGS. 17A-17C show images of data obtained using the third electrode configuration shown in FIG. 11A, where E. coli bacteria are shown to travel freely in an EO trap along the trap lines;

FIG. 37 shows a top view (above) and a cross section (below) of a transistor configured as a biosensor in accordance with some embodiments;

FIG. 38 shows a device in which the source and drain contacts are electrodes in accordance with some embodiments;

FIGS. 41 and 42 show a device with a planar silicon or semiconductor layer where the active channel of the transistor is formed;

FIG. 43 shows a device where the source and drain contacts are electrodes in accordance with some embodiments;

FIGS. 49A-J illustrate schematic views of a device for pretreatment of a reference solution or a low conductivity solution or water followed by mixing the reference solution with the sample and analyte capture and separation with possible detection and identification in accordance with some embodiments;

DETAILED DESCRIPTION

The disclosure may be understood from the following detailed description, which is meant to be descriptive and not limiting. For the sake of brevity, some well-known features, methods, systems, procedures, components, circuits, and so on, are not described in detail.

The term 'DEP' hereinafter refers to dielectrophoresis, or the force of an electric field gradient on objects having dielectric moments. The term 'CM factor' hereinafter refers to the Clausius-Mossotti factor upon which the DEP force depends. The term 'EO' hereinafter refers to electroosmosis.

Although there have been recent advancements in microfluidics manufacturing technologies and in biosensor manufacturing, integration of complex microfluidic systems with RF electric fields and nanoscaled silicon sensors remains expensive and resource intensive. Additionally, analyte diffusion to the sensor surface is a limitation in sensor performance and may cause false negatives. The need for labeled detection, involving binding or a label, a molecular recognition element to the sensor surface or to the analyte, may also cause false negatives, false positives and limit the selectively of an assay.

Separation of Analyte Using Dielectrophoresis

Figure 1:
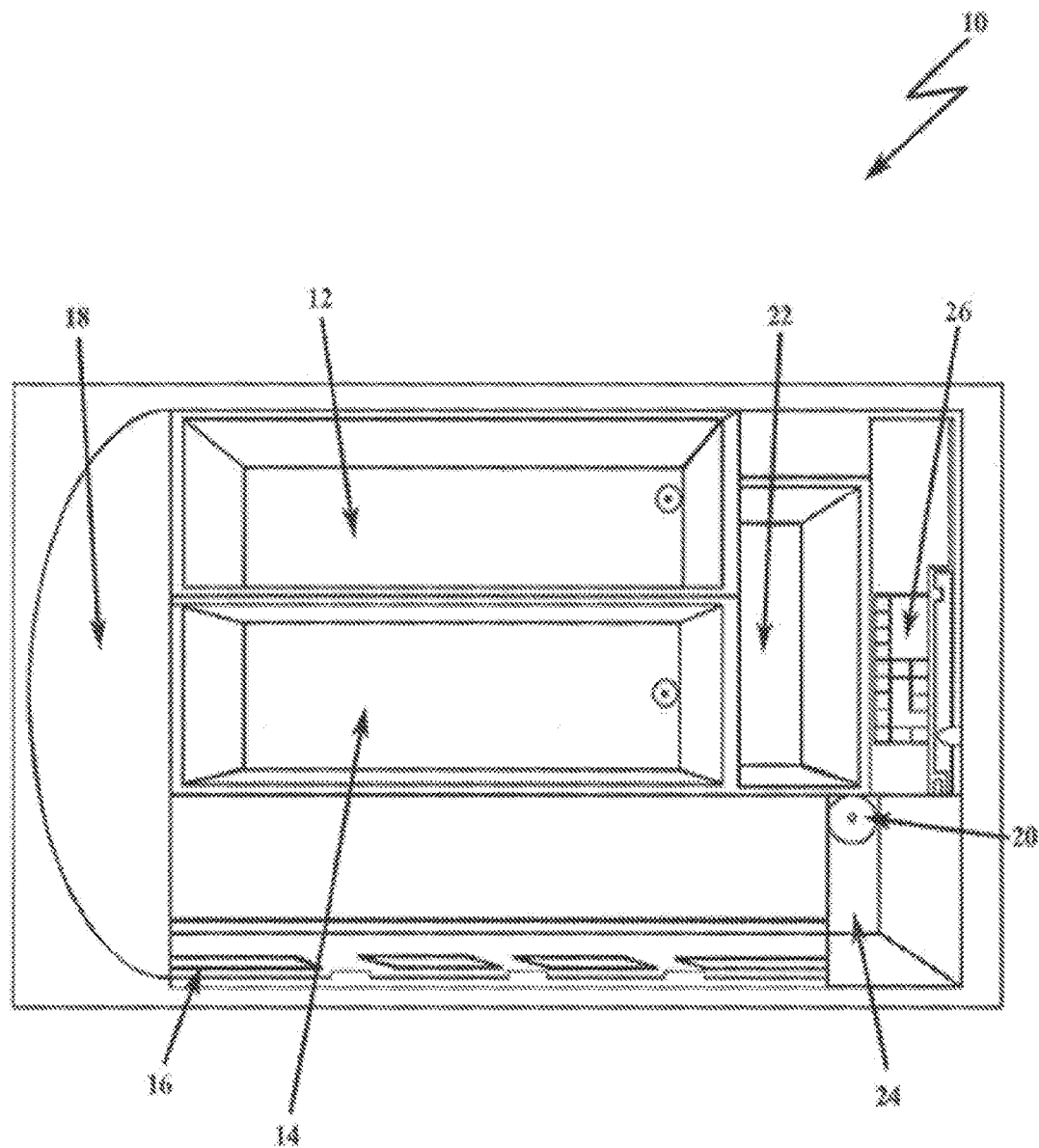
FIG. 1 illustrates a fluidics device for separating an analyte from other components in a fluid.

Some embodiments allow for separation of analyte from confounding factors and analysis of the analyte alone. A fluid sample to be analyzed is obtained and inserted into the device, which may have an overall design such that shown in FIG. 1, which is reproduced from U.S. Pat. No. 9,120,105, which is herein incorporated by reference. Device 10 in FIG. 1 comprises a sample chamber 12 and a chamber 14 containing a reference solution which may in some embodiments include a separator which purifies the reference solution from contaminants. In some embodiments, the device 10 may not include the chamber containing the reference solution.

The chambers 12 and 14 are connected by pump adapted to force either fluid around the passage 18 and through separator passage 16. First, the solution containing analyte and other elements is pumped through the separator. The separator applies a dielectrophoretic, electroosmotic, or AC kinetic force on the elements of the solution tending to draw the analyte towards the bottom of the figure and the 'uninteresting' elements (to be disposed of) towards the top. The elements to be disposed of can then be trapped in chamber 22, while the analyte of interest is drawn into the holding chamber 24 by concentrator 20, which the separator and the condenser may in some embodiments comprise a set of coaxial interdigitating rings or arches having independent voltages. Once the analyte is held by the concentrator 20, the buffer solution may be pumped from chamber 12 around the bend 18 and through the separator passage 16 to flush the chamber 24, effectively changing the medium in which the analyte is found and eliminating any residual unfiltered elements. The analyte can then be released from concentrator 20 (by removing the electric field) and drawn towards analyzer array 26 (which itself is provided with DEP electrodes adapted to draw the analyte thereto).

The device uses dielectrophoresis for purposes of separation in a novel manner. Dielectrophoresis uses a natural or induced dipole to cause a net force on a particle in a region having an electric field gradient.

$$F = 2\pi \varepsilon_m R^3 Re[\underline{CM}(\omega) \cdot \nabla \underline{E}^2(r,\omega)]$$

This force depends on the Clausius-Mossotti factor CM(w) defined by $$CM(\omega) = \frac{\epsilon_p^o - \epsilon_m^o}{\epsilon_p^o + 2\epsilon_m^o}$$

where $\in^o$ is the complex permittivity, $$\epsilon^o = \frac{\sigma}{i\omega}.$$

In some embodiments, the values for σ and ω are chosen such that a separation force between the analyte and other elements in the incoming solution being tested is effective to separate the analyte from the other elements. In some embodiments, a maximum separation force between the analyte and other elements in solution may be used. In other embodiments a separation force less than the maximum separation force but nonetheless effective in separating the analyte from the other elements in the solution may be used. Determination of the separation force to be used for separation of the analyte from other elements in the solution may be accomplished by compiling knowledge concerning both the analyte and the materials to be separated. For example in FIG. 2, a possible CM factor for a particular bacteria is shown beside a second graph of the CM factor for a red blood cell, these graphs showing CM factor as a function of frequency of applied field and conductivity of the fluid in which the DEP force is being applied. Some embodiments, described in more detail below, are directed to a label-free technique for determining one or more CM factor curves (e.g., as a function of frequency). A library of CM factor curves may be created for different analytes and may be used to select an ideal frequency for analyte separation and/or for performing identification of an analyte in solution by comparing a determined CM factor curve for an analyte being tested with the CM factor curves in the library.

In some embodiments, operating parameters for determining a separation force include not only frequency of an applied AC electric field. For example, the operating parameters may also include one or more of electric field voltage, phase, solution conductivity, electrode metal, electrode geometry, electrode edge roughness, flow rate, height and/or geometry of a microfluidic channel, characteristics of an applied waveform, and chemical composition of the solution.

Figure 2:
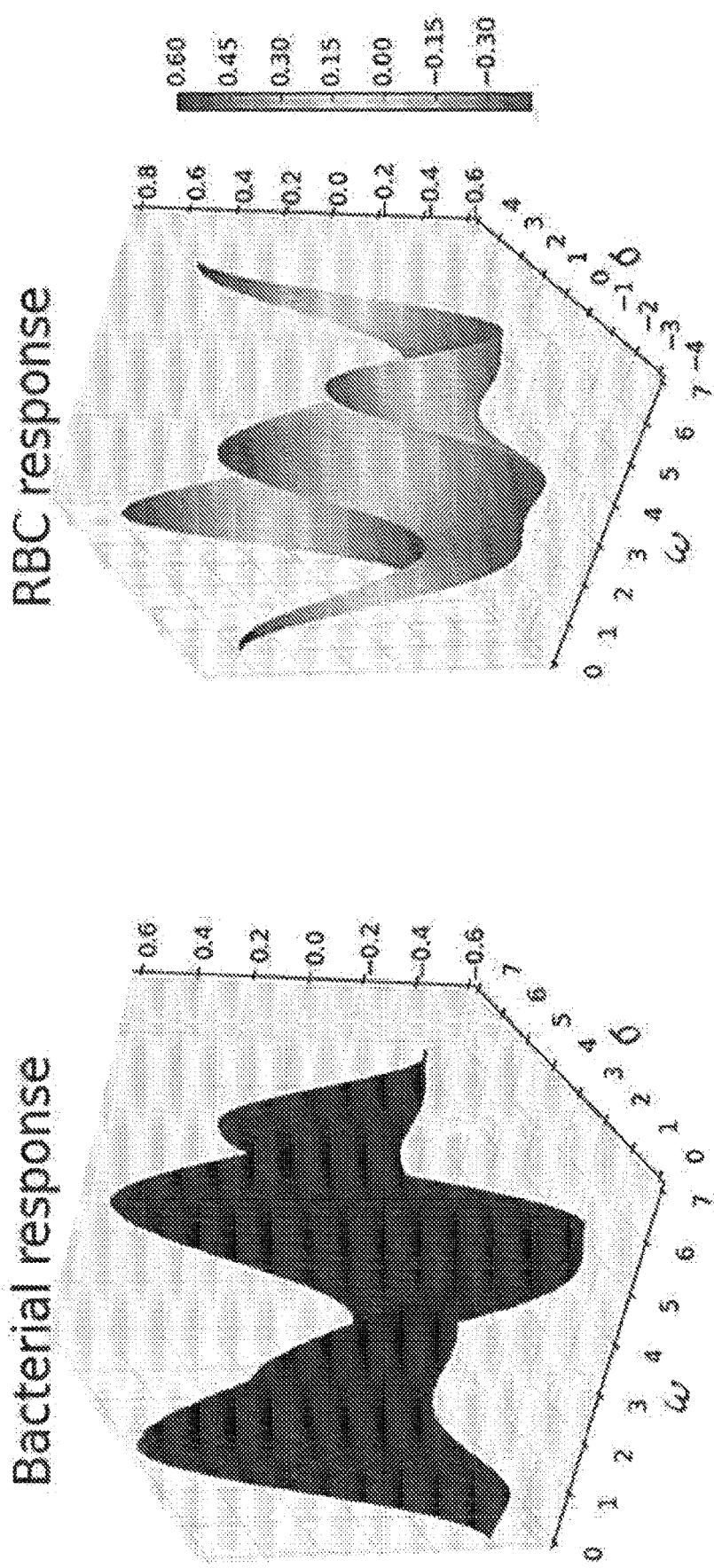
FIG. 2 shows graphs of CM factor as a function of frequency of an applied electric field and conductivity of a fluid in which a dielectrophoresis force is being applied, for bacteria and red blood cells, in accordance with some embodiments.
Figure 3:
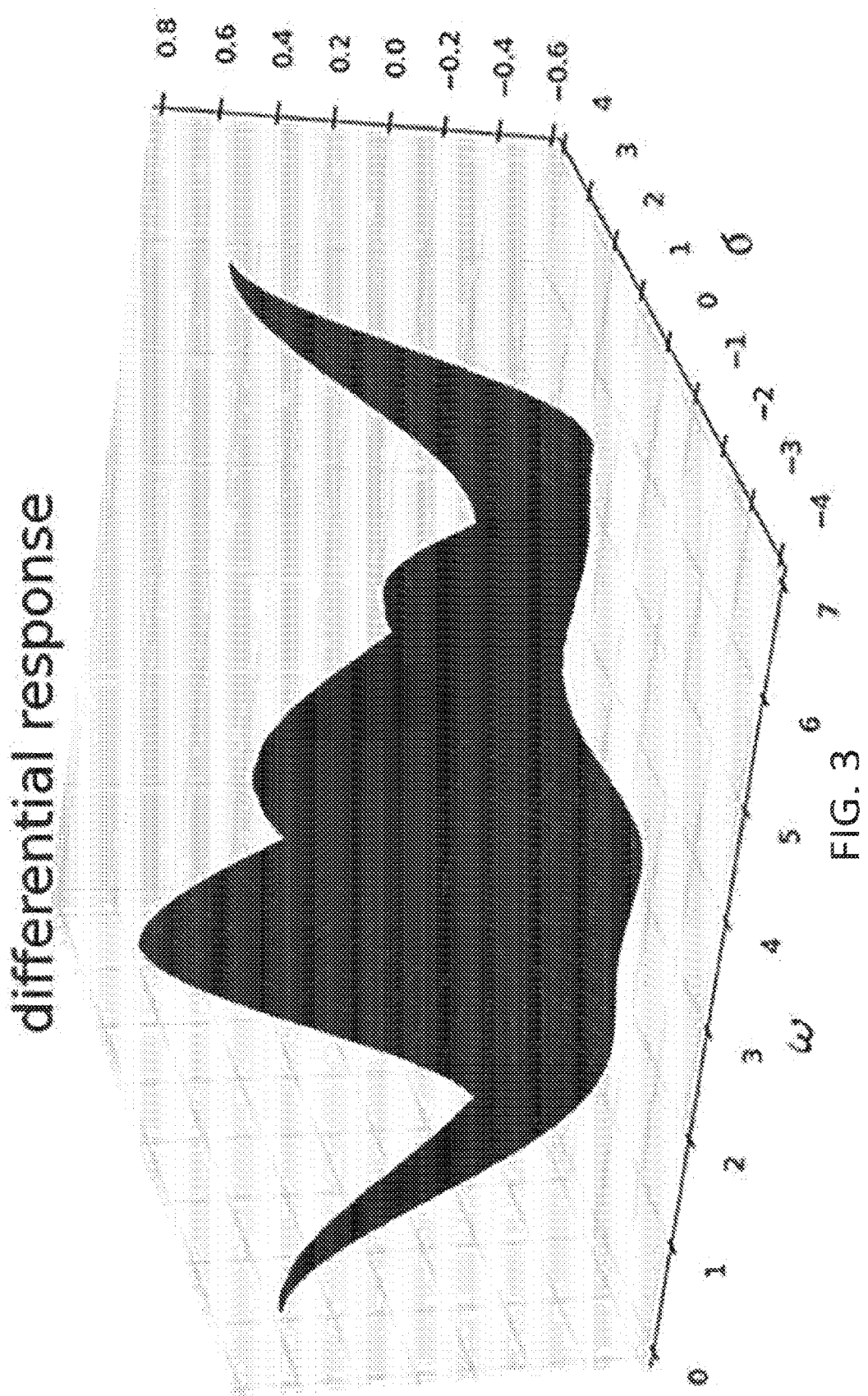
FIG. 3 shows a graph of a differential response between the two graphs shown in FIG. 2.

After compiling graphs such as those shown in FIG. 2, the differential response of FIG. 3 can be inspected for its extrema which will show the greatest differential response tending to separate the analyte from the material to be filtered. The frequency for effective separation is selected for use (this being the frequency of the applied field), while the conductivity of the solution can be controlled by titration of a known amount of solution of known conductivity (or equivalently, salinity). Alternatively a feedback technique may be used by measuring the conductivity of the solution and adding saline or deionized water (for instance) until a desired conductivity or other operating parameters are reached. A reference measurement may be used for quality control and identification of the solution. A differential measurement of the control signal (no contamination) with an actual signal (e.g., with labeled contaminants) may be used. Conductivity measurements, permittivity measurements, and/or measurements of other fluid parameters may be implemented at multiple stages in the devices for quality control of fluid mixing and feedback adjusting the mixing rate.

Bacterial motion dynamics depend on the viscosity of the solution. In some embodiments, characteristics of particle motion induced with a controlled electric field is used to determine the viscosity and/or complex permittivity of the solution.

As will be appreciated by one skilled in the art, such a graph can be constructed for any pair of species in question in a given solution of complex permittivity; thus, for example, different kinds of bacteria may be separated from one another, or different types of blood cells may be separated from one another, or different bacteria, viruses, analyte, microscale components may be separated from one another. Furthermore, successive filtration steps can be taken to (for example) first separate bacteria from red blood cells (RBC), and then separate bacteria from white blood cells (WBC) then, if needed, further separate multiple analytes from each other. Similarly, successive filtration steps can be taken to, for example, first separate bacteria microbiome samples, and then separate bacteria from each other.

Figure 4:
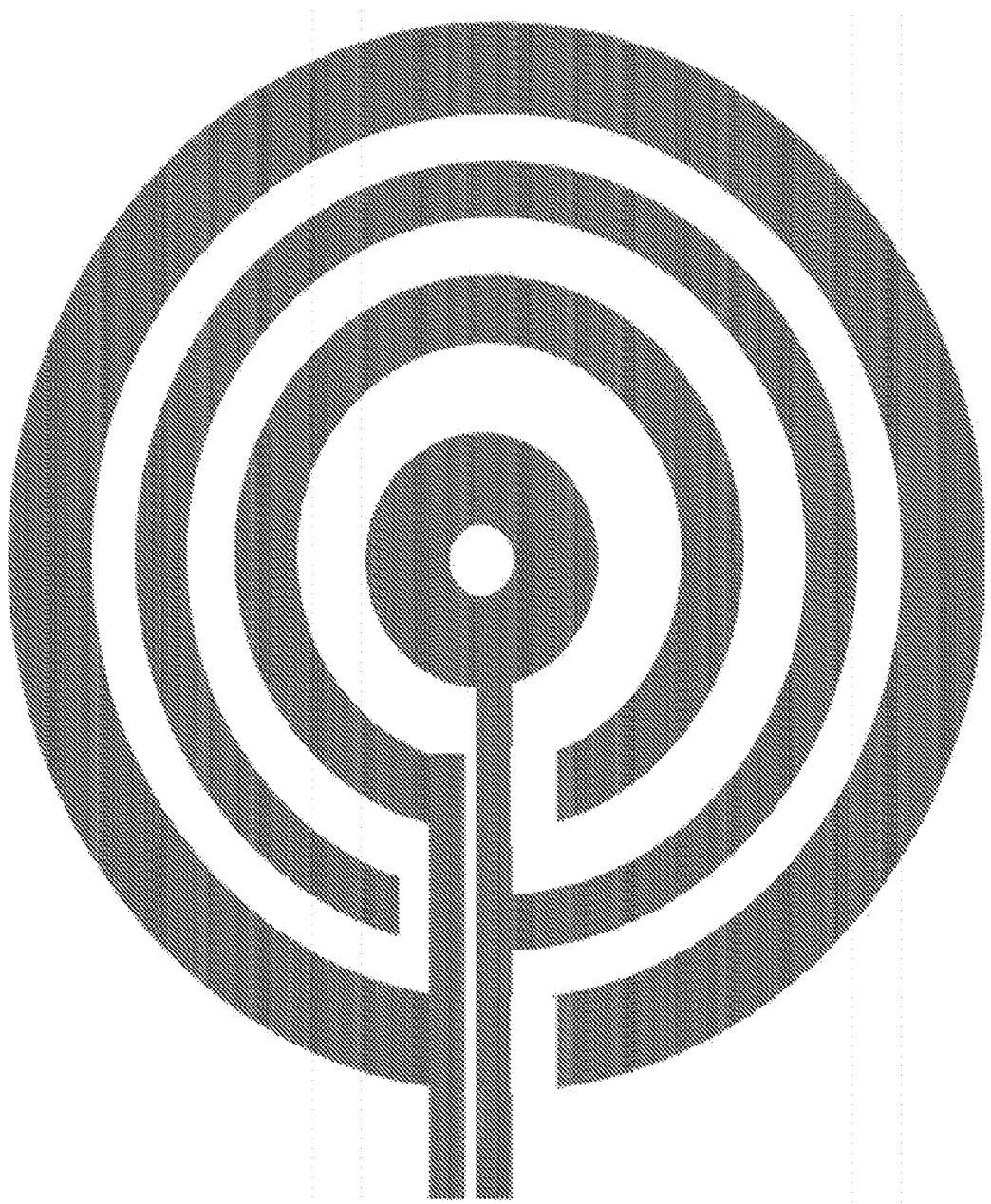
FIG. 4 illustrates a circular assembly of electrodes that may be used in accordance with some embodiments.

Some embodiments make use of a circular assembly of coaxial- or circularly-shaped electrodes or a partially center-symmetric electrodes, such as shown in FIG. 4, where two or more independent voltages may be applied to the odd and even rings. This allows for an electric field gradient to be created in the region between the rings. In accordance with some embodiments, the assembly of electrodes is constructed in such a way as to maximize the effects of the electric field on controlling the motion of the analytes.

Figure 5:
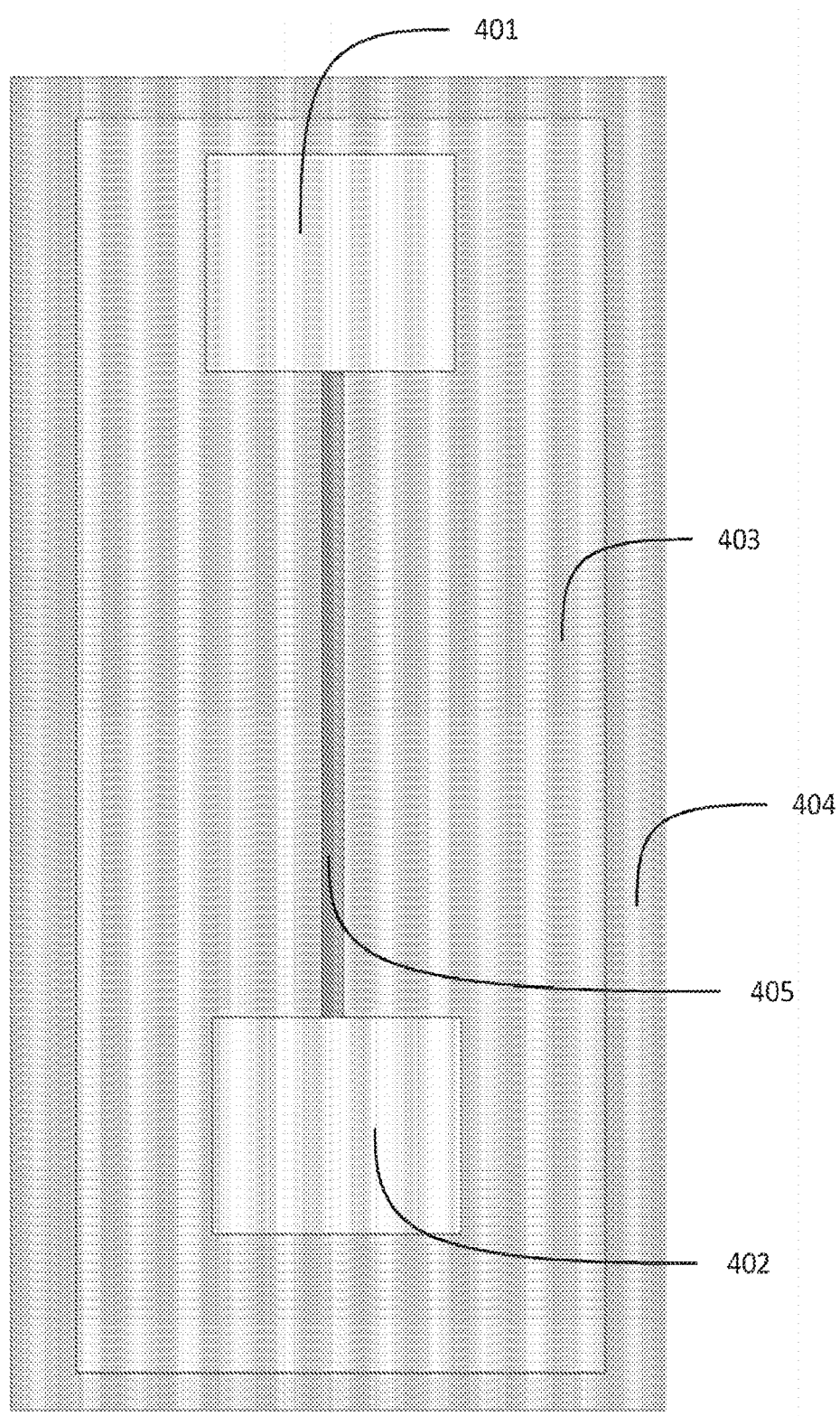
FIG. 5 illustrates a sensor assembly that may be used in combination with the electrode assembly of FIG. 4 in accordance with some embodiments.

Such a device may be used to draw bacteria, viruses, analyte, microscale components, or other elements to the sensor array, which may be composed of elements such as those shown in FIG. 5, namely source 401 and drain 402, nanowire, nanoribbon or active sensing layer 405, silicon or other semiconducting substrate 404 and SiO2 or other insulating interlayer 403.

Figure 6:
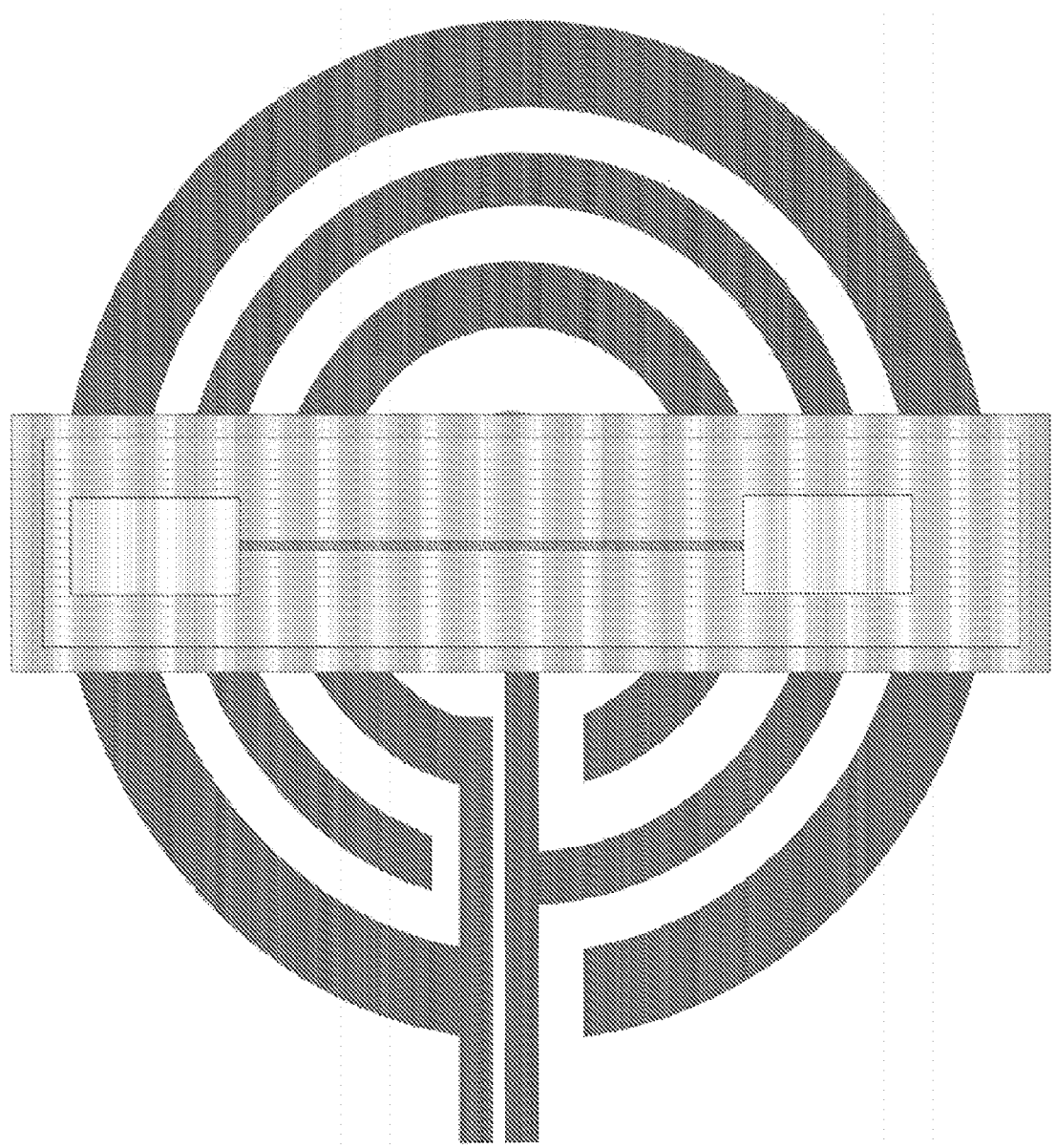
FIG. 6 illustrates the sensor assembly of FIG. 5 fabricated on top of the circular electrode assembly of FIG. 4 in accordance with some embodiments.
Figure 7:
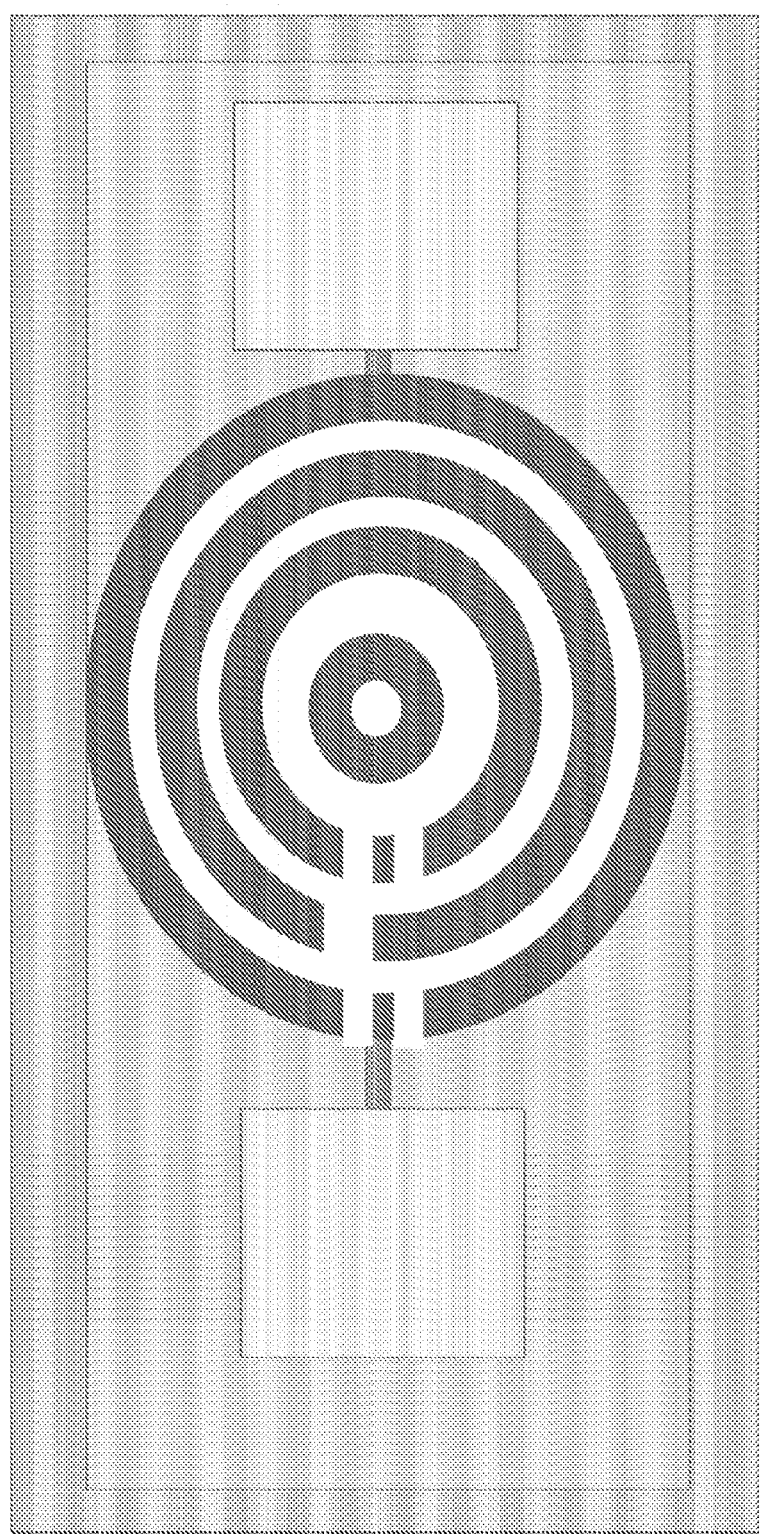
FIG. 7 illustrates the circular electrode assembly of FIG. 4 fabricated on top of the sensor assembly of FIG. 5 in accordance with some embodiments.
Figure 8:
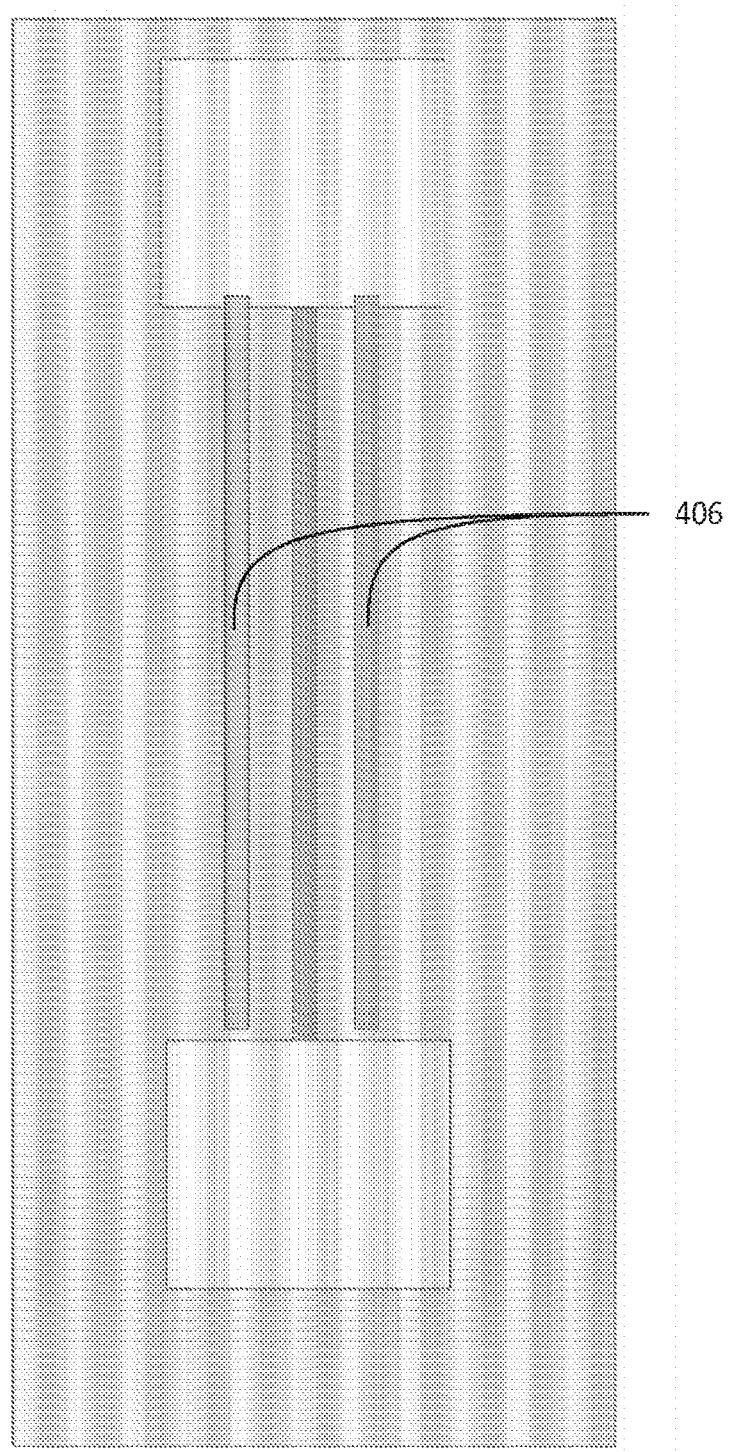
FIG. 8 illustrates a device that includes supplementary wires arranged to provide a field gradient in a region of a central sensing layer in accordance with some embodiments.

The sensor assembly of FIG. 5 may be fabricated on top of circular DEP electrodes as shown in FIG. 6, or a set of circular electrodes may be fabricated on top of (or underneath) the SiO2 or other insulating layer as shown in FIG. 7. Alternatively, two supplementary wires 406 may be used as shown in FIG. 8 to provide a field gradient in the region of the central sensing layer.

Selective Treatment of Sensors

A further aspect allows for selective treatment of individual sensors in a sensor array, such that each sensor or group of sensors can be made sensitive to a particular bacteria, viruses, analyte, microscale components or family of bacteria, viruses, analyte, microscale components. The sensor array may be such as that disclosed in U.S. application Ser. No. 12/517,230, which is herein incorporated by reference. In some embodiments, the wires of the array form the bases of field-effect transistors, and thus implement nanowire FETs or FETs.

One practical difficulty in the creation of a sensor array is the application of unique labels to each of the sensing elements. Some embodiments address this problem felicitously by use one or both of the techniques described below.

Both techniques require that each individual element of the array can be individually addressed electrically.

A first technique in accordance with some embodiments uses the fact that there is some breakdown voltage for passivating polymer layers or other coating materials, e.g., BSA, that may be used to prevent electrodes from being functionalized (coated with functional molecules). Thus for instance the entire array can be coated with a passivating polymer layer. A particular electrode is chosen for functionalization. A voltage is applied to the electrode that is known to be above a threshold for breakdown of the passivating polymer layer; thus the layer above this electrode (and only this region) will be eliminated. The entire array can then be exposed to a functionalizing solution (comprising for instance antibodies, markers, molecular recognition elements or the like) but only the chosen electrode (which now lacks the protective polymer layer) is functionalized. Each electrode can in turn be 'depassivated' and exposed to functionalizing solutions. One practical aspect of this technique is that each functionalized electrode will be exposed to the following functionalizing layers, and thus good adhesion and complete coverage are goals for this step. Alternatively, the passivating layer can be re-applied after every functionalizing layer.

Figure 9A:
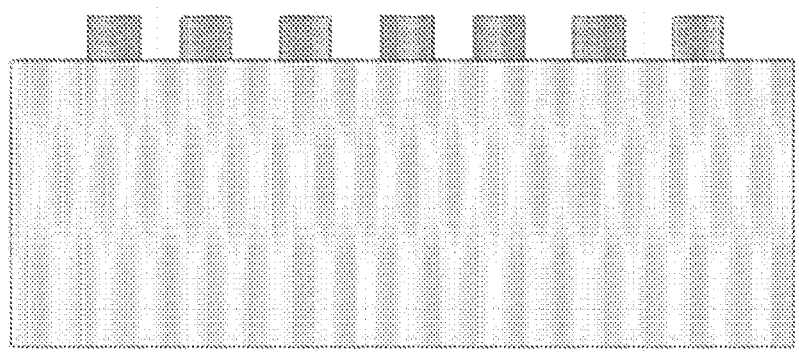
FIGS. 9A-D illustrate steps in a process for fabricating a sensor assembly in accordance with some embodiments.
Figure 9B:
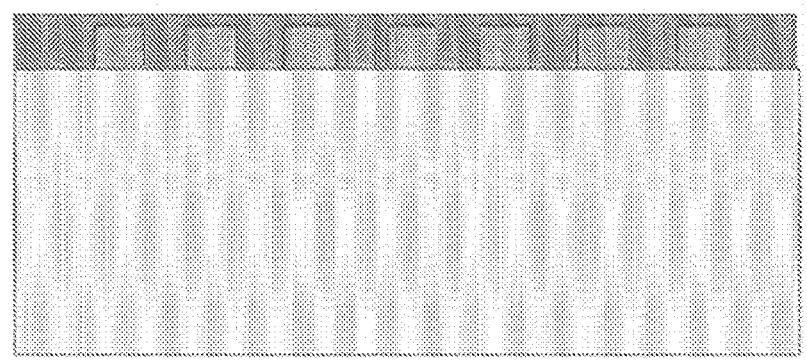
Figure 9C:
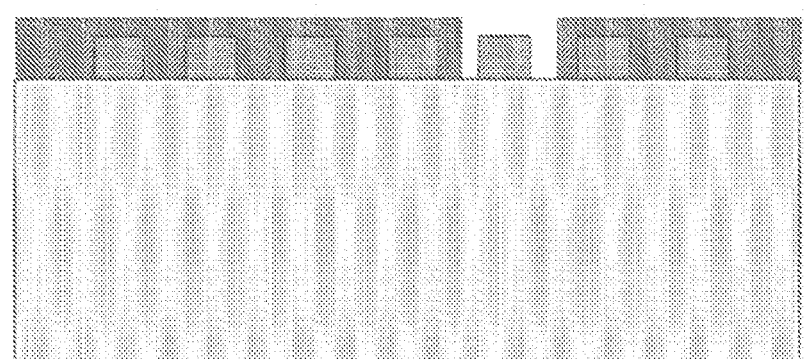
Figure 9D:
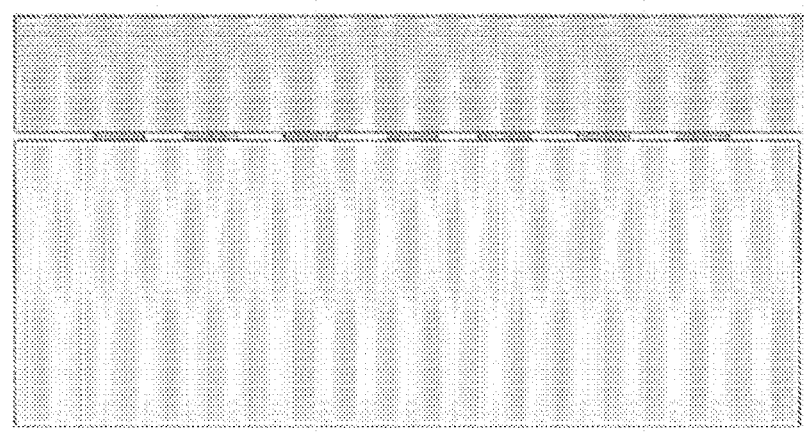

FIGS. 9A-D show a schematic of this technique; in the step illustrated in FIG. 9A, the bare sensor assembly is shown from the side. FIG. 9B shows the assembly after application of a passivating layer. FIG. 9C shows the assembly after removal of the layer over one electrode onto which a large field was applied. FIG. 9D shows a functionalizing layer which has been applied to the entire device but which can only contact the single electrode which has been revealed.

A second technique in accordance with some embodiments involves use of the DEP force to selectively draw functionalizing molecules or elements to specific electrodes. Each sensing electrode is preferably near an individually controllable DEP/EO electrode. This DEP/EO electrode may be activated to draw the functionalizing element towards the sensor electrode; this sensor electrode will thus be selectively exposed to the functionalizing element. Each sensing element may thus be in turn exposed to different functionalizing elements, thus reaching a full set of independently functionalized electrodes eventually.

Figure 10A:
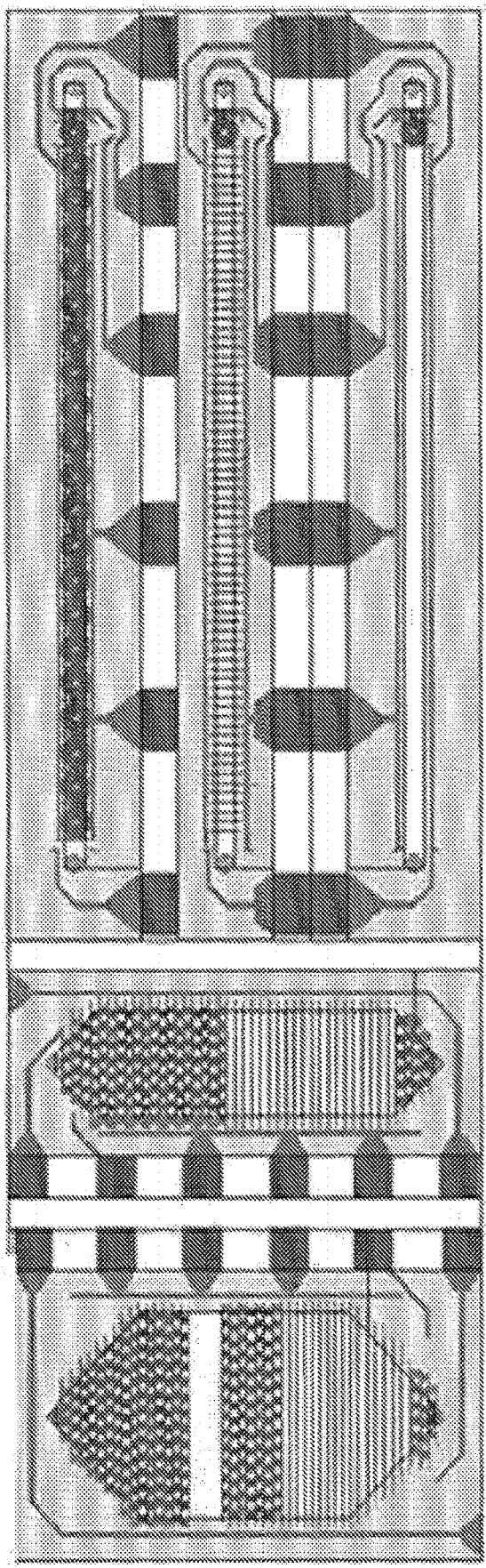
FIG. 10A illustrates a layout for a fluidic device in accordance with some embodiments.
Figure 10B:
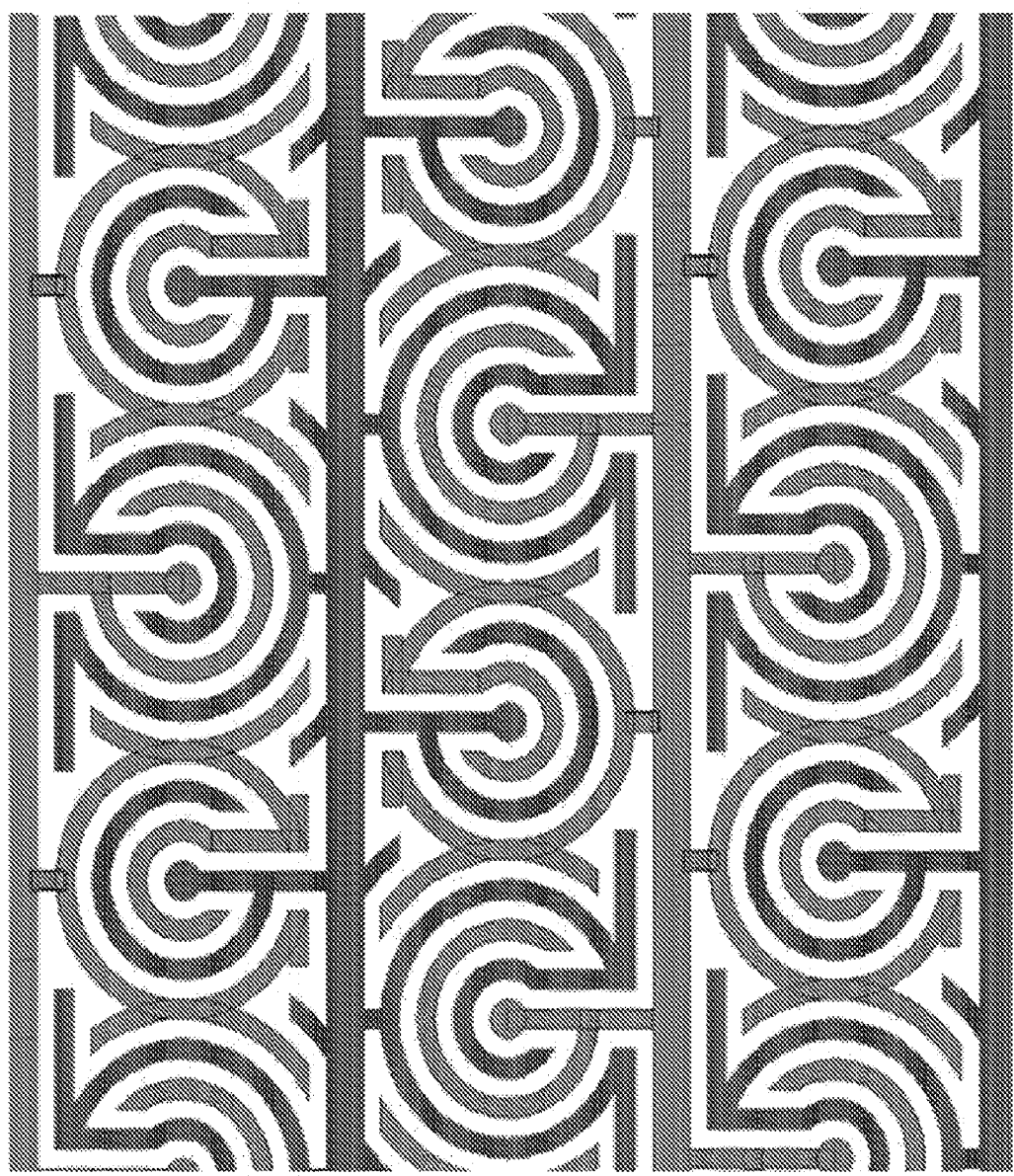
FIGS. 10B-H illustrate different geometries of electrodes for high surface coverage to achieve high electric field gradients in accordance with some embodiments.
Figure 10C:
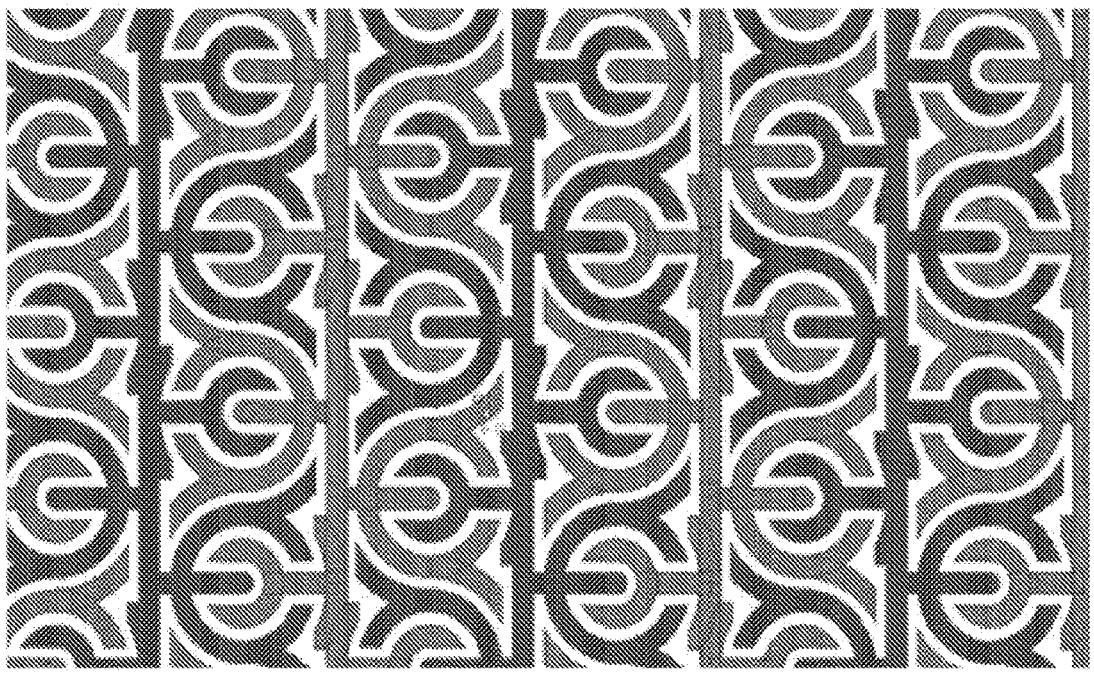
Figure 10D:
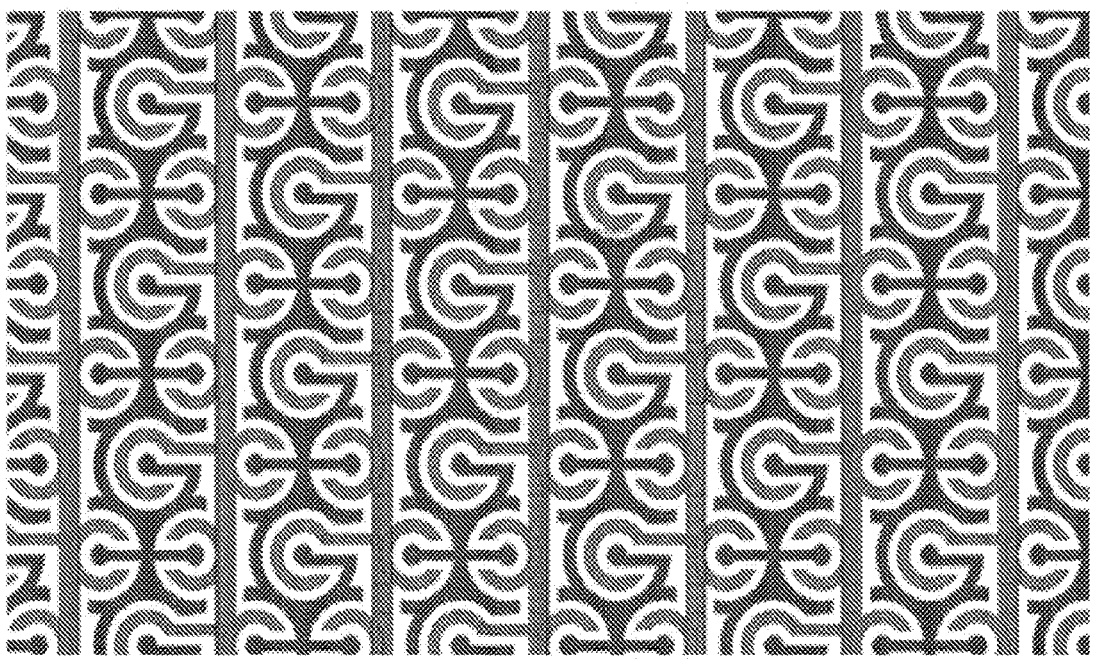
Figure 10E:
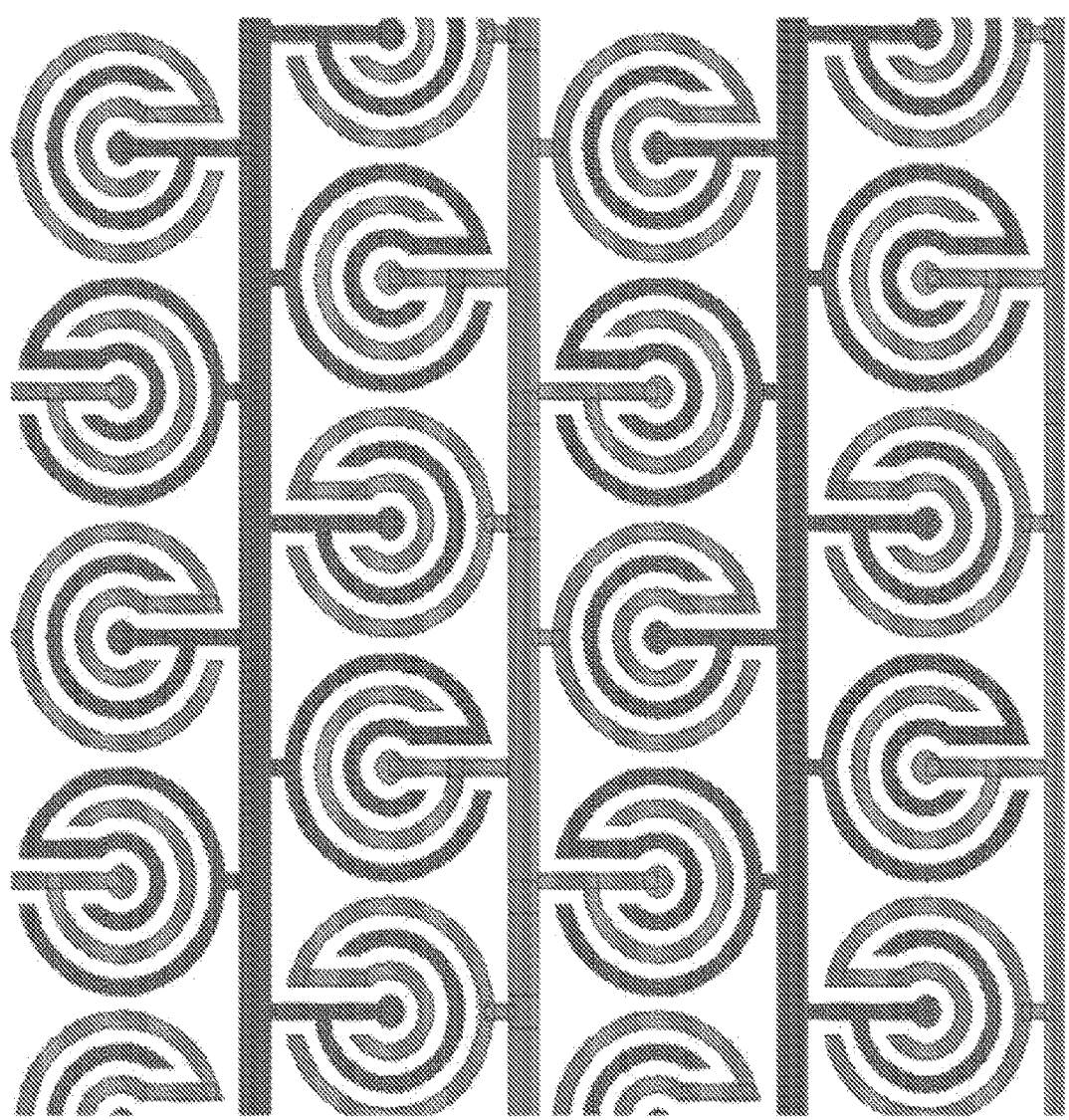
Figure 10F:
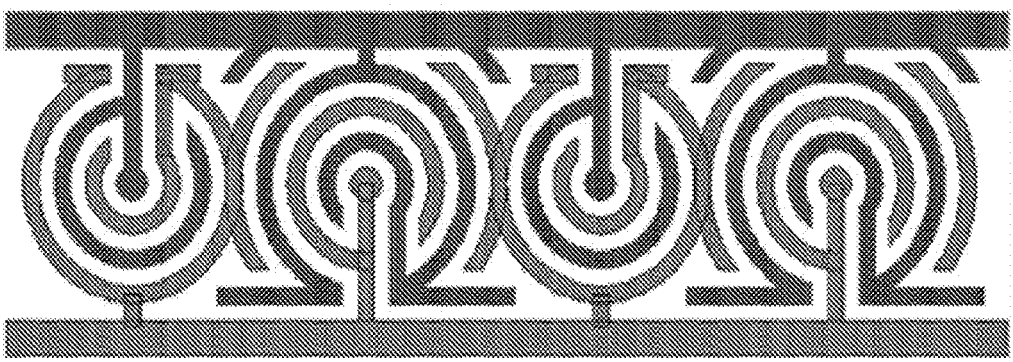
Figure 10G:
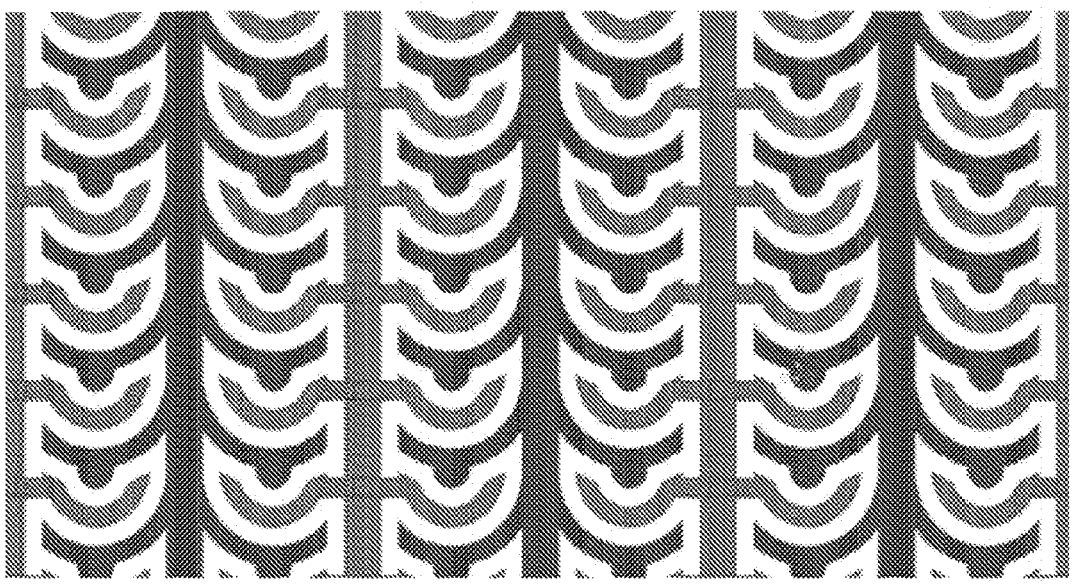
Figure 10H:
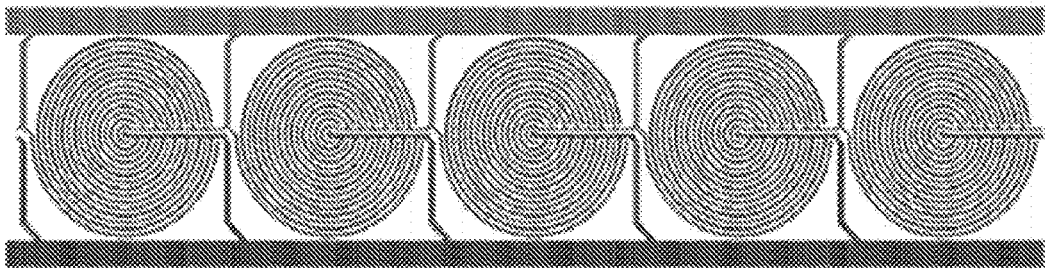

FIG. 10A shows the layout of a microfluidic device in accordance with some embodiments. FIGS. 10B-H illustrate different geometries of electrodes for high surface coverage to achieve high electric field gradients in accordance with some embodiments. In some embodiments, an electrode having one of the geometries shown in FIGS. 10A-H may cover the entire surface of a chamber (e.g., wall, top and/or bottom) of a fluidic device, examples of which are discussed above. The spacing between electrodes may be chosen to be less than the length of the depletion zone. The electrodes induce high field gradients, so that bacteria, viruses, analyte, or microscale components introduced into the chamber are exposed to high electric fields regardless of their position in the chamber. Such an electrode design with a high surface coverage allows, in some embodiments, for control of over 99% of bacteria, viruses, analyte, or microscale components present in the sample and reduces false negatives. In FIGS. 10B-H, the light and dark shaded lines illustrate opposing polarities of the voltage applied.

A further aspect in accordance with some embodiments involves the use of electroosmosis in addition to dielectrophoresis for transport. The frequencies at which electroosmosis are effective (e.g. tens of kHz) are widely separated from those useful in DEP, and therefore the two methods can be used simultaneously to provide a larger variety of separation regimes, and for a wider variety of objects to be separated.

Another aspect in accordance with some embodiments allows for use of a smartphone or other network-connected device for purposes of transmitting diagnostic information to a server adapted to store and analyze trends involving many diagnoses from multiple locations. This allows for tracking of the spread of disease, for example. A diagnostic device in accordance with some embodiments may be provided with communications functionality such as BlueTooth, WiFi, NFC, or the like to communicate with network-connected devices such as a smartphone, PDA, laptop, router, desktop or other device. By sending information such as the number and type of bacteria, viruses, analyte, microscale components s detected, location, time, or other suitable information, the spread of particular bacteria, viruses, analyte, microscale components s can be traced without requiring personal patient information. If patient information is sent, the diagnostic information gleaned by use of the device may be entered into patient profiles for access by subsequent physicians, researchers, and the like. Yet another aspect of some embodiments is directed to a function generator, frequency clock or data acquisition system connected to a smartphone that receives amplification and/or power from the smartphone.

Yet another aspect of some embodiments is directed to testing of a cellular response to antibiotics or other chemicals. By using the highly specific separation provided by some embodiment, isolation of particular bacteria, viruses, analyte, or microscale components may be performed and subjected to further detection and/or identification. The cell lysis products may then be analyzed either by a microwire array sensor or optically. In this way a wide variety of antibiotics or other treatments may be tested against a wide array of bacteria, viruses, analyte, microscale components. The antibiotics may be introduced for instance by using the chamber 12 (FIG. 1) or may be introduced from a separate chamber provided for this purpose. Another aspect of some embodiments provides a number of different solutions intended to kill bacteria, viruses, analyte, or microscale components, and to test them individually and in combination. Some embodiments provide a cost effective and accurate technique for such analyses.

Yet another aspect of some embodiments provides for detection of viruses and/or proteins. This may be accomplished by coating a subset of the sensors of the sensor array elements with appropriate binders, such as those as used in PCR. The coating may be accomplished using any suitable technique, examples of which are known in the art, as well as those techniques described above (passivation of all electrodes, selective depassivation of individual electrodes, and subsequent functionalization; or by use of DEP to attract functionalizing elements to individual electrodes).

Some embodiments implement a database adapted to track bacterial resistance. A particular patient's bacterial 'fingerprint' (e.g., type and concentrations of various bacteria, viruses, analyte, or microscale components, including bacteria and possibly viruses) may be sensed and stored in this database which is preferably online. This fingerprint may be compared to other fingerprints in the database, and effective treatments may be found (for example preferentially choosing effective treatments on patients having close genetic makeup, age, race, sex or the like). This allows for treatment of bacteria, viruses, analyte, or microscale components with specific antibodies known to be effective for the particular spectrum of bacteria present in this patient, for physically similar patients. The resistance of bacteria over time and geographically may further be monitored with such a database.

Some applications of the systems and methods in accordance with some embodiments include inline sensors for IV lines, for early detection of infection and/or monitoring of bacteria, viruses, analyte, microscale components or toxins. Such applications are suitable, for example, for inline glucose sensors which are prone to bacterial infection. The sensing of toxins or other bacteria, viruses, analyte, or microscale components output can be accomplished using one or more the of techniques described above, for example, by selective sensitization of a particular subset of nanowires in the nanowire array sensor. As long as a functional group that is able to selectively bind with the toxin in question is available, and this group can be effectively bound to a wire of the nanowire array, detection is possible. In a label-free operation, the sensor may detect changes of pH caused by toxin excretion.

Some applications of the systems and methods in accordance with some embodiments include inline filtration and/or separation systems for early detection of contamination and/or monitoring of bacteria, viruses, analyte, microscale components, toxins in drug or food manufacturing, water quality monitoring, or bioterrorism prevention.

Some applications of the systems and methods in accordance with some embodiments include sensors that measure the pH changes in a solution when bacteria excrete toxin under stress from an external stimulus.

A further application of some embodiments is detection of sulfate-reducing bacteria, for indirect measurement of sulfur levels.

Yet another aspect of some embodiments implements an extended path exposing analyte to the electric field (or electric field gradient) over the electrode system. The dimensions of the electrodes and the spacing between electrodes in three dimensions is comparable to the length of the depletion zone (FIG. 10).

Figure 52A:
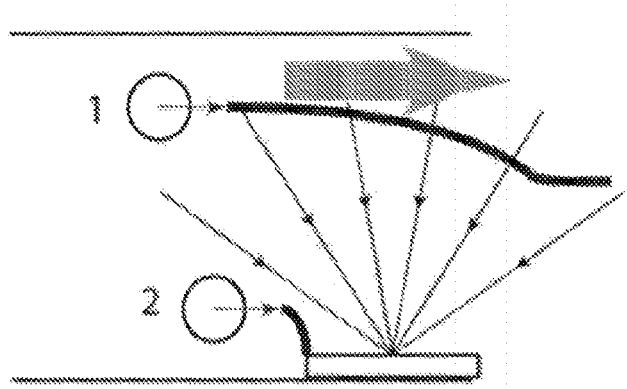
FIGS. 52A-B show analyte particles in microfluidic channels captured with an electrode system in accordance with some embodiments.
Figure 52B:
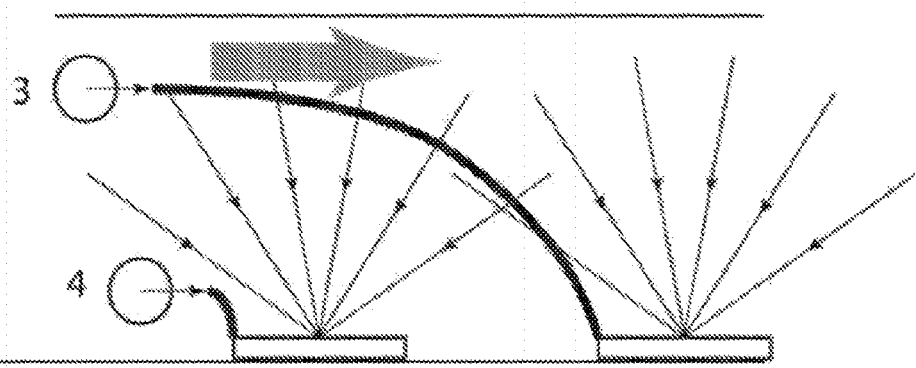

Yet another aspect of some embodiments implements a repeated or elongated electrode system to extend the trapping length and the length of the capture zone, as shown in FIGS. 52A and 52B. An elongated and/or repeated electrode structure improves capture of additional and/or faster moving analyte particles in accordance with some embodiments. The length of the capture zone determines the contact time required for the analyte to be captured on the electrode system as shown in FIG. 52A. A longer capture zone allows for capturing of an analyte moving faster and/or further away from the electrode system as shown in FIG. 52B.

Figure 14:
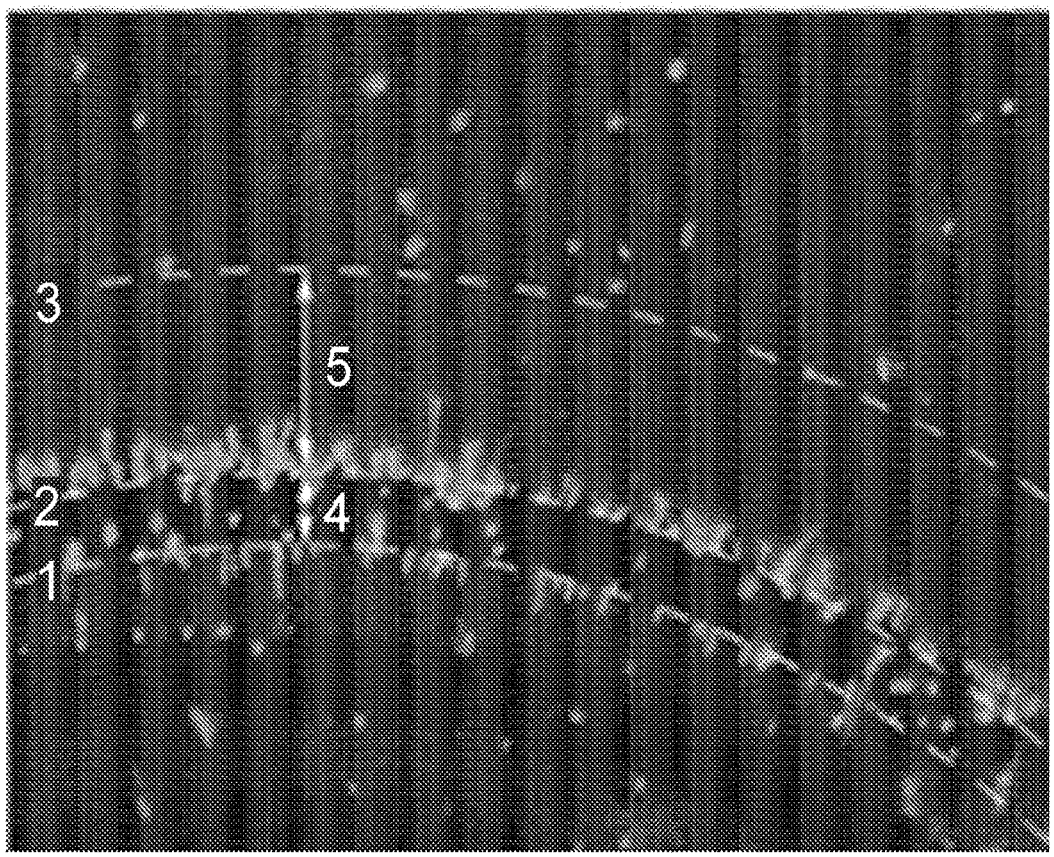
FIG. 14 illustrates shows E. coli bacteria capture on an electrode system designed in accordance with some embodiments.

The depletion zone denotes the maximum distance from the trapping center (either center of the dielectrophoresis trap or the center of the electroosmosis trap) from which analytes reach the trapping center within seconds when subjected to the electric field (dielectrophoresis or electroosmosis force) as shown in FIG. 14. The smallest distance and electrode geometry provides the highest electric field gradient of the device. The smallest distance between electrodes with opposite polarity or ground affects heat deposition in the system, may cause capacitive coupling, and electrode degradation effects thus being a limiting performance factor. Spacing electrodes within the length of the depletion zone causes bacteria and analytes to respond to the electric field within seconds, which is a basis for efficient capture and separation.

Yet another aspect of some embodiments allows applying a surface coating to protect electrodes from damage at DC or low frequency electric field bias or high ionic strength of a solution.

Recent advances in plastic microfabrication and injection molding allow creating plastic parts with precision electrodes. This approach enables high manufacturing reproducibility, larger part area and lower cost. Incorporation of valves increases the number of parts, thus increasing device complexity and costs of manufacturing.

Yet another aspect of some embodiments allows for implementing the electrode system in one chamber, with one or more chambers connected in series where electrodes cover at least one wall or plate and the spacing between electrodes is comparable to the depletion length (FIG. 10).

A large chamber lateral dimension in comparison to the other dimension in the cross section (chamber width to chamber height) allows increasing or maintaining high volume throughput.

Yet another aspect of some embodiments allows for implementing two or more electric potentials simultaneously or consecutively to the electrode system to achieve highly specific separation, by initial broad spectrum capture and the application of an electric field of a frequency acting on a group of interest, highly efficient concentration of analyte, control of analyte motion, and/or a virtual valve comprised of attractive or repulsive forces arising from AC kinetics, dielectrophoresis or electroosmosis. Applying a high-frequency electric field sequentially or simultaneously repelling analyte from the electrode system allows creating virtual barriers preventing analyte from entering certain regions of the device. The use of AC kinetics enables the capture of a broad spectrum of analytes (e.g., *E. coli, Enterococcus, Aestuariimicrobium kwangyangense, Bacillus, Mycobacterium, Mycoplasma, Propionibacterium acnes, Staphylococcus piscifermentans, Streptococcus pneumoniae*).

Yet another aspect of some embodiments allows for application of a voltage NDEP to repel analyte from the whole sample before buffer exchange FIGS. 11A-D show electrodes with different geometries in accordance with some embodiments. In the different geometries the ratio of the critical feature size (electrode width and electrode spacing) and the depletion length is changed from the baseline electrode width and spacing of 25 µm. This ratio determines two factors: the efficiency of AC kinetics (electroosmotic) capture and the efficiency of dielectrophoresis capture. The switching between electroosmosis and dielectrophoresis additionally allows controlling bacterial motion and transport between electrodes.

Figure 11A:
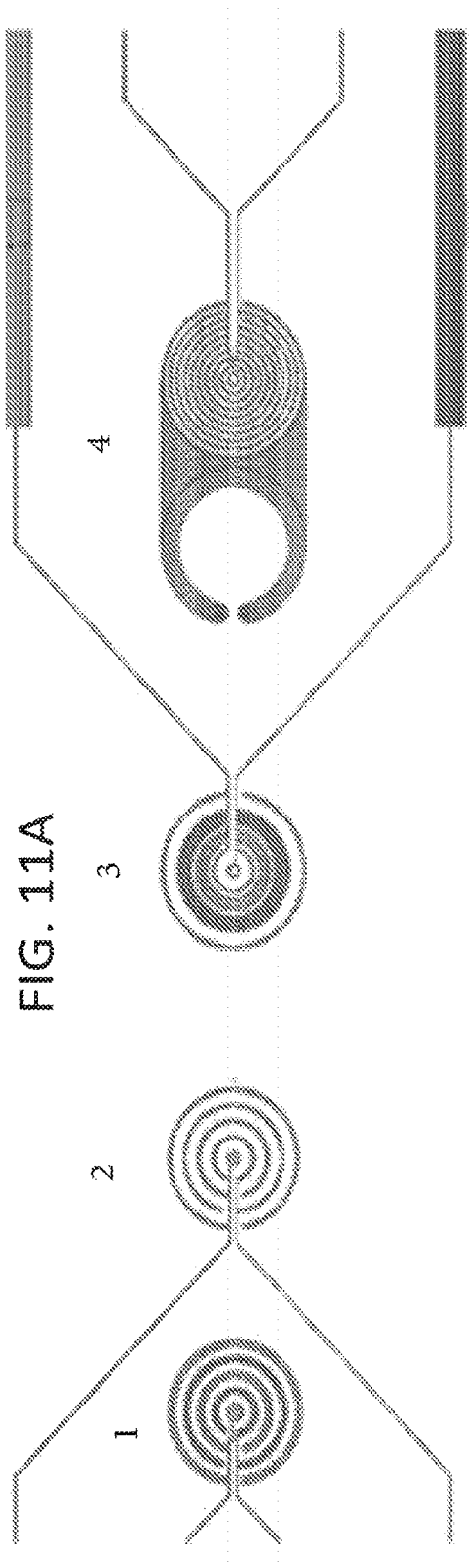
Figure 16A:
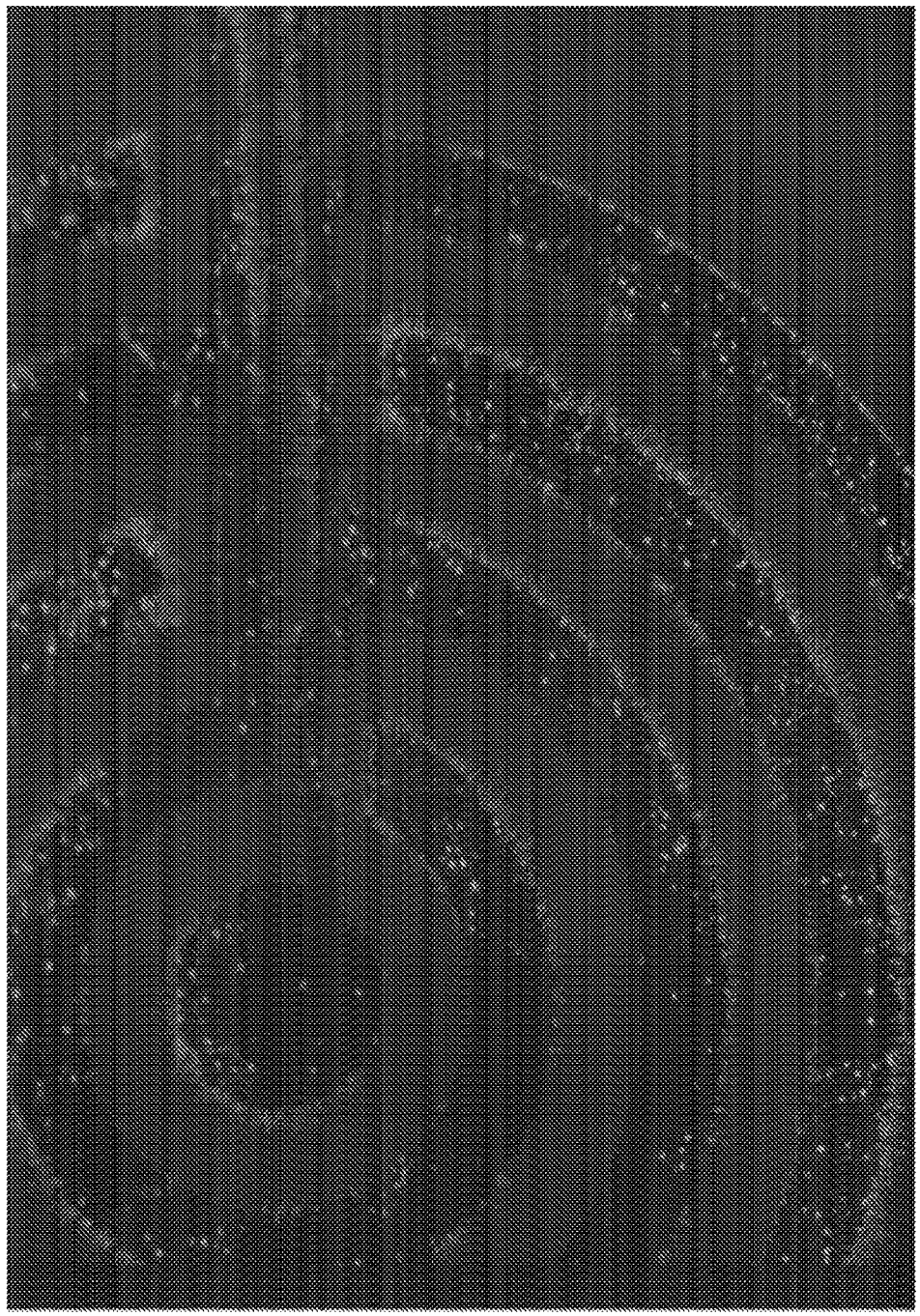
FIGS. 16A and 16B show images of E. coli bacteria being captured on the first and second electrode configurations shown in FIG. 11A, respectively.
Figure 16B:
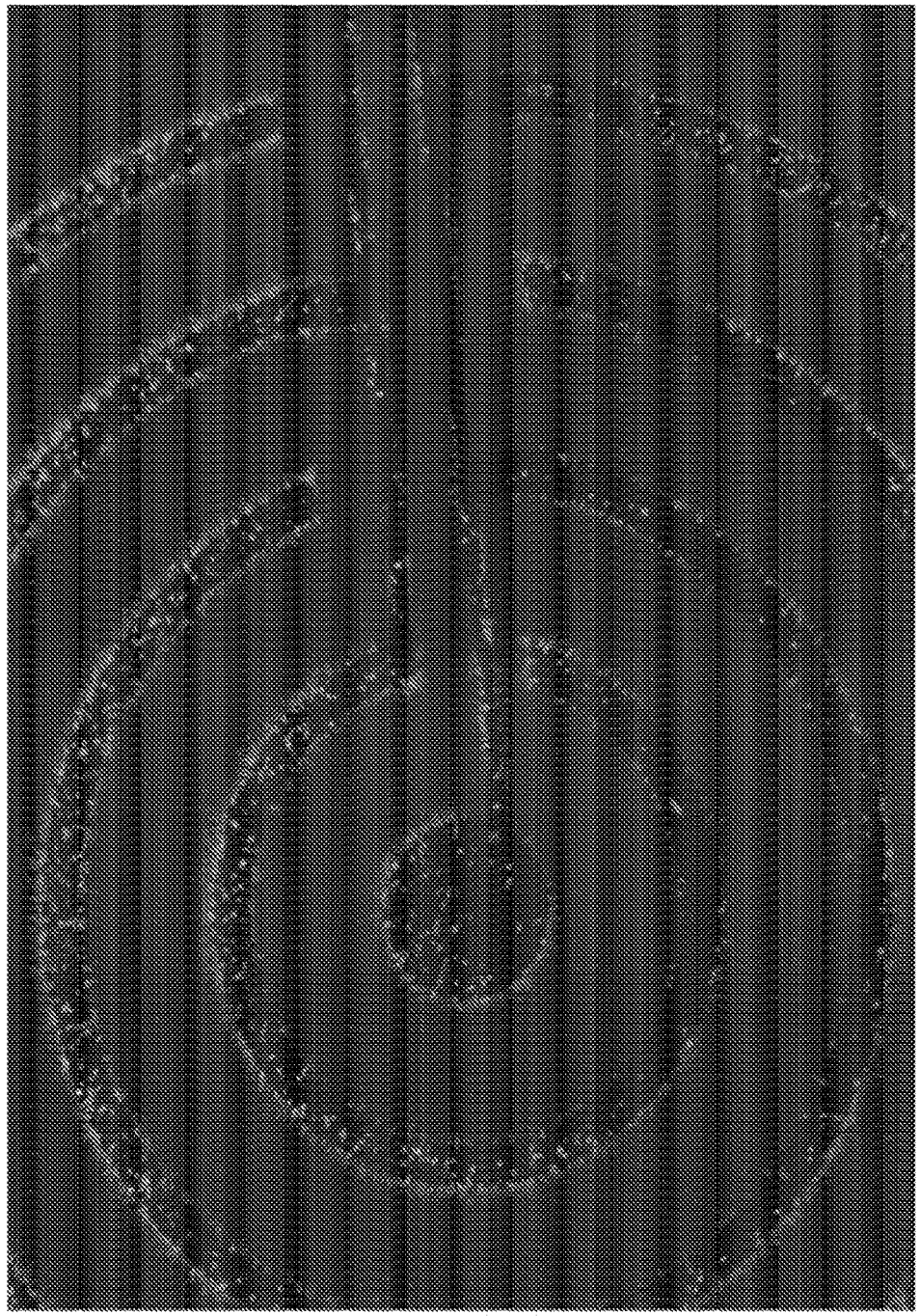

The electrode layouts shown in FIG. 11A are discussed as follows (1) Electrode width and spacing are both set to 50 µm. As shown in FIG. 16A, analytes (e.g., bacteria) are still efficiently captured using electroosmosis and AC kinetics and the dielectrophoresis force has a weaker range (the electrode width and depletion length ratio is increased from when the electrode width and spacing was set to 25 µm). The image in FIG. 16A shows capture at 10 kHz and 10V of fluorescently modified *Enterococcus* bacteria. The larger feature size in this configuration may improve manufacturability. (2) Electrode width set to 25 µm, electrode spacing set to 50 µm. The results of using this electrode configuration are shown in FIG. 16B. The image in FIG. 16B shows captures at 10 kHz and 10V of fluorescently modified

*Enterococcus* bacteria. (3) Electrode width and electrode spacing varies (not constant). The results of using this electrode configuration are shown in FIGS. 17A-C. FIGS. 17A-C show capture at 10 kHz and 10V of fluorescently modified *Enterococcus* bacteria. As shown, the centers of the electroosmotic traps are shifted and the analyte (bacteria) is shown sliding for intra electrode transport. In particular, the analyte (*Enterococcus* bacterium) slides in a 10 kHz, 10V electric field along the electroosmotic trap in the intraelectrode space from an initial positions 1 and 2 in FIG. 17A, along the path to position 1 and 2 in FIG. 17B to positions 1 and 2 in FIG. 17C, finally reaching the collection point 2 in FIG. 17C. (4) Extended electroosmosis trap and intra electrode analyte transport.

Figure 11B:
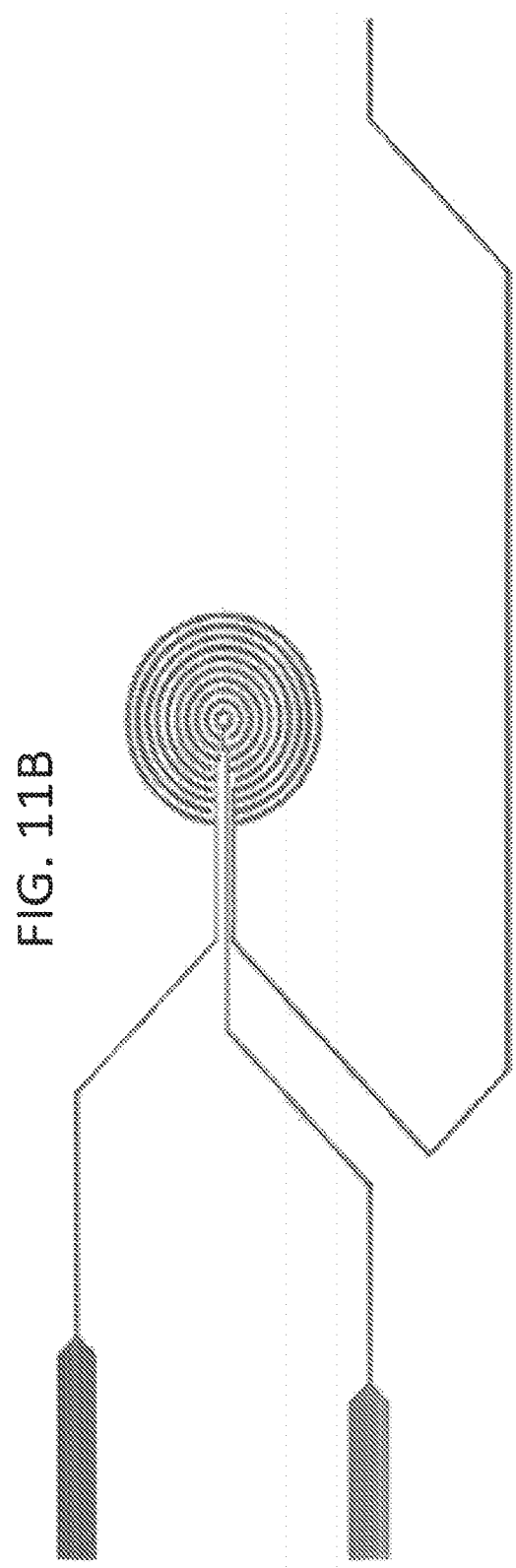
Figure 18:
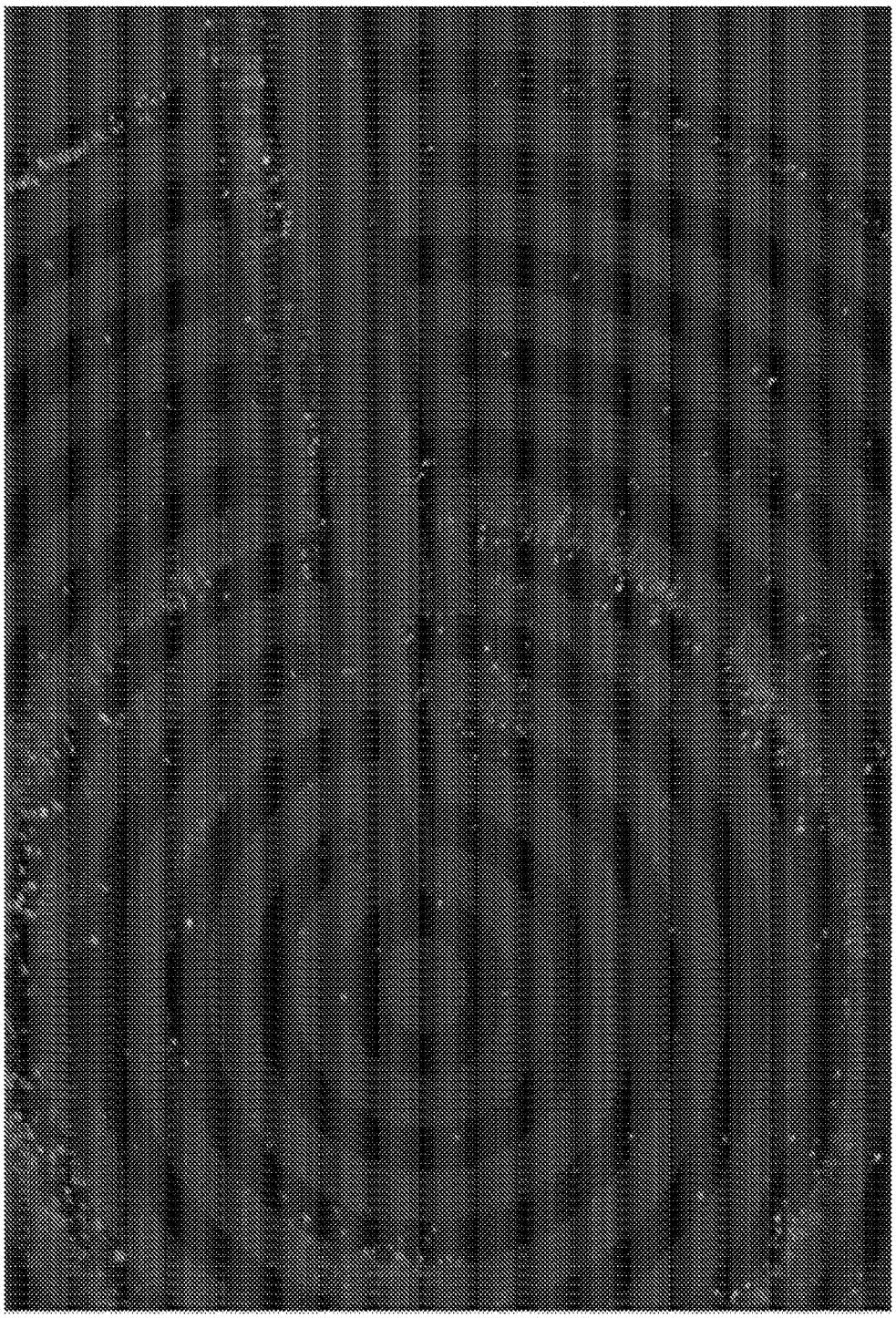
FIG. 18 shows an image of data obtain using the electrode configuration shown in FIG. 11B indicting that based on a preferential voltage distribution, bacteria show a distribution of capture on the electrode system.

FIG. 11B shows a three-terminal electrode in accordance with some embodiments. Such a structure allows applying electric field simultaneously or consecutively with two or more frequencies or amplitudes. This structure also allows for additional electric field modulation to differentiate between two different analyte types or achieve broad spectrum analyte capture using AC kinetics (dielectrophoresis and/or electroosmosis). Additionally, such a structure with floating electrodes (unconnected terminal) allows analyte capture with an induced voltage. The results of using this electrode configuration is shown in FIG. 18. The image in FIG. 18 shows capture at 10 kHz and 10V of fluorescently modified *Enterococcus* bacteria.

FIG. 11C shows two electrode structures with outer electrodes connected to extend an electroosmosis trap and achieve intra electrode analyte transport. Although only two electrode structures are shown, it should be appreciated that more than two electrode structures may also be used in this configuration in some embodiments.

FIG. 11D shows two electrode structures with outer electrodes at the same or opposing polarity to achieve inter electrode analyte transport. Although only two electrode structures are shown, it should be appreciated that more than two electrode structures may also be used in this configuration in some embodiments.

Yet another aspect of some embodiments allows for AC kinetics or electroosmosis broad spectrum capture of analytes (e.g., *E. coli* and *Enterococcus*). Yet another aspect of some embodiments allows for positive dielectrophoresis for selective capture of analytes of interest. Yet another aspect of some embodiments allows for fluid flow, pulsed or continuous release of analyte from a AC kinetic trap in the absence or presence of electric fields, and transport to the next trapping center. Another aspect of some embodiments use EO kinetic capture in flow long range to overcome a depletion layer limit. The capture electrode for a PDEP hydrodynamic stable trap for PDEP can then be used to control *E. coli* move trajectory. Yet another aspect of some embodiments allows for analyte focusing with interelectrode connects—bacteria transport along surfaces defining centers of EO traps—use for focusing within microfluidic channel (FIGS. 10 and 11).

An aspect of some embodiments allows fabrication in a monolithic device.

Figure 12:
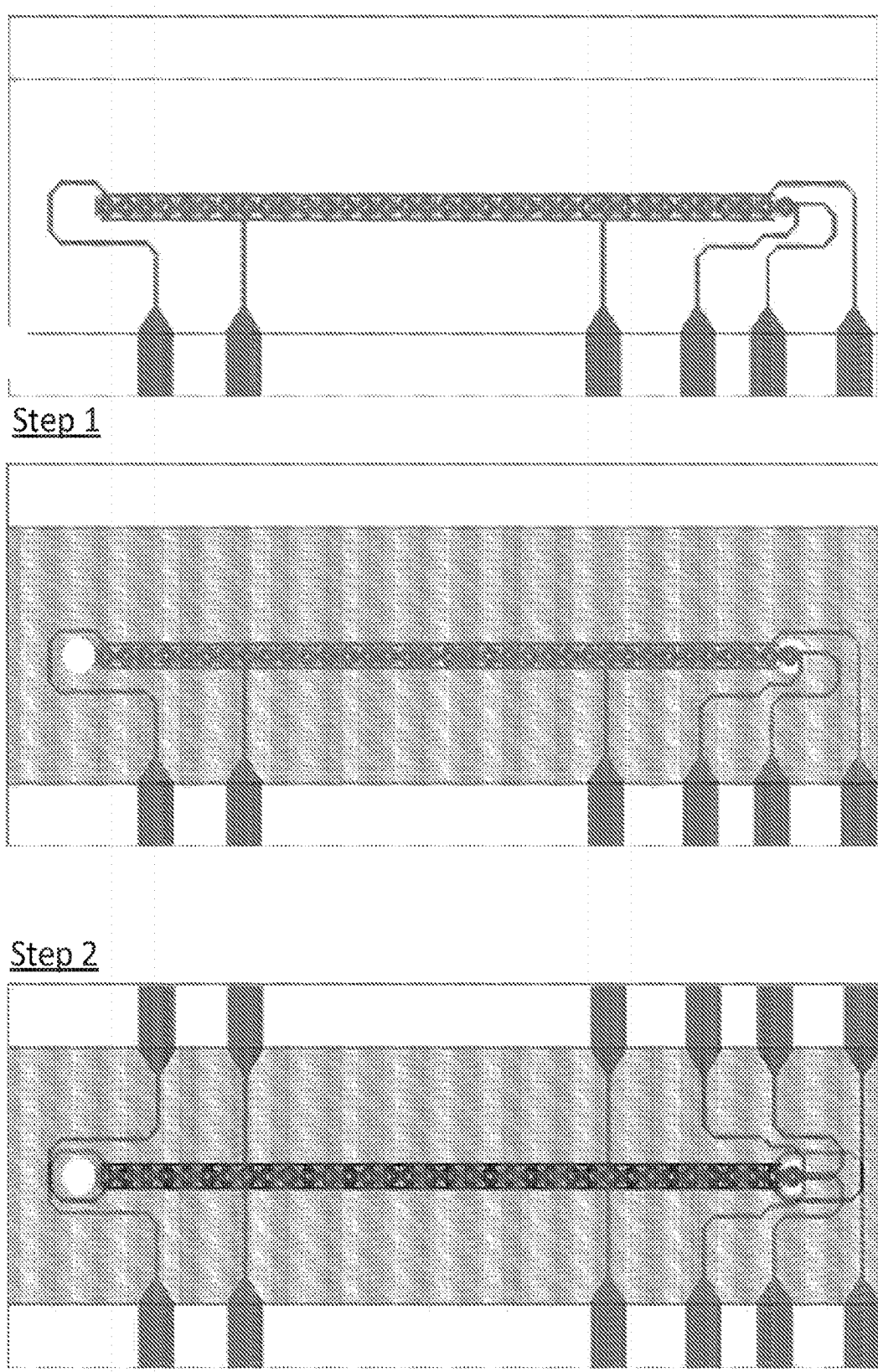
FIG. 12 illustrates steps in a process for assembly of two offset plates to allow easier access to contact pads for voltage application in accordance with some embodiments.

An aspect in some embodiments allows assembly of two offset plates to allow easier access to contact pads for voltage application (FIG. 12).

An aspect of some embodiments allows for analyte transport along the center of an electroosmotic trap. This aspect allows system the assembly with a pump in a backpressure configuration to limit contamination.

An aspect of some embodiments allows for plate fabrication with an electrode system and assembly using beads to provide adhesion between two plates and uniform spacing to maintain plate separation comparable to the depletion length.

An aspect of some embodiments allows for a closed loop system for purification of high ionic strength solutions. In this aspect, the device initially dilutes the sample to a complex permittivity suitable for analyte extraction and then adds salt and solid content to restore the sample or to remove excess water from the sample.

Figure 13:
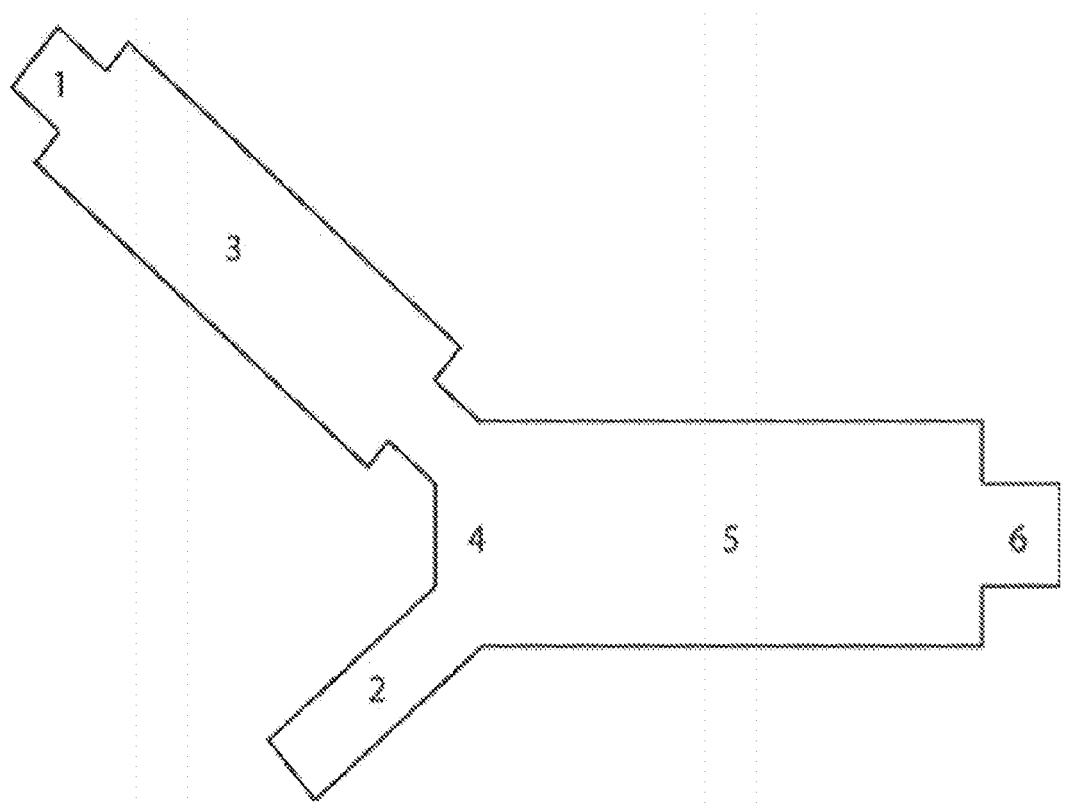
FIG. 13 illustrates a schematic view of a device for pretreatment of a reference solution or a low conductivity solution or water in accordance with some embodiments.

FIG. 13 shows a schematic view of a device for pretreatment of a reference solution or a low conductivity solution or water. The portions of the device are described as follows: (1) inlet for a reference solution or low conductivity solution or water; (2) inlet for sample solution; (3) chamber with electrode system which extracts contaminants from the reference solutions or low conductivity solution or water; (4) chamber for mixing the reference solutions or low conductivity solution or water with the sample solution; (5) chamber with electrode system for analyte or contaminant extraction from the solution present in chamber (5); (6) outlet.

FIG. 14 shows *E. coli* bacteria capture on an electrode system designed in accordance with some embodiments, where the *E. coli* have been captured using dielectrophoresis. The labeled portions of FIG. 14 are described as follows: (1) Electrode edge with captured *E. coli* bacteria; (2) Electrode edge with captured *E. coli* bacteria; (3) Depletion zone, also called the clearing zone. Beyond this zone bacterial are not captured within seconds of application of the electric field (bacteria within the depletion zone were captured on the electrodes with AC kinetic forces, while bacteria beyond the depletion zone remain unaffected by the AC kinetic forces); (4) Distance between electrodes chosen to match the effective length; (5) Length of the depletion zone measured as the distance between the edge of the electrode and the edge of the depletion zone.

Another aspect of some embodiments provides for detection of the presence of a bacteria, viruses, analyte, microscale components (e.g., bacteria) in a sample by monitoring the change in noise levels or change in noise spectrum of the detected signal between the baseline or control signal and the 'contact state', where the bacteria, viruses, analyte, microscale components is in contact or close proximity to the sensor. The sensor surface can, but does not have to be chemically coated, to be sensitive to a particular bacteria, viruses, analyte, microscale components or family of bacteria, viruses, analyte, microscale components.

Figure 15A:
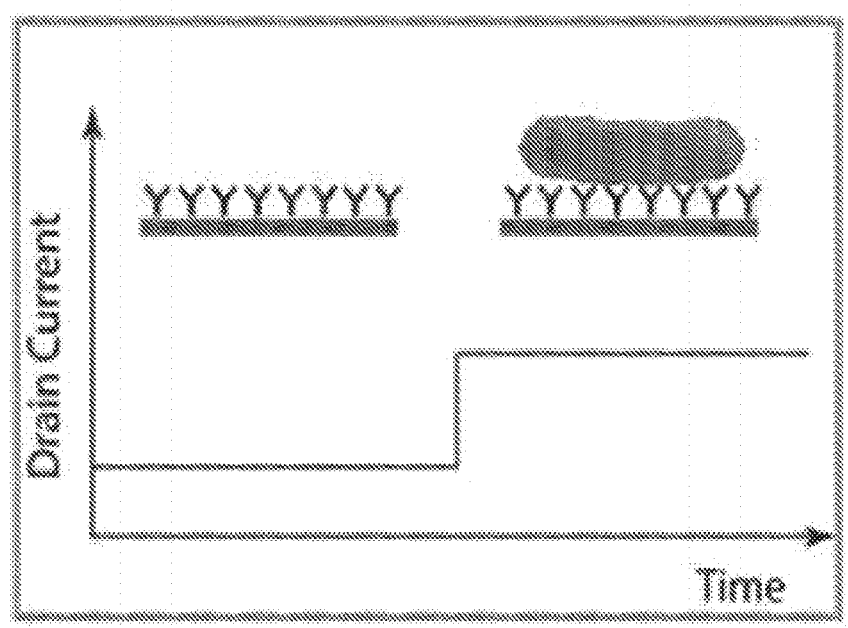
FIG. 15A shows a schematic overview of bacterial detection with a sensing system in accordance with some embodiments.

FIG. 15A shows a schematic overview of bacterial detection with the sensing system. The sensor surface is covered with molecular recognition elements (anti-*E. coli* antibodies). When a bacterium comes in contact with the surface, the interaction between a bacterium and the sensor surface causes a change in current.

Figure 15B:
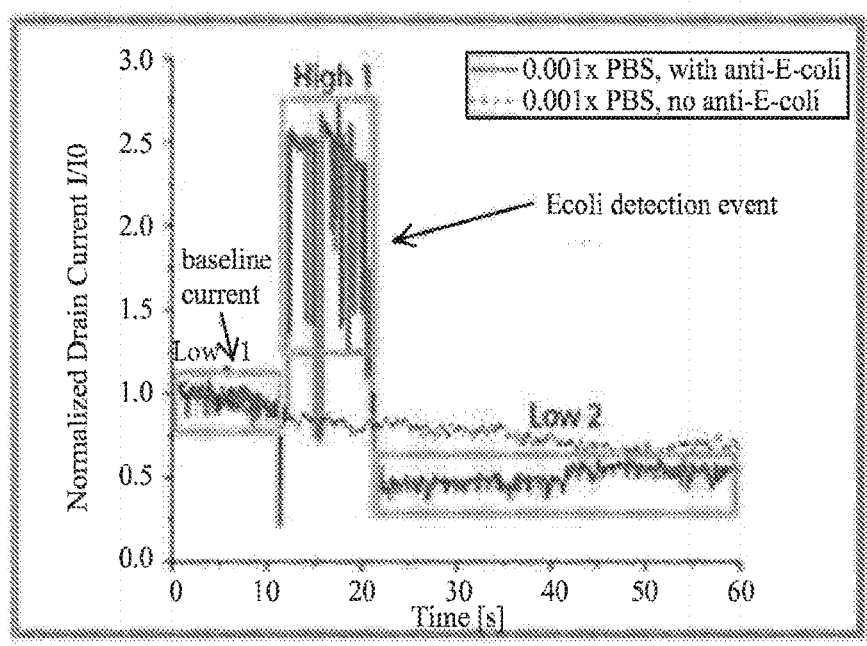
FIGS. 15B-D show that the current in a sensor changes upon a bacterium coming in contact with the sensor surface and that the noise level changes upon bacterial binding, in accordance with some embodiments.
Figure 15C:
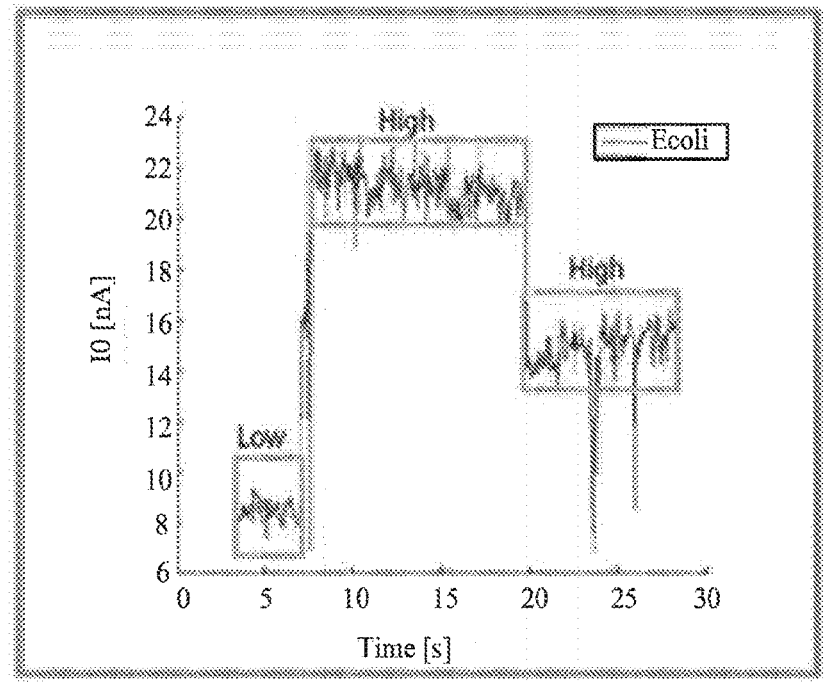
Figure 15D:
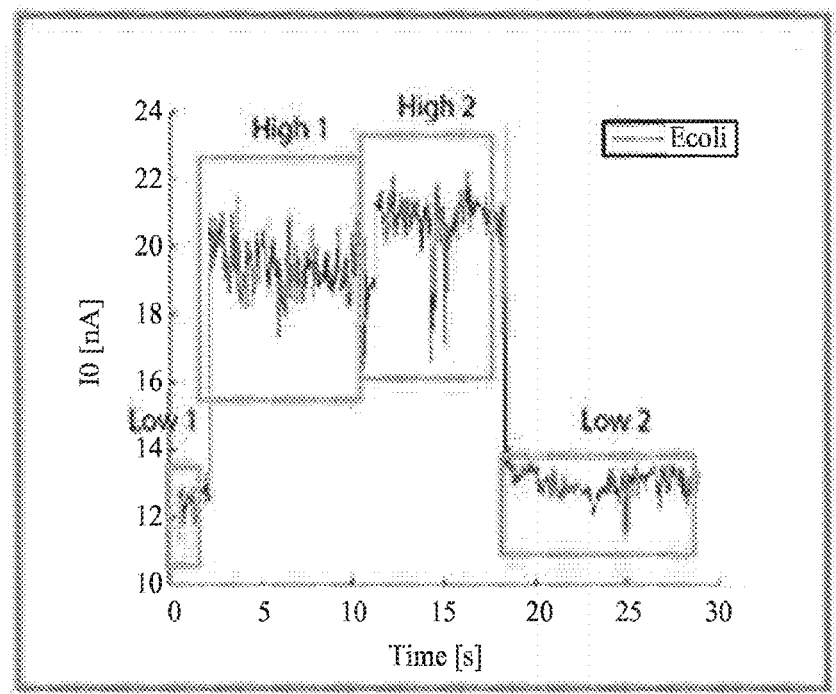

FIGS. 15B-D show that the current in the sensor changes upon a bacterium coming in contact with the sensor surface. The noise level of the current before and after a bacterial binding and detection event is much lower (noise Low) than during the binding event (noise High).

Some embodiments are directed to a spectrometer that uses DEP (positive or negative) and EO detect and/or identify analytes in a solution without having to label sensors in the detection array. Such a spectrometer may also be used to determine CM factor curves for different analytes that collectively form an analyte "fingerprint" library, which may further be used to identify particular analytes, as discussed in more detail below.

Spectrometer for CM Factor Determination

Some embodiments are directed to bacterial detection and identification using a three frequency method (decryption) of two frequencies with repetition or a frequency switch. Examples of such frequency switching techniques are described in more detail below.

Accurate and time effective detection of low levels of bacteria present in liquid samples is challenging. Advancements in sensor resolution and macro optics allow modern cameras to have a pixel resolution on the order of a single bacterium size (e.g., in the 2-10 μm range). However, optical detection technologies typically require sample preparation and have a high false negative rate.

In addition to the techniques described above, U.S. Patent Publication No. 2015/0107999 and U.S. Pat. No. 9,120,105, the entireties of each of which are incorporated by reference herein, describe techniques for separating and capture bacteria from solution. In order to detect and identify specific bacteria, antibody binding was used to further segment the bacteria. Some antibodies, however, are not precisely targetable, may not be commercially available for many bacterial vectors and may be difficult to integrate in manufacturing. Thus, relying on antibodies to provide specificity of detection may limit the practical and commercial potential of some systems for some applications.

Some embodiments described herein relate to a technique for identifying bacterial contamination without the use of antibodies or other molecular recognition elements. This technique allows for detection and identification of a unique signature or "fingerprint" of an analyte in a given solution.

Some embodiments described herein relate to a technique for detecting and identifying bacteria using dielectrophoresis (DEP) and electroosmosis (EO). Validation data to support the concepts in described technique are also discussed.

Figure 19:
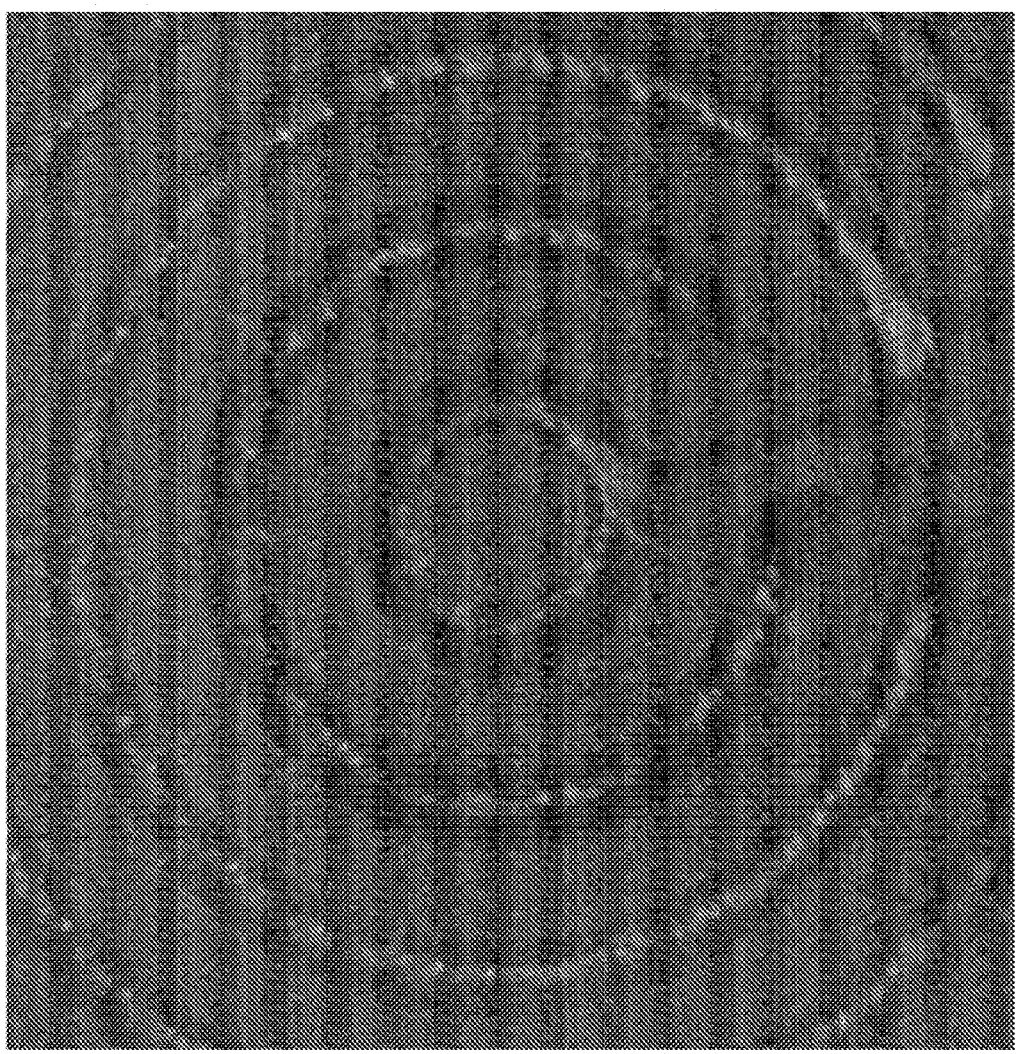
FIG. 19 illustrates bacteria in an electroosmotic trap in accordance with some embodiments.

Neither dielectrophoresis nor AC kinetics has been typically used for bacterial identification. Electroosmosis traps bacteria in the center of an electroosmotic trap, which is close to the center of an electrode. In an electroosmosis trap, bacteria hover above the electrode surface oriented vertically over the electrode. FIG. 19 shows bacteria in an electroosmotic trap, which is at the center of the electrode at FEO(f1)=10 kHz. FEO(f1) is the frequency of the electric field E(V,f) at which bacteria are trapped in an electroosmosis trap. The frequency range under which electroosmosis trapping occurs may vary for different species.

Figure 20:
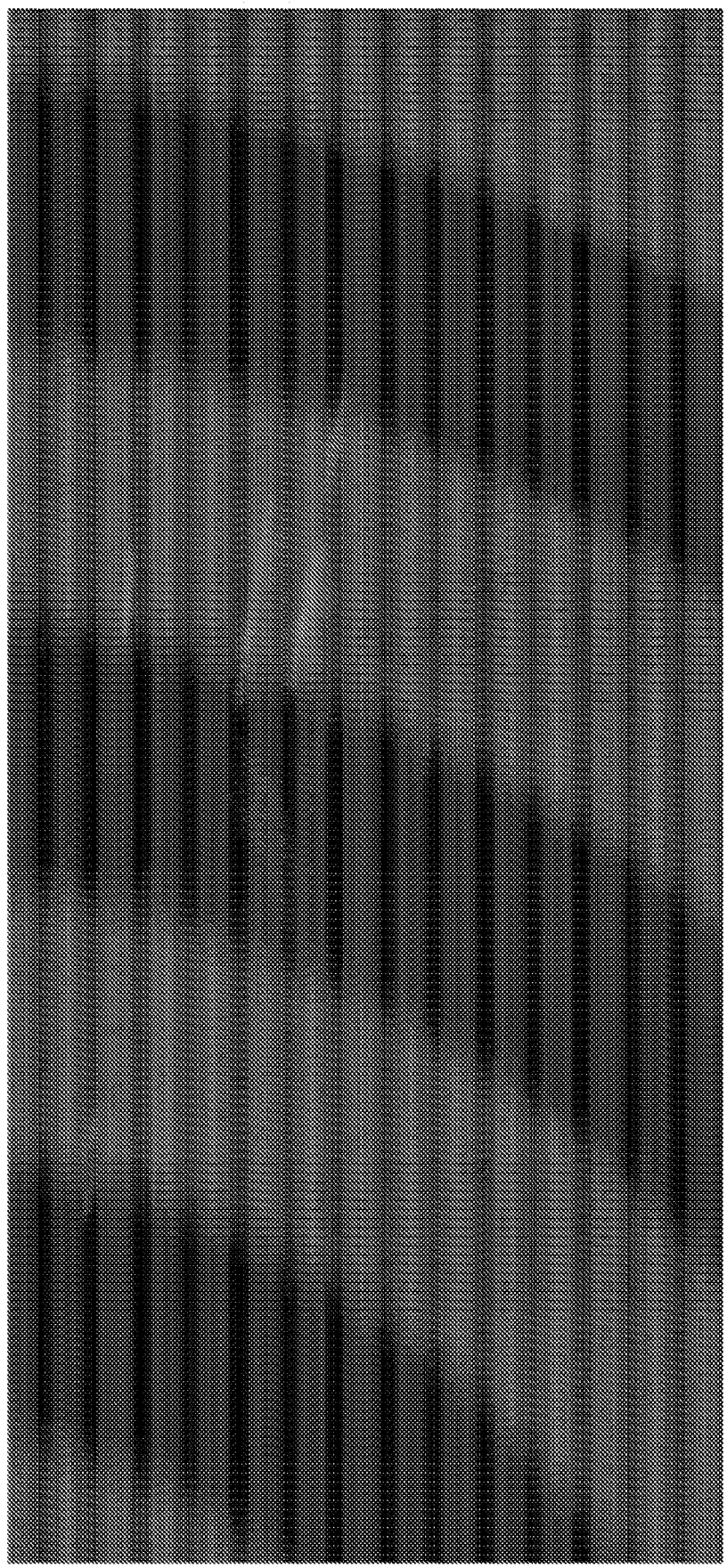
FIG. 20 illustrates a horizontal alignment of bacteria in contact with the electrode edge using dielectrophoresis in accordance with some embodiments.

Dielectrophoresis traps bacteria on the edges of electrodes with the orientation of the long axes of the bacteria being parallel to the electrode surface, where the short side is in contact with the electrode edge and the long side stretches away from the electrode or tangentially to the electrode edge. FIG. 20 illustrates the horizontal alignment of bacteria in contact with the electrode edge using dielectrophoresis. FDEP(f2) is the frequency at which bacteria are trapped in a dielectrophoresis trap. An electric field having a frequency of 10 MHz and a 10V peak-to-peak voltage was used to generate the image shown in FIG. 20. The frequency range under which dielectrophoresis trapping occurs may vary for different species.

By knowing the frequency (FEO(f1)) of the electric field that the analyte is trapped in an electroosmosis trap and the frequency (FDEP(f2)) of the electric field that the analyte is trapped in a dielectrophoresis trap, in some embodiments it is possible to switch between these frequencies, e.g., apply an electric field with amplitude V1 and frequency FEO(f1) for t1 seconds, then apply an electric field with amplitude V2 and frequency FDEP(f2) for t2 seconds, then again apply an electric field with amplitude V1 and frequency FEO(f1) for t1 seconds. In such a scenario, Fswitch may be defined as the frequency at which switching between FEO(f1) and FDEP(f2) occurs.

Figure 21:
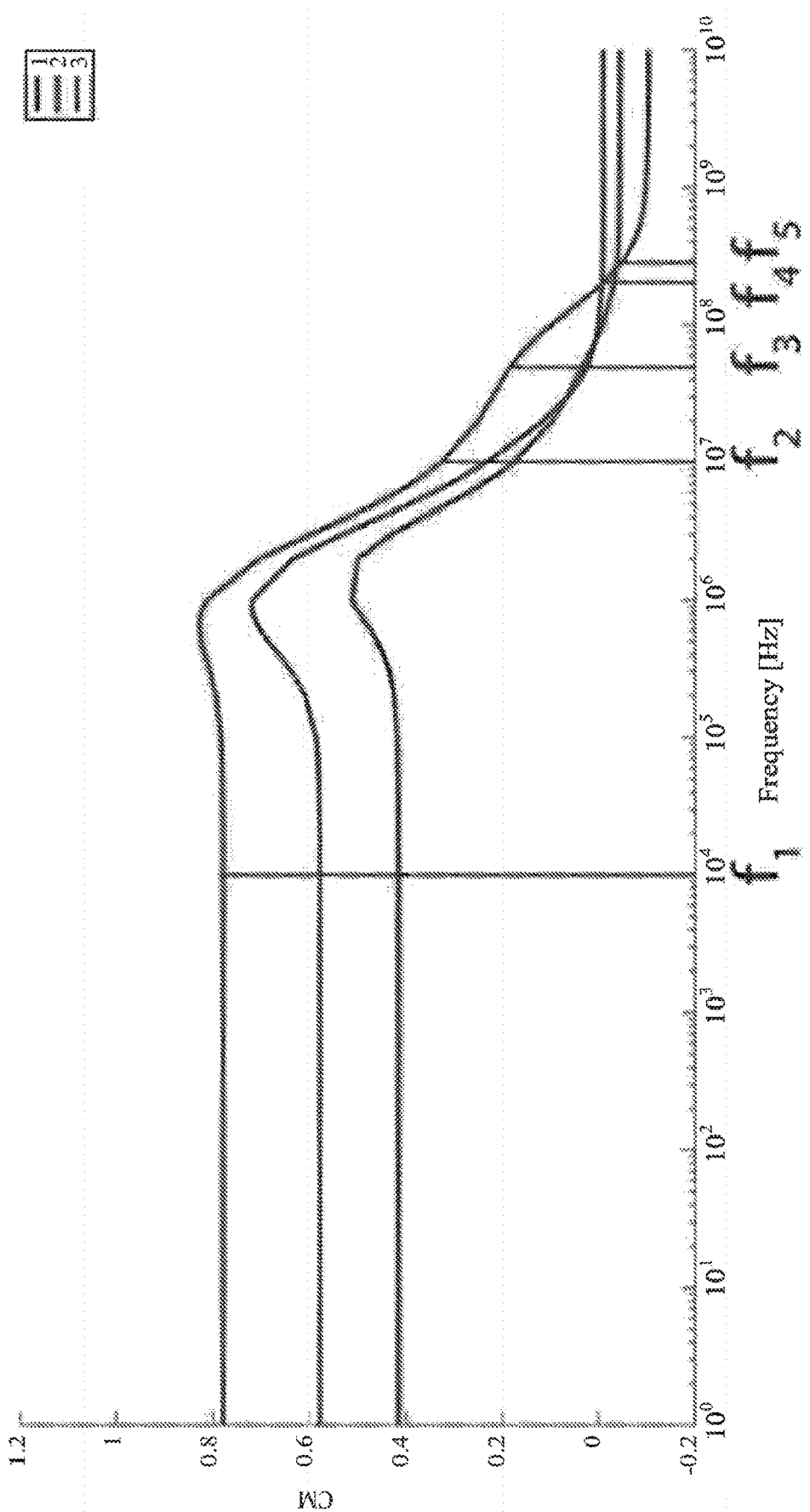
FIG. 21 illustrates a plot of a bacterial CM factor and its dependence on frequency for three different sets of parameters in accordance with some embodiments.

FIG. 21 shows a plot of a bacterial CM factor and its dependence on frequency for three different sets of parameters. The CM factor calculation followed the 3 shell Castellarnau method and used the following parameters: solution_conductivity=0.0015 S/m; b=a/2; d2=8*1e−9 m; d3=50*1e−9 m;

Set 1: a=0.5*1e−6 m; sigma(1)=0.48; sigma(2)=259*1e−6; sigma(3)=58*1e-3, eps(1)=49.8; eps(2)=9.8; eps(3)=78;

Set 2: a=2.0*1e−6 m; sigma(1)=0.48/2; sigma(2)=259*1e−6; sigma(3)=58*1e−3; eps(1)=80; eps(2)=9.8; eps(3)=78;

Set 3: a=5.0*1e−6 m; sigma(1,p)=0.48*2; sigma(2,p)=259*1e−6; sigma(3,p)=58*1e−3; eps(1,p)=25; eps(2,p)= 9.8; eps(3,p)=78.

Figure 56:
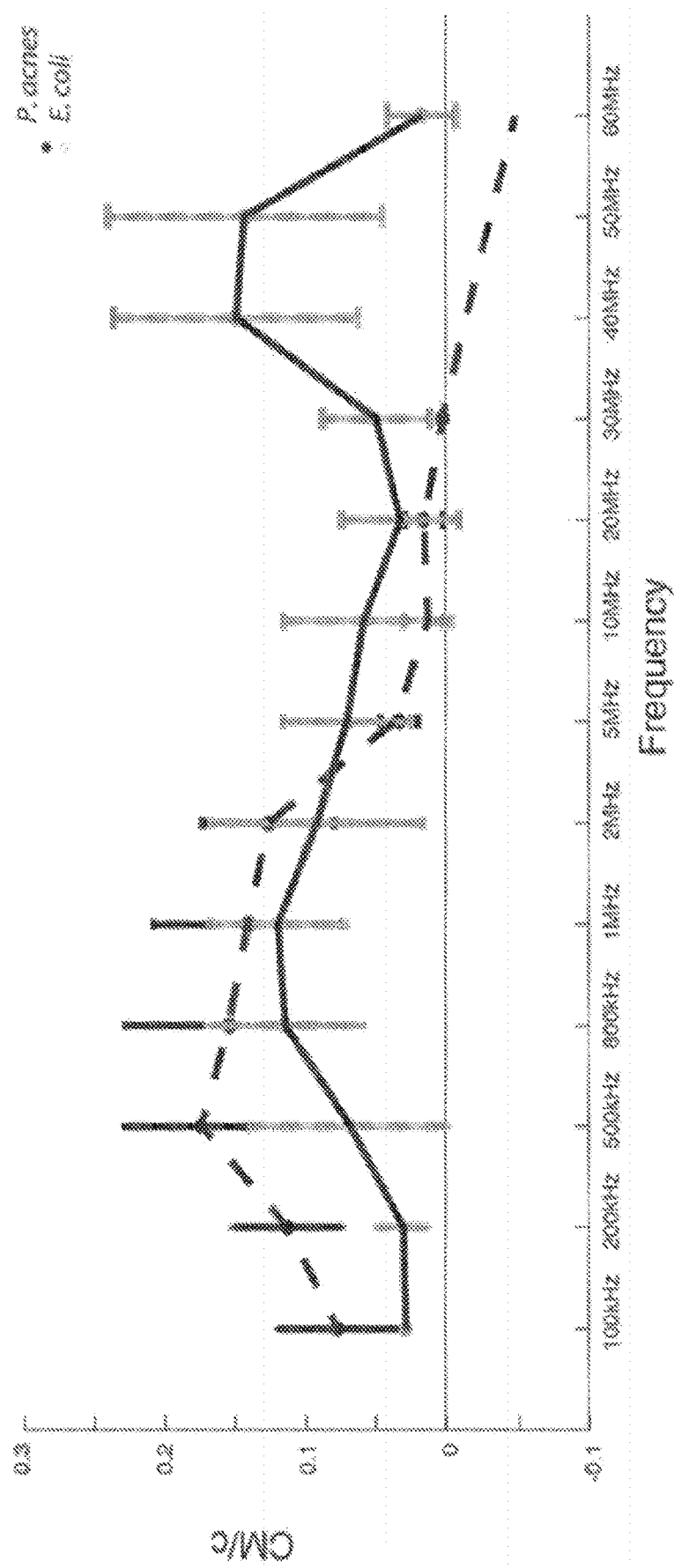
FIG. 56 shows a calculated CM/c factor in accordance with some embodiments.

FIG. 56 shows the CM/c factor calculated from data, where c is a spectrometer dependent constant. The CM/c plot was calculated for *E. coli* and *P. acnes* from the measured bacterial motion trajectories, when bacteria moved between trapping centers. The plot indicates differential response of both bacterial species at 30 MHz. *E. coli* bacteria show negative values of the CM factor at frequencies above 60 MHz, while for *P. acnes*, the cross over frequency is around 30 MHz.

As shown in FIG. 21, the CM factor at each of the operating frequencies (f1, . . . f5) is sufficiently different for the different parameter sets to cause differences in the dielectrophoresis force and as a result, differences in the time it takes bacteria or another analyte to respond to the change of the electric field $t_{tr1}$.

Electroosmosis depends on the particle size, whereas the dielectrophoresis force is proportional to the cube of the particle size and the CM factor. Conventional techniques for detecting bacteria require growing detectable colonies (e.g., at least 100 bacteria) that can then be imaged. Moving bacteria between two different positions—the intra-electrode center of the electroosmotic trap (using EO trapping) and the outer-electrode to electrode edge center of the PDEP trap (using positive DEP 'PDEP' trapping) by switching between different electric field frequencies, in accordance with some embodiments, results in localized noise at the point of bacterial presence and static signal in all other spots. The noise signature and/or picture quality can be compared across imaged frames to indirectly detect the presence of bacteria without the need to grow the bacteria into colonies. For example, in one aspect, only non-specific staining or autofluorescence may be used to obtain a visual confirmation of the presence of bacteria.

In some embodiments, a frequency spectrum for FEO f1(f) and FDEP f2(f) is scanned by measuring the noise activity and electric or optical response as a function of frequency. The spectrum has a unique signature for different analyte groups.

Additionally, in one aspect, the known switching frequency Fswitch may act as a carrier wave for a lock-in amplifier for additional signal enhancement and noise filtration.

Figure 22:
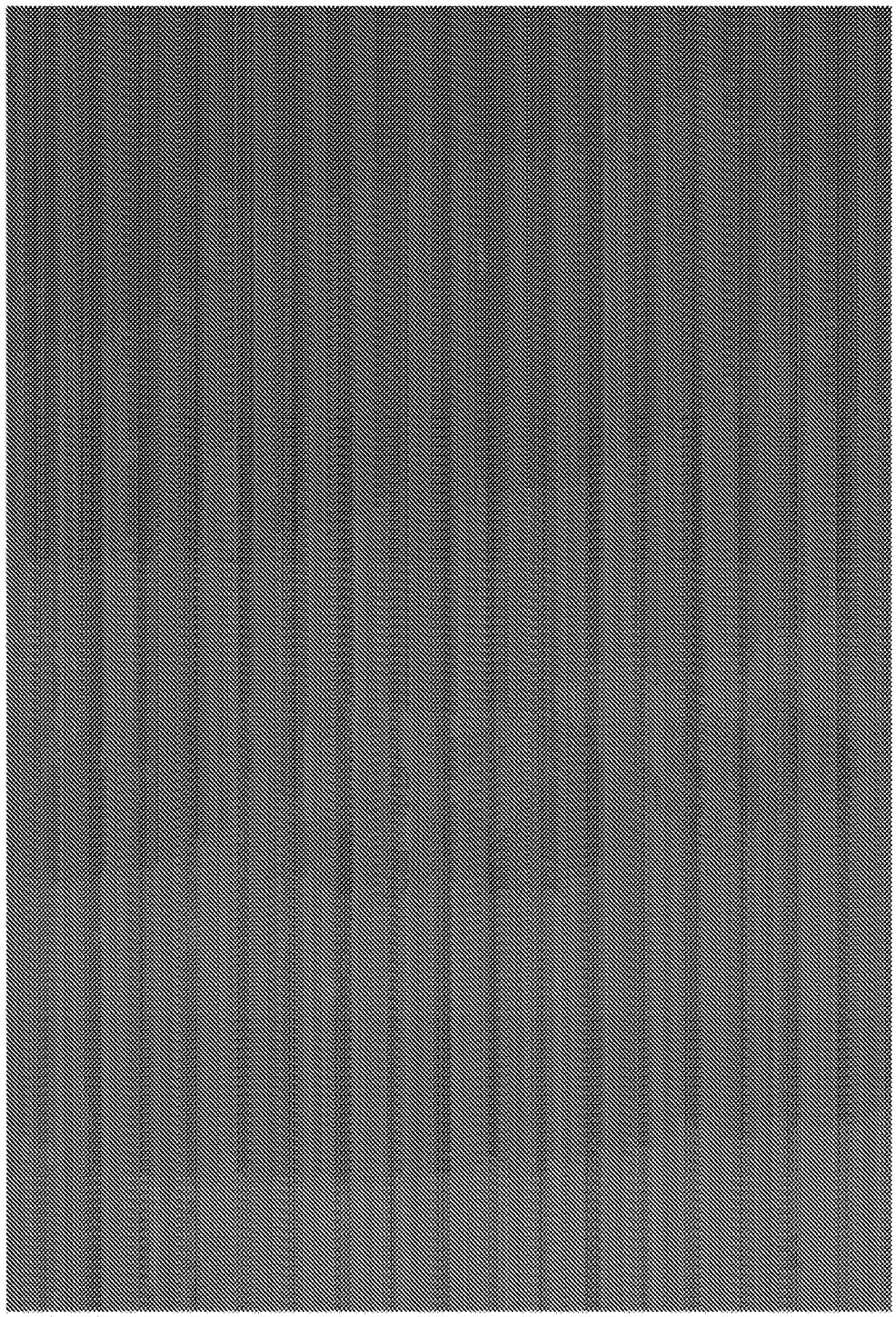
FIG. 22 illustrates bacterial horizontal alignment in contact with an electrode edge in accordance with some embodiments.
Figure 23:
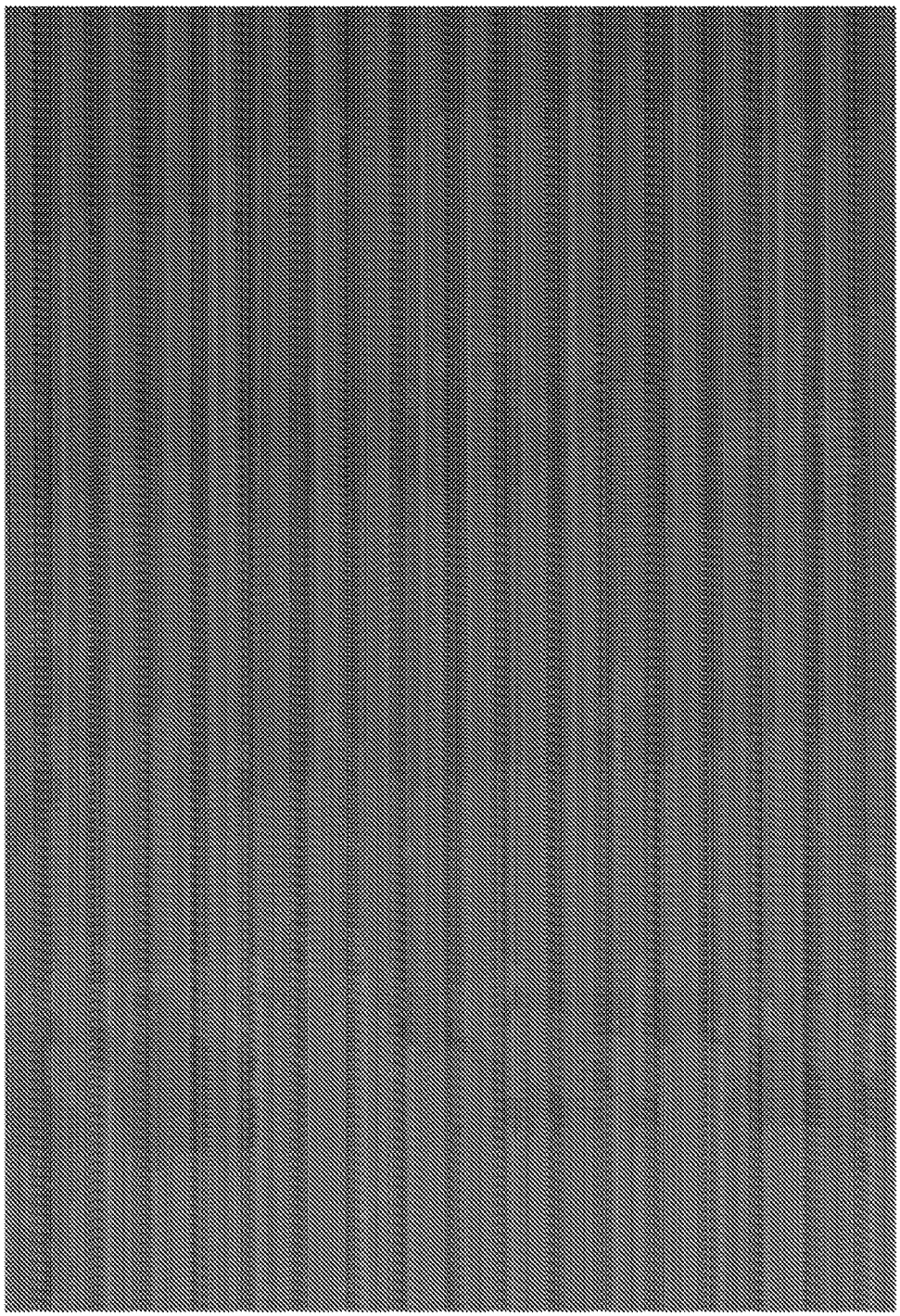
FIG. 23 shows no alignment of bacteria with an electrode edge in the absence of an electric field in accordance with some embodiments.
Figure 24:
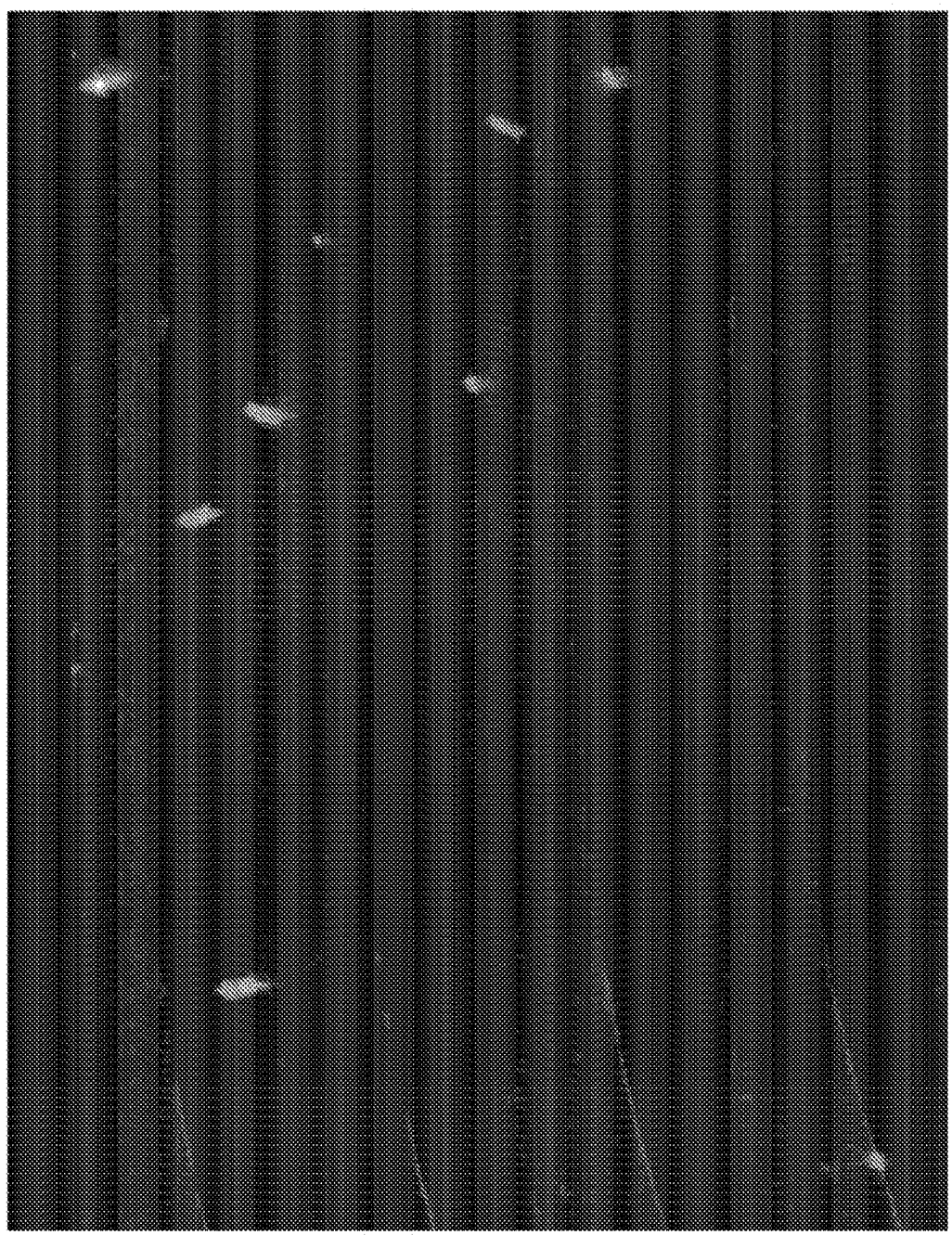
FIG. 24 shows that an initial random distribution is not correlated with electrode geometry in the absence of an electric field in accordance with some embodiments.

FIGS. 22-34 show bacterial position with respect to the electrodes in EO and positive DEP trap capture. FIG. 22 shows bacterial horizontal alignment in contact with an electrode edge. FIG. 23 shows no alignment of bacteria with an electrode edge in the absence of an electric field. FIG. 24 shows that an initial random distribution is not correlated with electrode geometry in the absence of an electric field.

Figure 25:
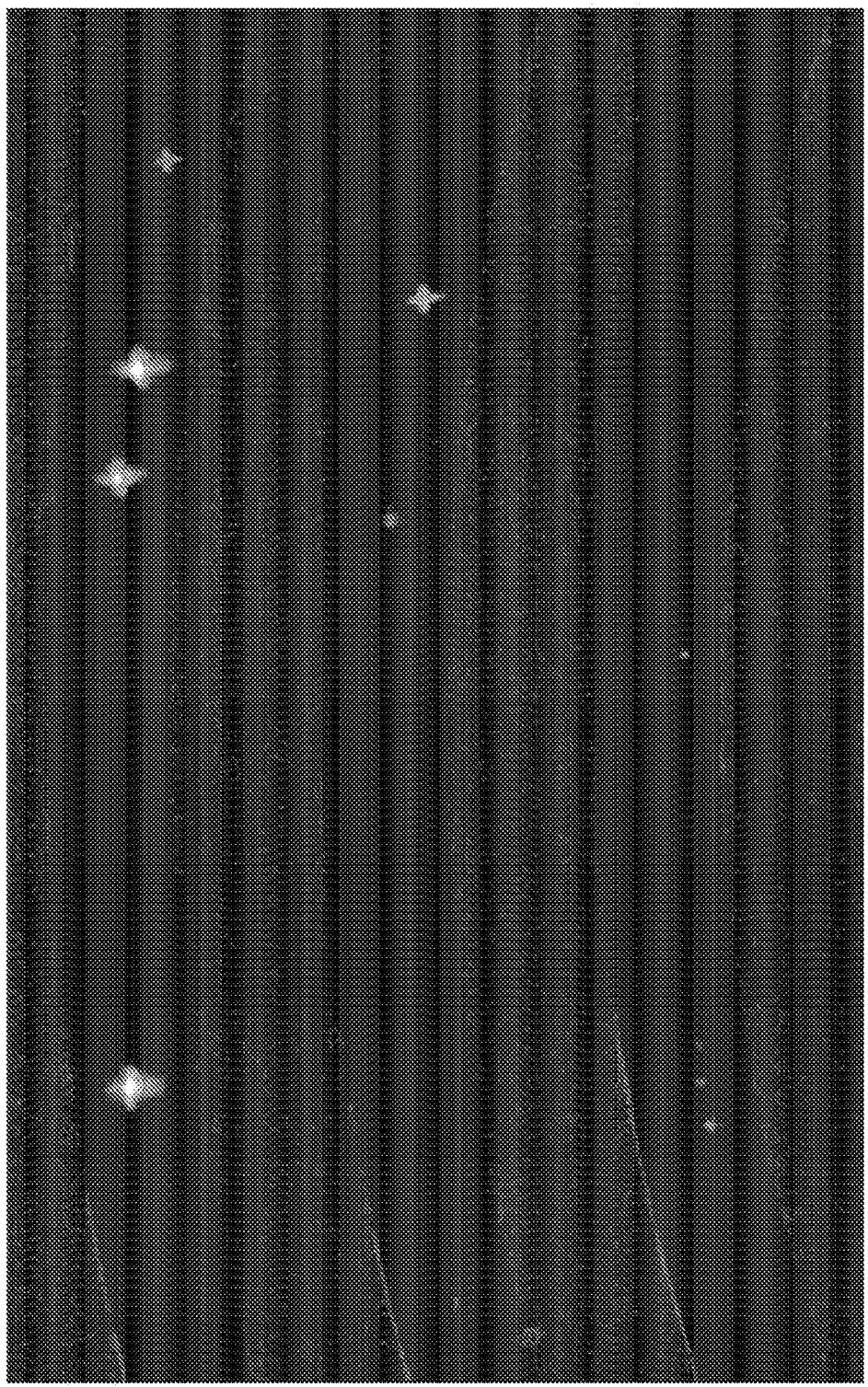
FIG. 25 shows vertical alignment of bacteria above the electrode surface in the presence of a 10 kHz electric field in accordance with some embodiments.
Figure 26:
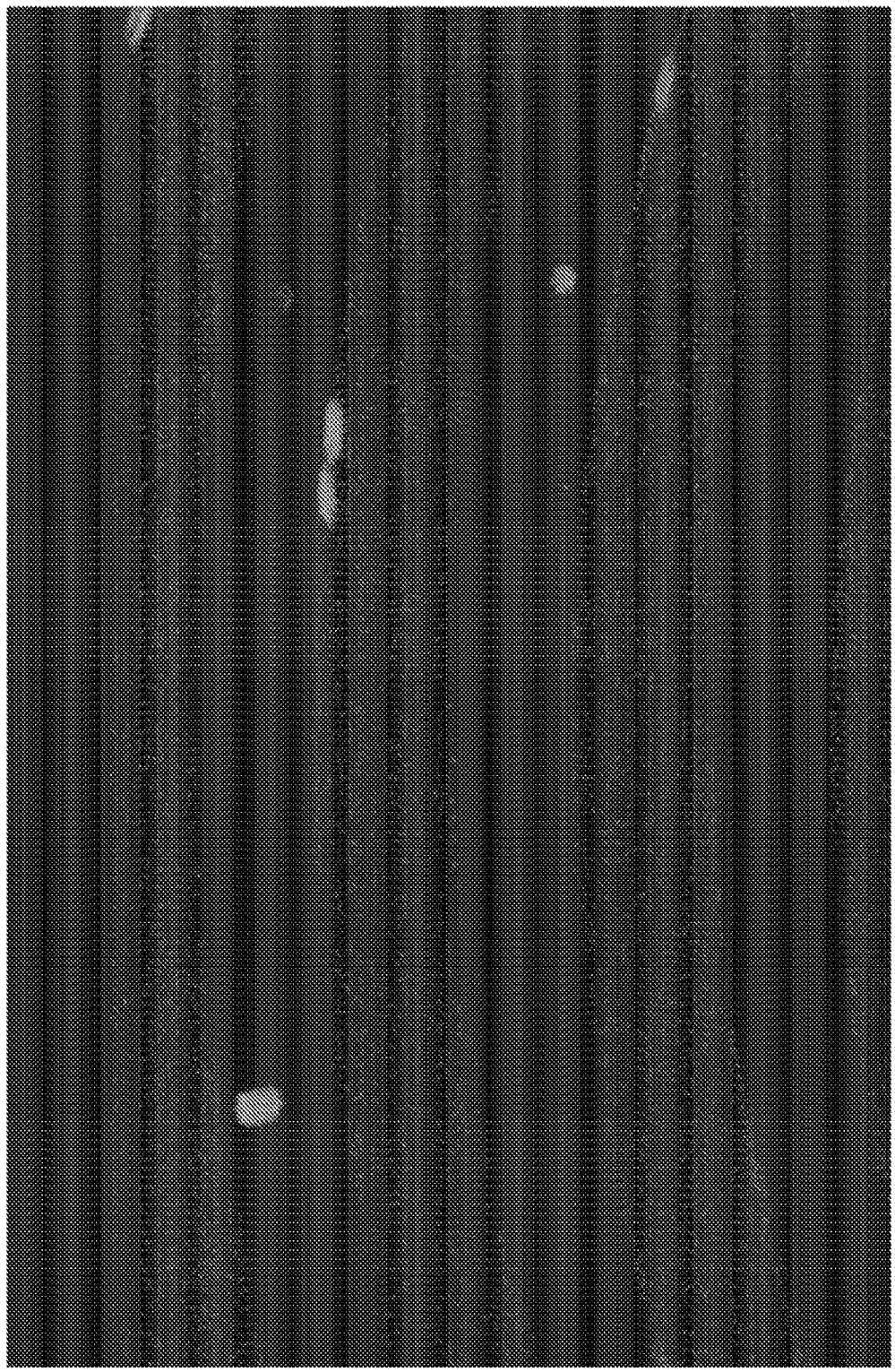
FIG. 26 shows horizontal alignment of bacteria in the electrode plane in the presence of a 10 MHz electric field in accordance with some embodiments.
Figure 27:
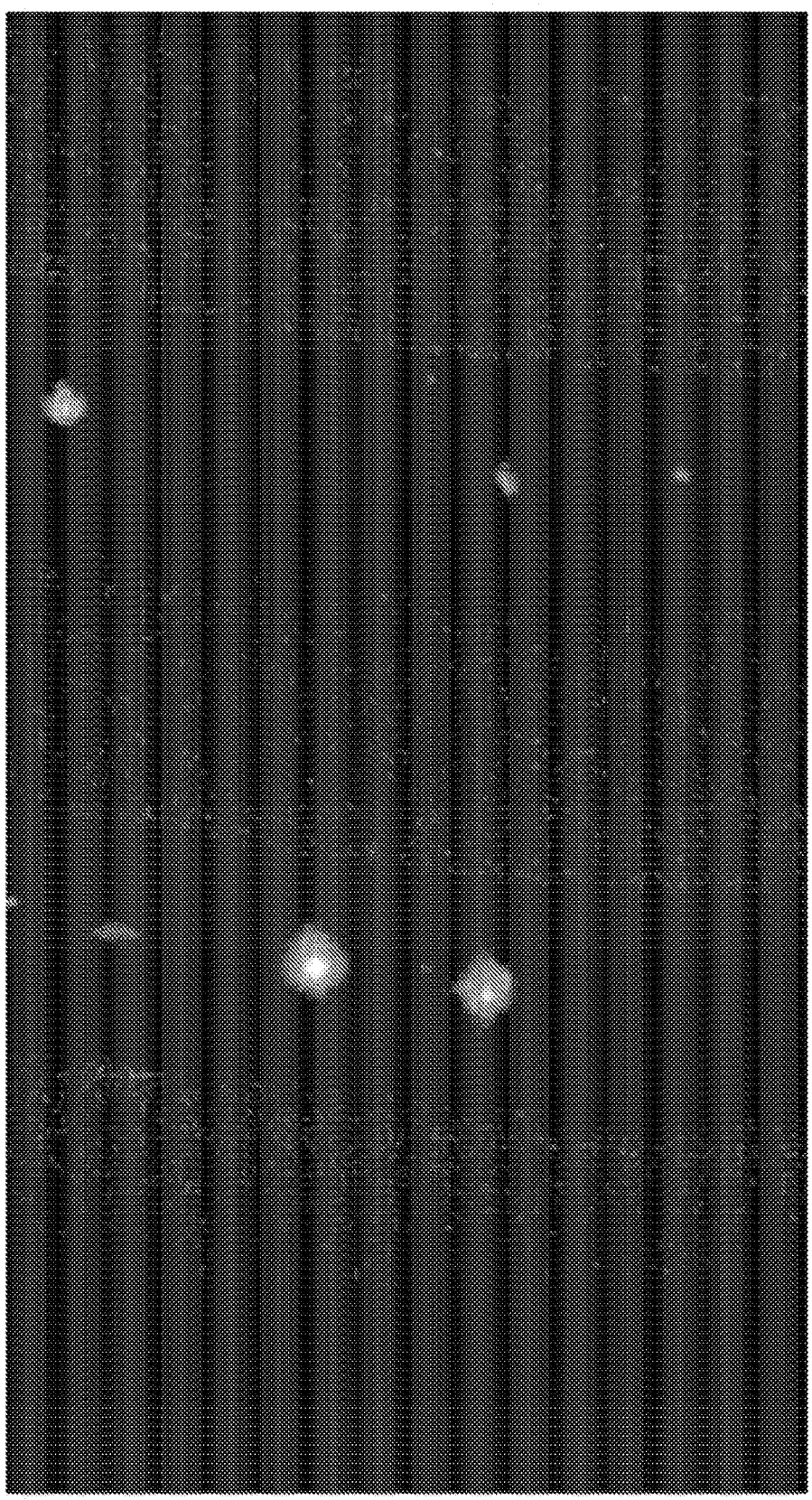
FIG. 27 shows vertical alignment of bacteria above the electrode surface in the presence of a 10 kHz electric field in accordance with some embodiments.
Figure 28:
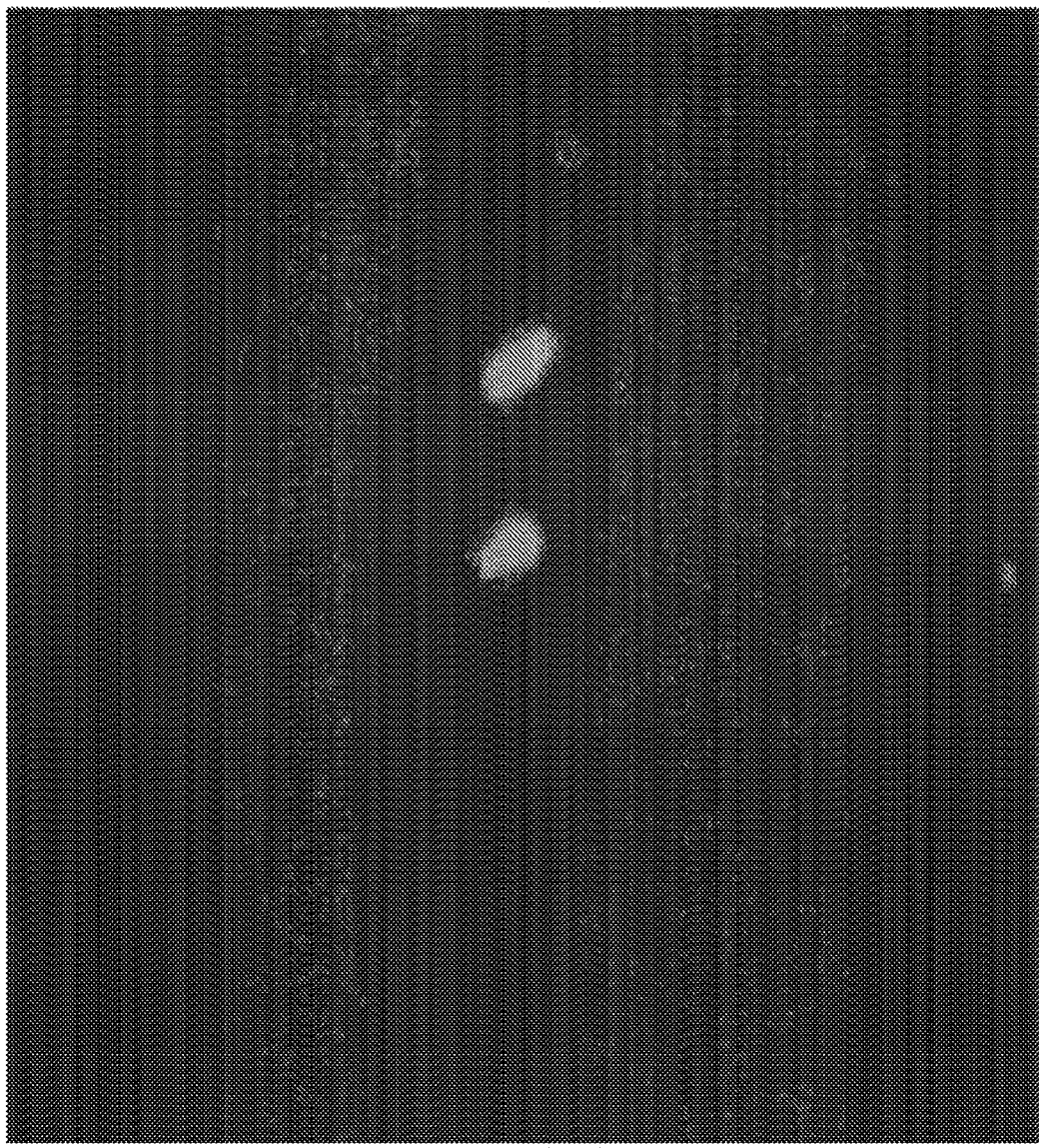
FIG. 28 shows horizontal alignment of bacteria in the electrode plane in the presence of a 10 MHz electric field in accordance with some embodiments.
Figure 29:
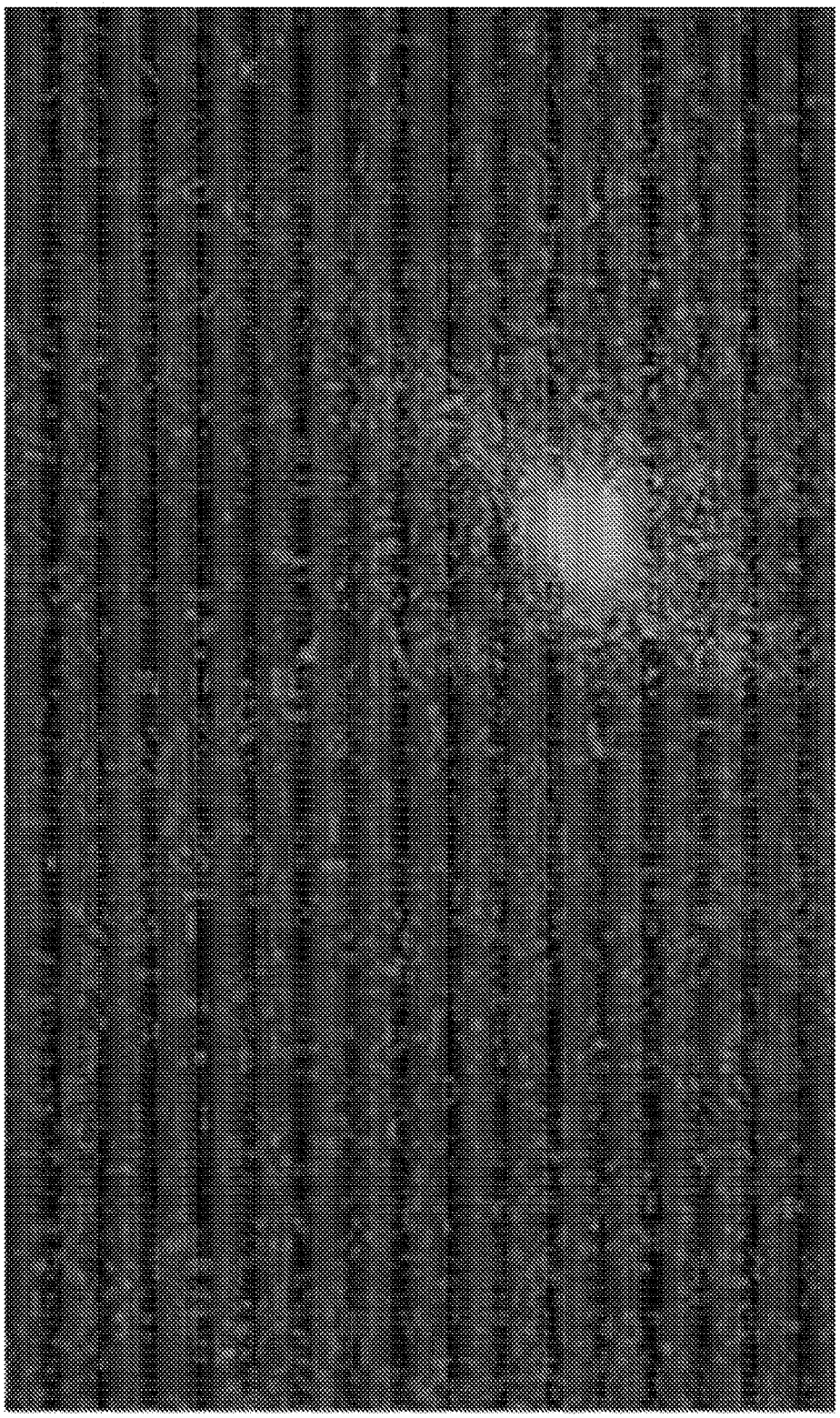
FIG. 29 shows vertical alignment of bacteria above the electrode surface in the presence of a 10 kHz electric field in accordance with some embodiments.
Figure 30:
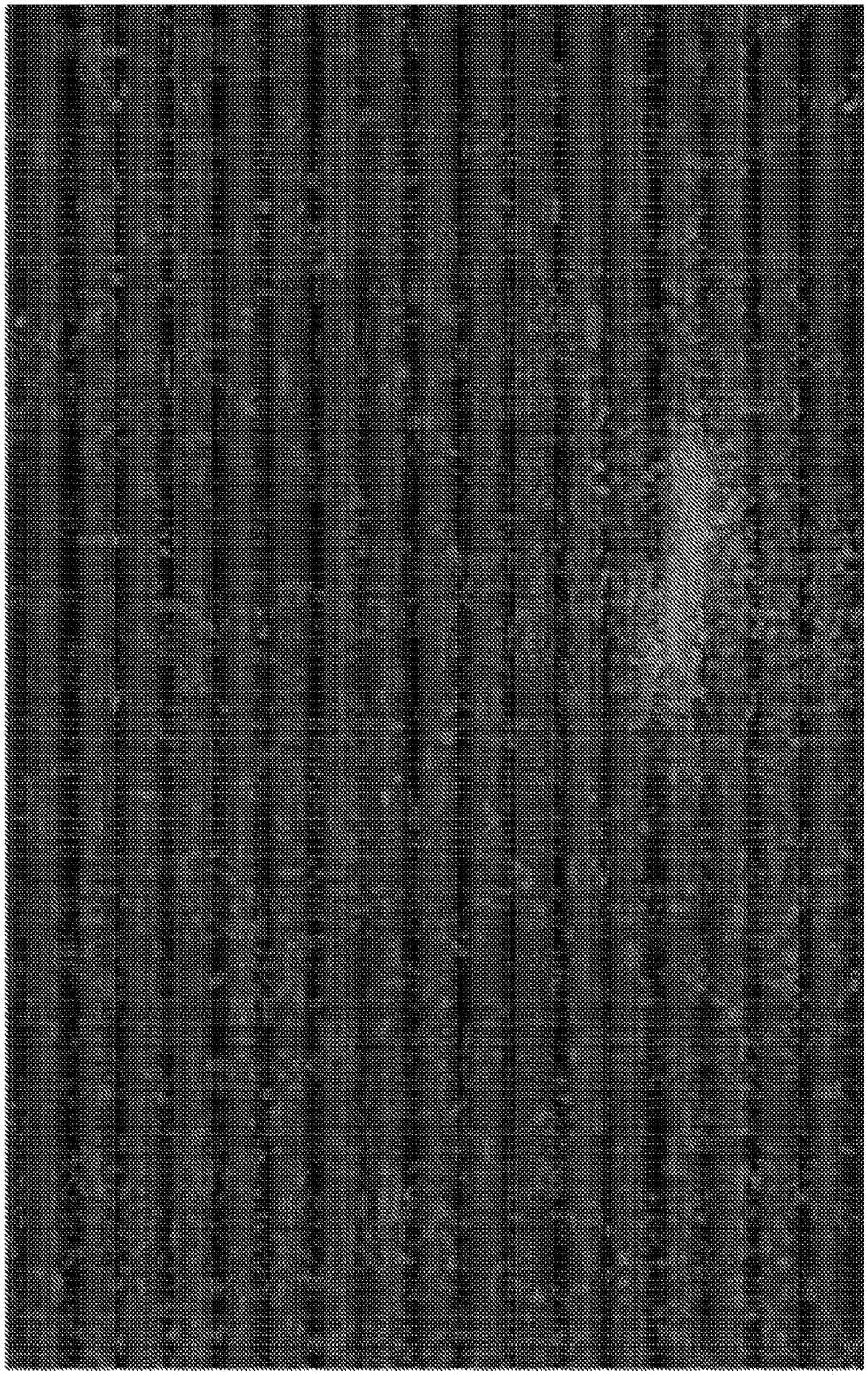
FIGS. 30-33 show horizontal alignment of bacteria in the electrode plane in the presence of a 10 MHz electric field in accordance with some embodiments.
Figure 31:
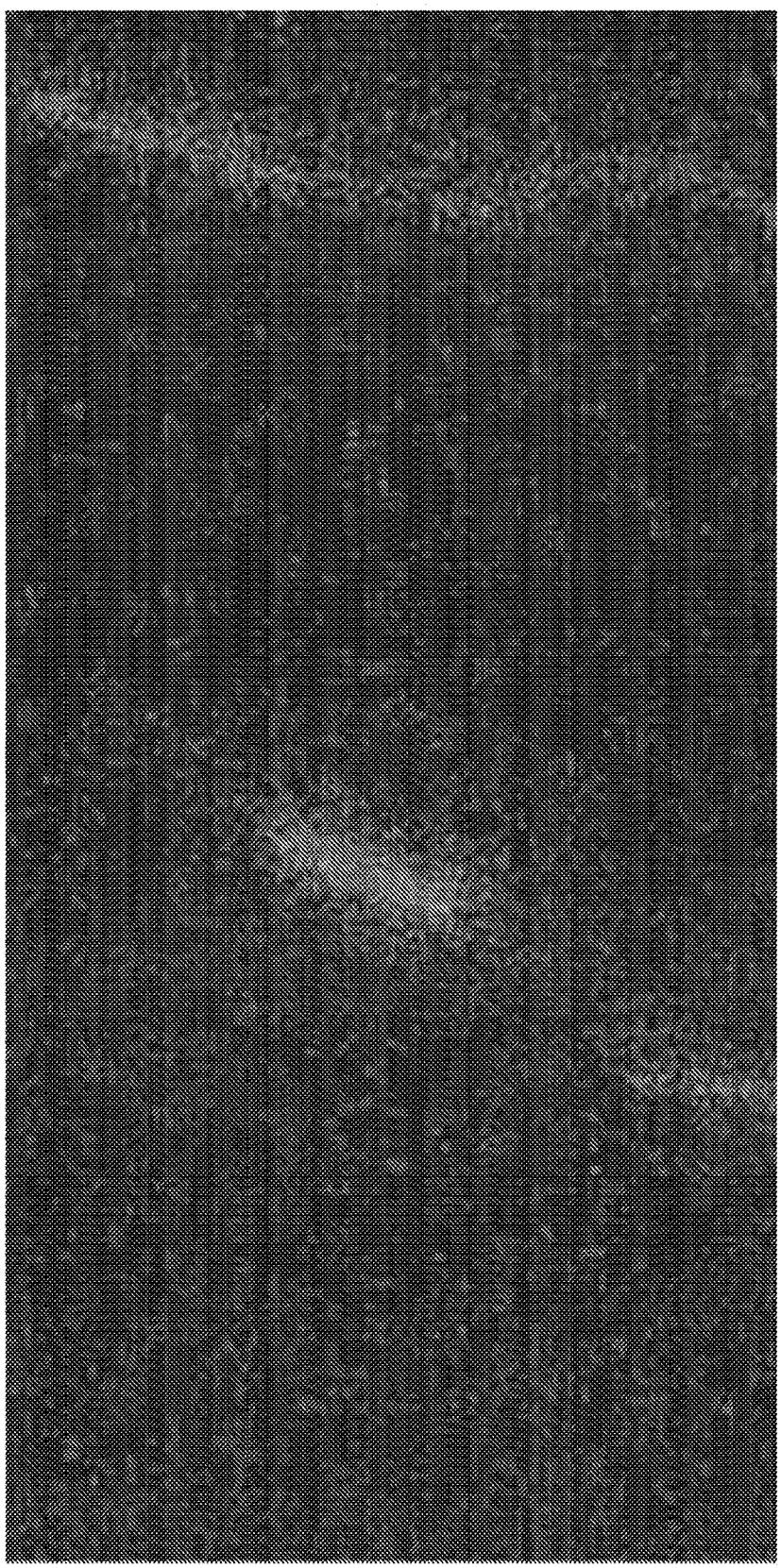
Figure 32:
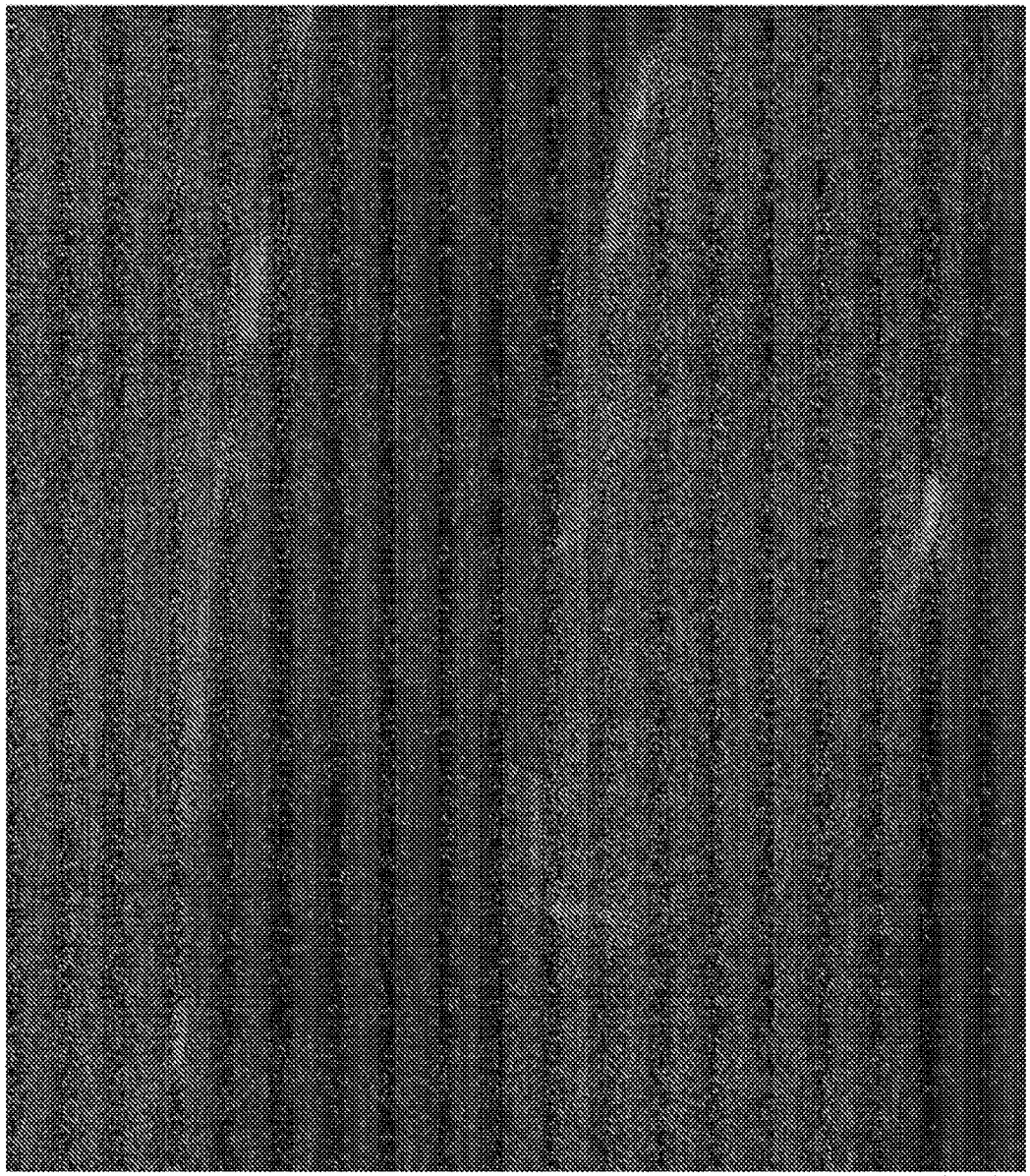
Figure 33:
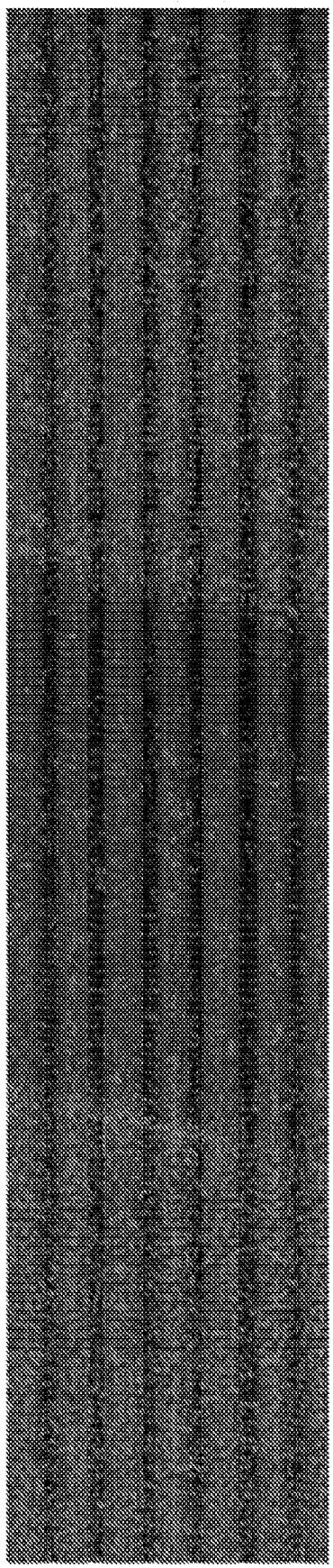
Figure 34:
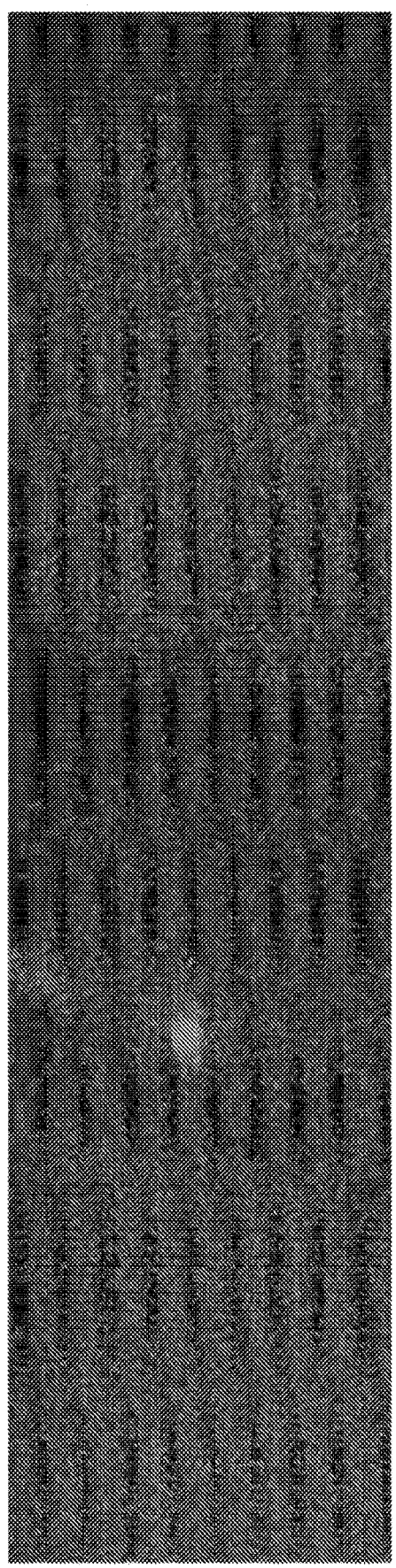
FIG. 34 shows vertical alignment of bacteria above the electrode surface in the presence of a 10 kHz electric field in accordance with some embodiments.

FIG. 25 shows vertical alignment of bacteria above the electrode surface in the presence of a 10 kHz electric field.
FIG. 26 shows horizontal alignment of bacteria in the electrode plane in the presence of a 10 MHz electric field.
FIG. 27 shows vertical alignment of bacteria above the electrode surface in the presence of a 10 kHz electric field.
FIG. 28 shows horizontal alignment of bacteria in the electrode plane in the presence of a 10 MHz electric field.
FIG. 29 shows vertical alignment of bacteria above the electrode surface in the presence of a 10 kHz electric field.
FIGS. 30-33 show horizontal alignment of bacteria in the electrode plane in the presence of a 10 MHz electric field.
FIG. 34 shows vertical alignment of bacteria above the electrode surface in the presence of a 10 kHz electric field.

Figure 35A:
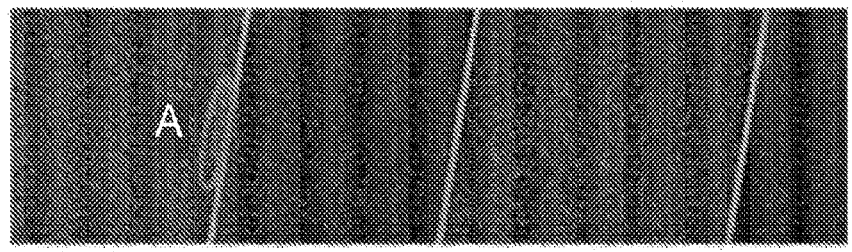
FIGS. 35A-G show examples of switching an electric field frequency in accordance with some embodiments.
Figure 35B:
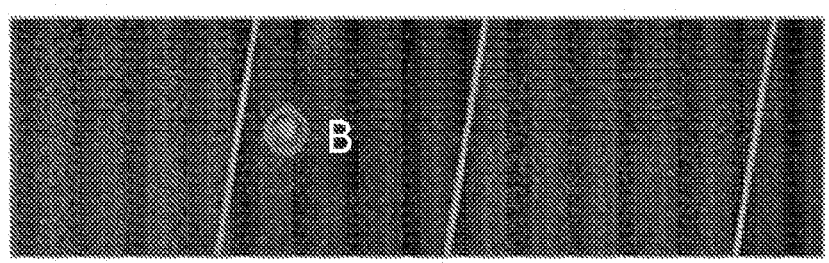

FIGS. 35A-G shows an example of switching an electric field frequency in accordance with some embodiments. FIG. 35A shows bacterium captured on the edge of an electrode in a PDEP trap at 10 MHz, at initial time t1=0 sec. As shown in the timing diagram of FIG. 35D, an electric field having a frequency FDEP(f2) is initially applied for time duration t1 to capture the bacterium. The frequency of the electric field is then switched from FDEP(f2) to FEO(f1) for a duration t2. FIG. 35B shows bacterium captured in an EO trap at 10 kHz, at time t2=2 sec when the electric field frequency is switched from 10 MHz to 10 kHz. It takes the bacterium a time $t_{tr1}$ to respond to the change of the electric field and to move from position A on the edge of the electrode as shown in FIG. 35A to position B at the center of the electrode (or a position inside of the electrode space) as shown in FIG. 35B. For the remainder of the time t2 when the electric field having a frequency FEO(f2) is applied, the bacterium is captured in the electroosmotic trap at position B. The electroosmotic trap allows bacteria to move along the lines or surfaces of the electroosmotic trap, thus the position B may change in space within the trap. Similarly for the dielectrophoresis trap, even though the confinement in space is stronger than for the electroosmotic trap, the bacterium may still change position.

Figure 35C:
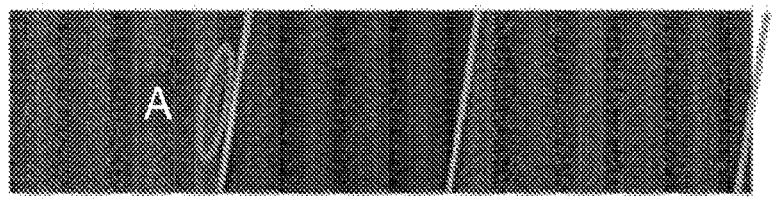

Following the duration t2, the electric field frequency is switched from FEO(f1) to FDEP(f2n), where f2n may be the initial frequency f2 or some other frequency. The bacterium responds to the electric field within time $t_{tr2}$, and reaches equilibrium within the PDEP trap. FIG. 35C shows bacterium captured in a PDEP trap at 10 MHz, at time t3=6 sec when the electrical field frequency is switched from 10 kHz to 10 MHz.

Figure 35D:
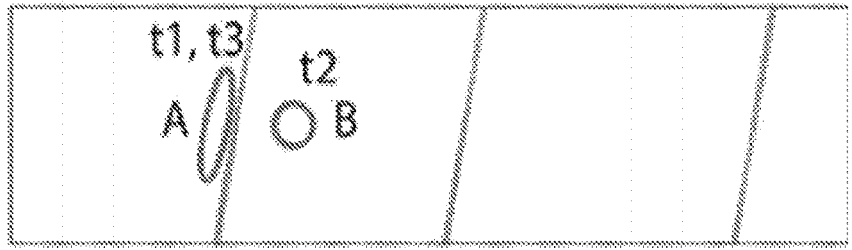
Figure 35E:
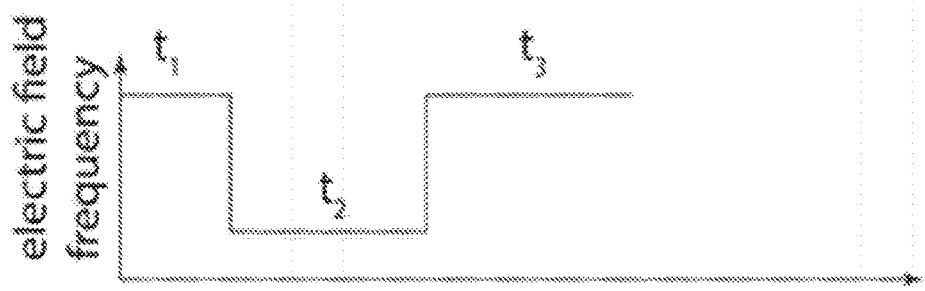
Figure 35F:
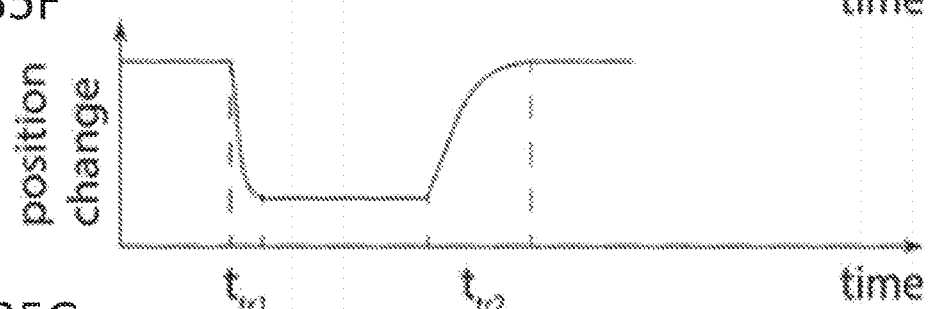
Figure 35G:
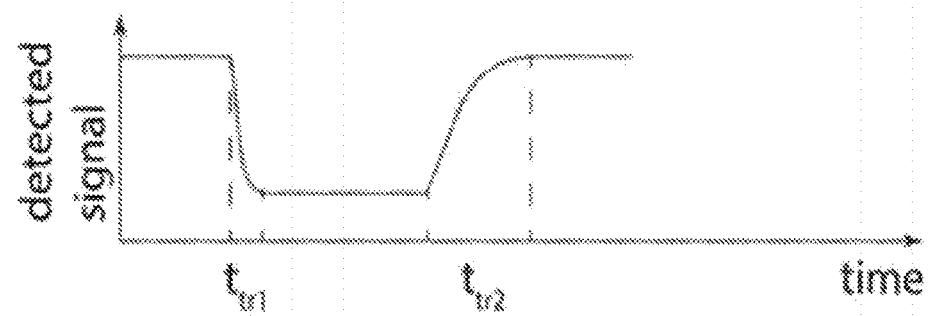
Figure 36A:
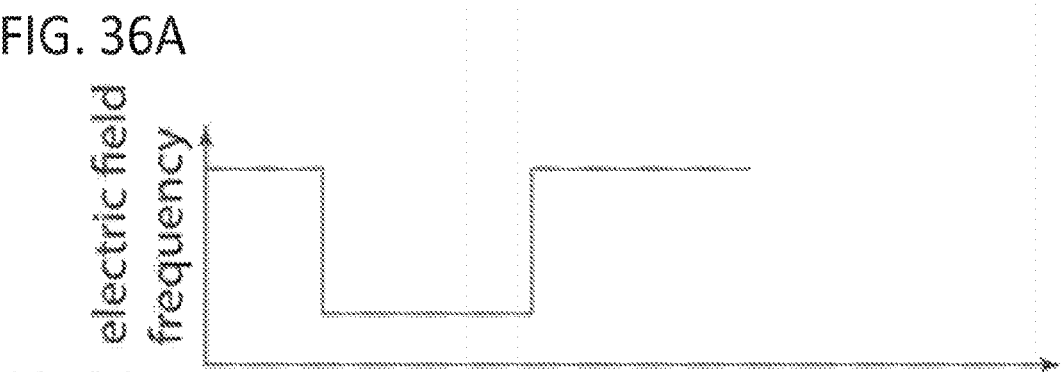
FIGS. 36A-D show that the oscillation between two electric field frequencies allows detecting activity on the electrodes and detecting bacterial or analyte motion in accordance with some embodiments.
Figure 36B:
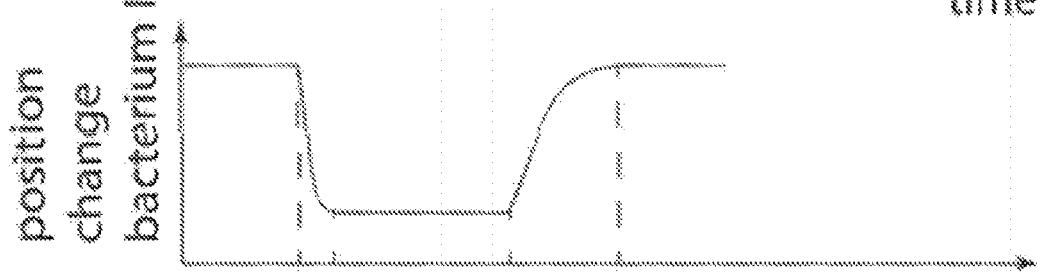
Figure 36C:
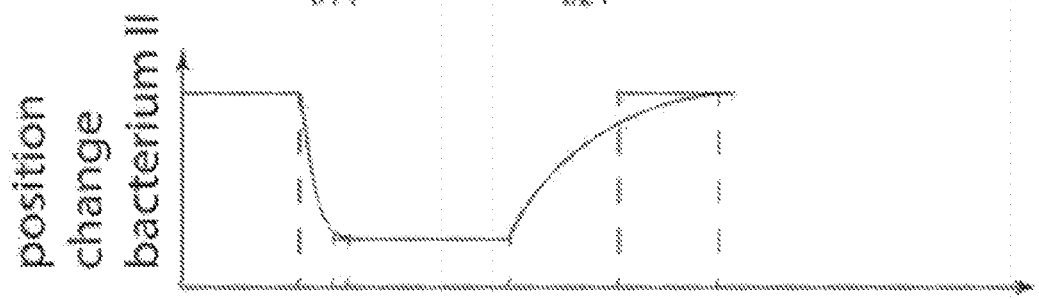
Figure 36D:
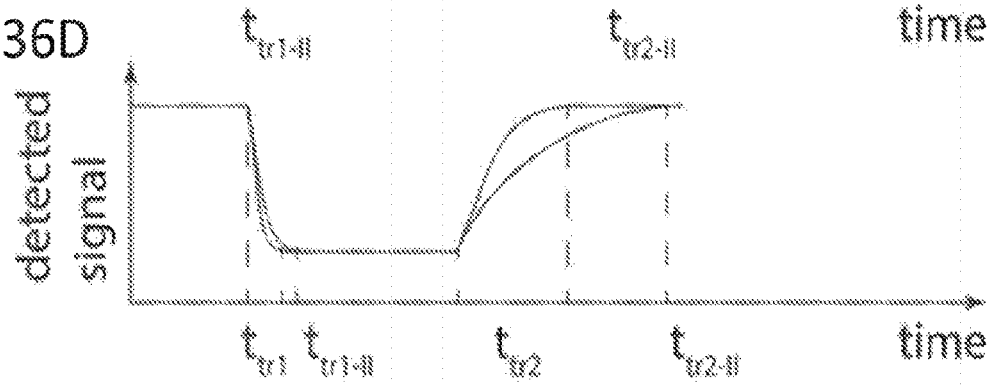
Figure 53:
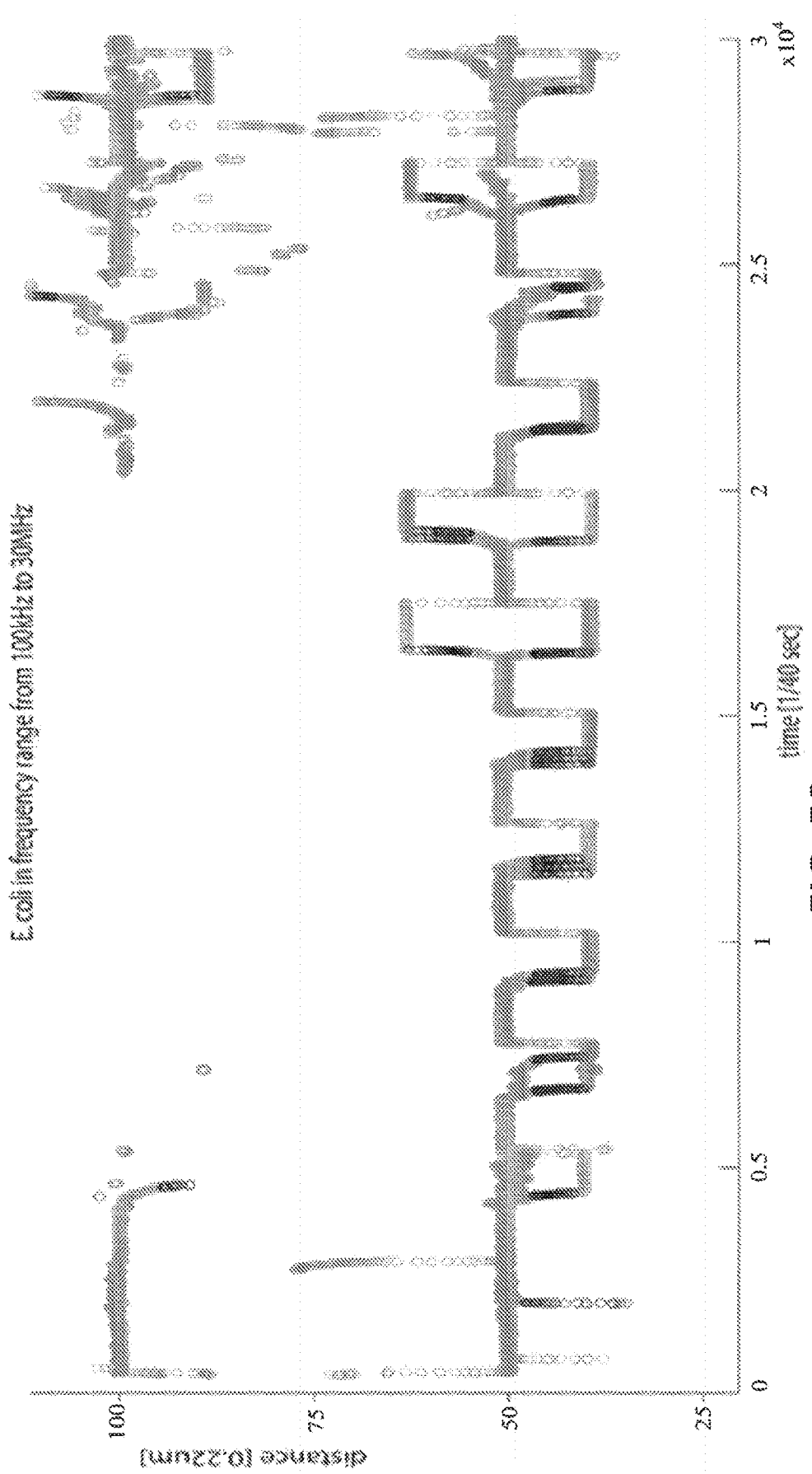
FIG. 53 shows trajectories of motion of E. coli bacteria measured and evaluated from the motion between PDEP and EO traps in accordance with some embodiments.
Figure 54:
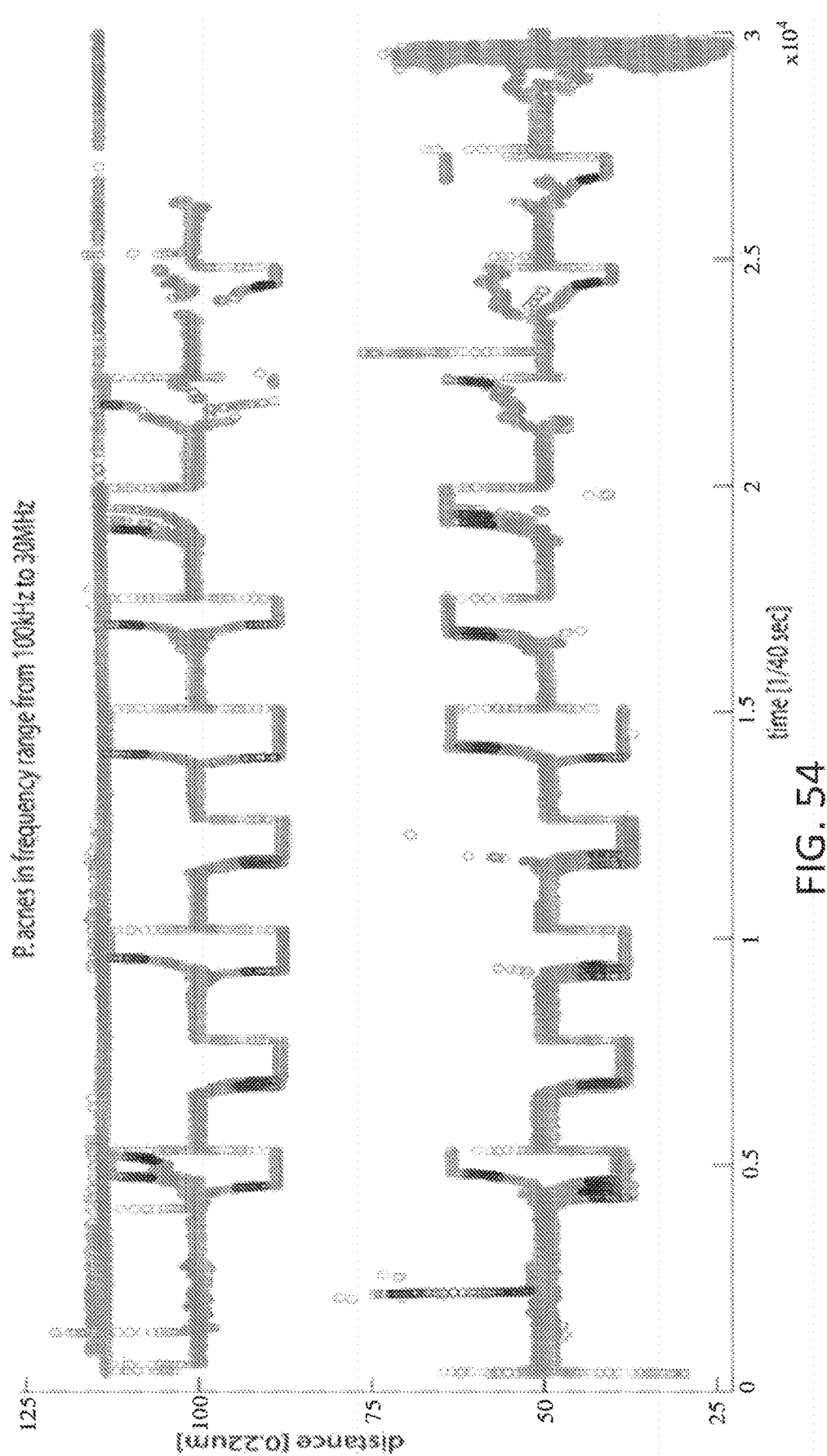
FIG. 54 shows trajectories of motion of P. acnes bacteria measured and evaluated from the motion between PDEP and EO traps in accordance with some embodiments.
Figure 55:
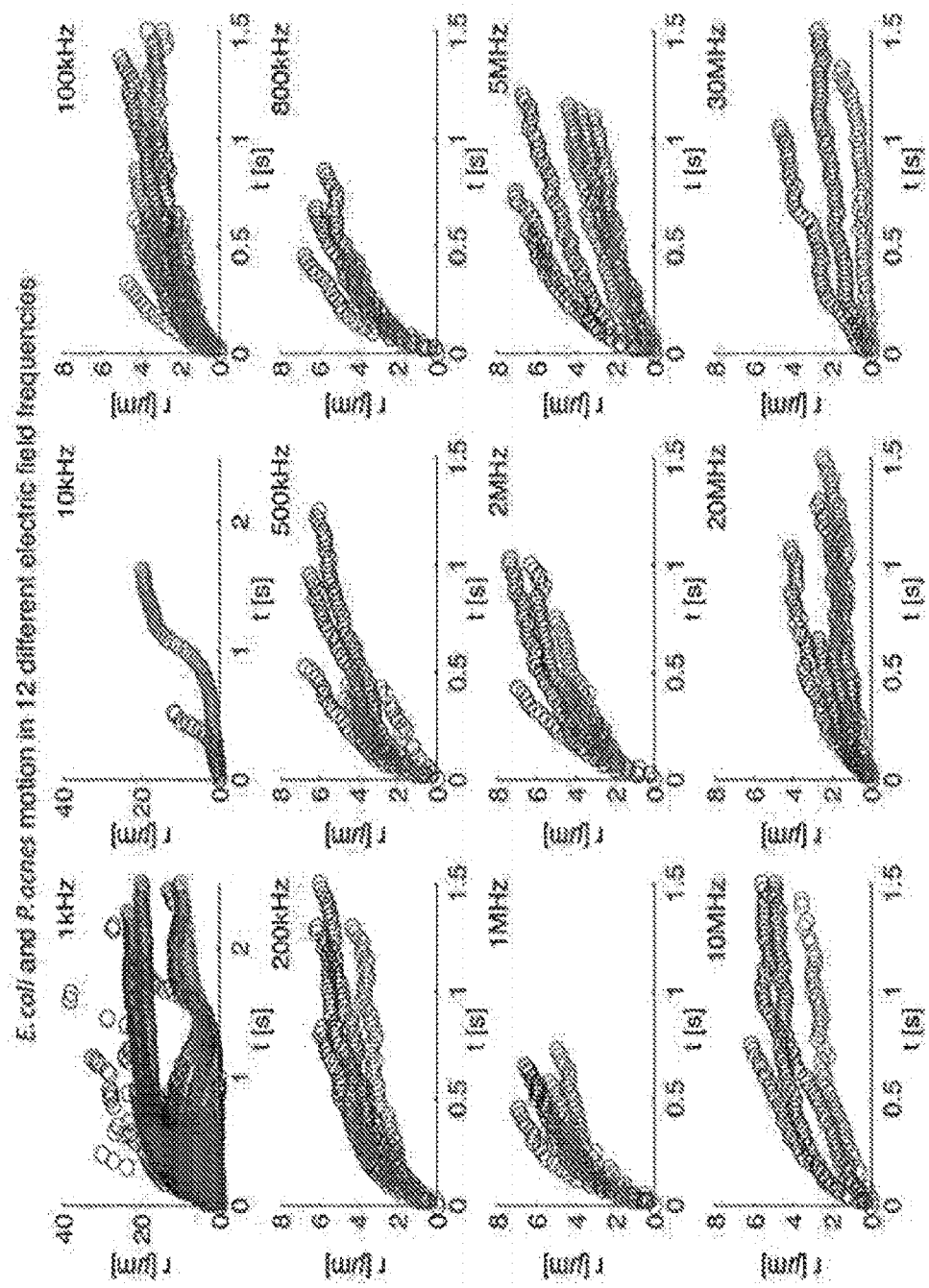
FIG. 55 shows superimposed trajectories of motion of E. coli and P. acnes bacteria measured and evaluated and compared from FIG. 53 and FIG. 54 for different frequencies.

FIG. 35D shows images superimposed in a time sequence and background removal, which allows tracking bacterial position in time. The differences in the image from frame to frame are due to bacterial motion. FIG. 35E shows a time sequence of pulses of an electric field applied in the example of FIG. 35—high for PDEP trap and low for EO trap. FIG. 35F shows how bacteria change position in response to the applied electric field. The characteristics of the motion (position in time) has a time constant characteristic for the transition between frequencies. FIG. 35G shows that the detected signal registers a change of signal properties in time compared to the pulses of the applied electric field when in high and low states. The data for extracting and measuring bacterial trajectories using the technique shown in FIG. 35 A-G and FIG. 36A-D are shown in FIGS. 53-55. In particular, FIG. 53 shows trajectories of motion of *E. coli* bacteria measured and evaluated from the motion between PDEP and EO traps in accordance with some embodiments, FIG. 54 shows trajectories of motion of *P. acnes* bacteria measured and evaluated from the motion between PDEP and EO traps in accordance with some embodiments, and FIG. 55 shows superimposed trajectories of motion of *E. coli* and *P. acnes* bacteria measured and evaluated and compared from FIG. 53 and FIG. 54 for different frequencies.

The transition times for bacterium to respond to the electric field of a given frequency, contain information related to the Clausius-Mossotti (CM) factor and the physical and chemical properties of a bacterium. In some embodiments, the transition times $t_{tr1}$ are measured to identify bacteria based on their spectral response signature.

FIG. 36 shows that the oscillation between FDEP(f2) and FEO(f1) allows detecting activity on the electrodes and detecting bacterial or analyte motion, hence analyte presence. The detected signal registers a change of signal properties in time compared to the pulses of the applied electric field states high and low. Different bacterial species exhibit differences in the spectral response. The differences in measured response times result in label-free bacterial identification.

If the intervals are repeatable, i.e., t1=t3, then Fswitch=2 pi/(t1+t2). Analyte detection is based on the induced repeatable oscillations with frequency Fswitch and the periodic (or not) change they cause in the register signal. In some embodiments, the signal is optical or electrical.

In one aspect, the bacterial response varies in the frequency range of the electric field from 1 kHz to 50 MHz. A database of unique bacterial signatures may be generated by scanning an entire frequency space (e.g., from 1 kHz to 50 MHz). A pulse train may be used to apply the electric field with a defined set of voltages and sampling frequencies to scan the entire frequency domain. Each applied frequency of the electric field allows measuring the response of a bacterium to the electric field and the associated time constant.

Additionally, if the frequencies of the pulse train vary, the bacterial spectral response and bacterial identification may be measured based on the spectral response or signature.

An amount of time that the analyte needs to travel in a functional electric field (waveform and pulse train) from one trapping center to another encodes analyte properties.

To develop a method to repeatedly and reproducibly test new sample matrices for analyte presence, a database may be generated in accordance with some embodiments. To generate the database the same pulse train may be applied to every solution containing bacteria to be analyzed. The output signal (e.g., an electrical or optical signal), may then be measured. The database, once generated, may be used to analyze a new sample by applying the previously defined pulse train to the new sample and comparing the output signal with the entries in the database. The system response registered to the applied pulse train allows bacterial identification and detection.

Some embodiments focus on detection of the presence of analyte in a solution rather than identification of the particular analyte that is detected. In such embodiments, analyte oscillation may be induced by switching the frequencies of the electric field between electroosmosis and dielectrophoresis-mediated trapping as discussed above. The oscillation purposefully induces localized noise. Analyzing the signal for the presence or absence of the localized noise provides information about the presence/absence of an analyte in the sample.

The detected signal can be, for example, optical or electrical, due to transistor gating, capacitive change or impedance change.

Figure 46A:
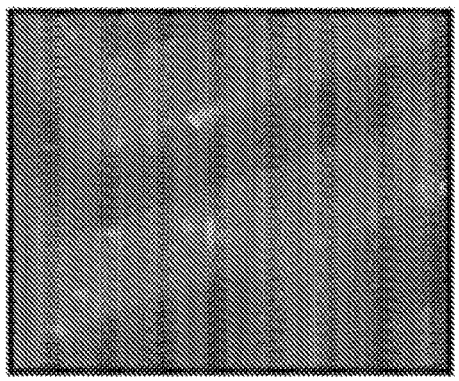
FIGS. 46A-F show images of capturing E. coli and E. faecalis bacteria in accordance with some embodiments.
Figure 46B:
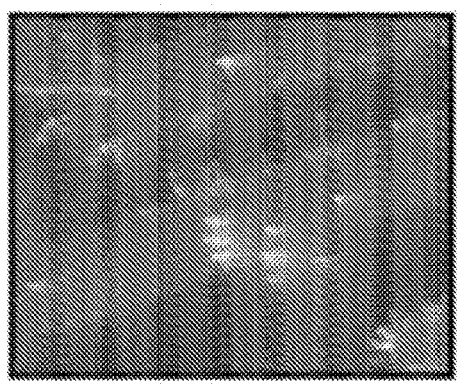
Figure 46C:
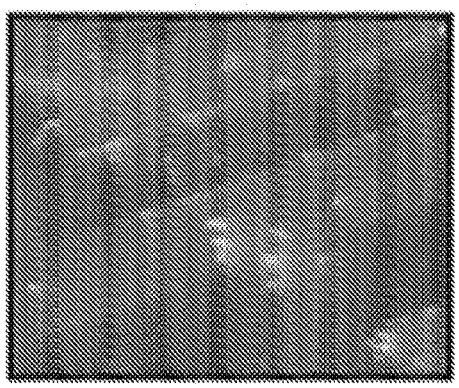
Figure 46D:
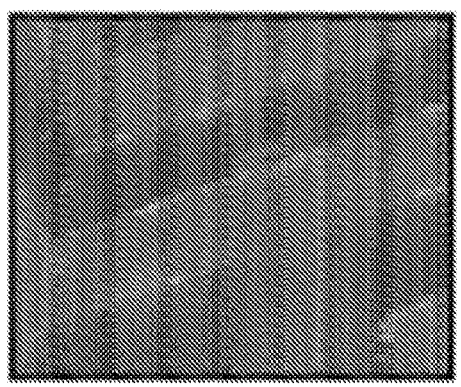
Figure 46E:
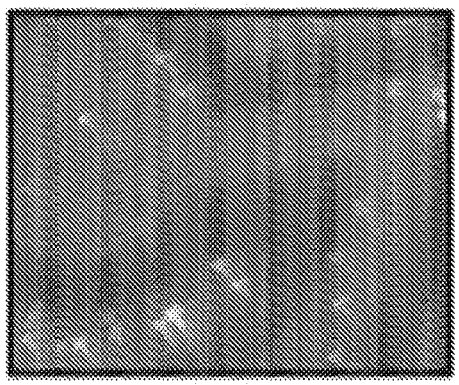
Figure 46F:
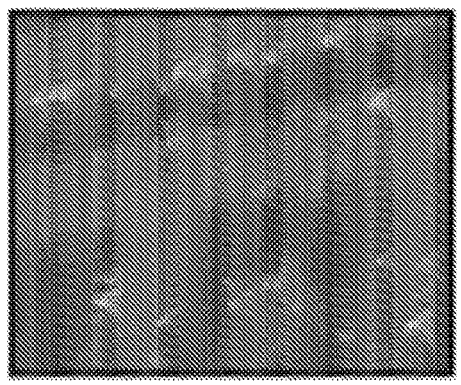

Some embodiments are directed to separating different analytes or bacteria using one or more of the switching techniques described herein. FIGS. 46A-D show images of capture and separation of *E. coli* and *E. faecalis* bacteria by switching the frequency of an applied electric field in accordance with some embodiments. FIG. 46A shows *E. coli* and *E. faecalis* bacteria randomly distributed in solution in the absence of an applied electric field. FIG. 46B shows capture of both *E. coli* and *E. faecalis* on the electrodes in the presence of an electric field having a frequency f1. *E. faecalis* bacteria are captured at the electrode edges with dielectrophoresis while *E. coli* bacteria are captured in the intra-electrode space with electroosmosis at 10 kHz. FIG. 46C shows that *E. coli* are no longer captured on the electrodes and *E. faecalis* is still captured on the electrodes in the presence of an electric field having a frequency f2, resulting in *E. coli* and *E. faecalis* separation. FIG. 46D shows *E. faecalis* captured on the electrode system, with the *E. coli* bacteria removed demonstrating successful *E. coli* and *E. faecalis* separation. FIG. 46E shows *E. faecalis* captured in a dielectrophoresis trap (shown as captured on the edges of the electrodes) and *E. coli* captured in an electroosmosis trap (shown as captured in the center of the electrode). FIG. 46F. shows *E. faecalis* and *E. coli* bacterial simultaneously captured in a dielectrophoresis trap (shown as captured on the edges of the electrodes) at 1 MHz. This approach allows separation of *E. coli* from *E. faecalis* bacteria by application of differential electric fields (e.g., as shown in FIG. 46D).

Another aspect of some embodiments is directed to implementing testing for analyte response to chemicals or drugs, such as bacterial antibiotic susceptibility. In such embodiments, the bacterial response to a frequency pulse train is measured and the trajectories of motion between the PDEP and EO traps are evaluated, then bacteria are exposed to antibiotics and the response to pulse train is evaluated for differences.

Another aspect of some embodiments is directed to implementing analyte absorption of chemical agents such as drug delivery upon exposure to a selective electric field due to modified analyte properties resulting from expose in certain regions of the electric field. This technique may be used, for example, for electrical cell gating for drug delivery.

Two AC Frequency Detection Technique

Due to enhanced sensitivity, transistors which use the field effect principle with analyte causing gating and drain current modulation are attractive for biosensing applications. Some conventional transistors use a planar geometry for source and drain definition and the formation of the active channel. Other approaches use the active channel of a transistor defined in a one dimensional system in a nanostructure, e.g., a silicon nanowire.

U.S. Patent Application No. 2015/0107999 and U.S. Pat. No. 9,120,105, referenced above, describe a technique for detecting bacteria using a nanowire sensor array. In some respects, nanowire sensors may be challenging and resource intensive for manufacturing and integration with other components of the system. For example, biological sensing typically requires larger feature sizes to ensure contact with the large surface analyte than nanowires provide.

Some embodiments described herein allow for use of larger structures with a significantly reduced number of manufacturing steps and reduced manufacturing complexity. Bacterial detection is achieved using a sensor edge with a sensor channel in the size range between nanometers and hundreds of microns up to millimeters. In one aspect, using the sensor edge for bacterial detection obviates the need for a nanowire sensor.

A device in accordance with some embodiments applies high frequency AC electric field (e.g., in the 300 Hz-100 MHz range) to turn on the transistor and set the operating point for drain current.

Application of AC electric field for both transistor operation and analyte transport modulation results in an integrated system with a bacterial transport chip and a sensor chip integrated into one device. The integration of high surface coverage electrodes with the sensor chip allows to effectively overcome diffusion limitations in analyte transport.

One aspect allows for the use of the geometry of the active channel chosen such as to have a high surface coverage to increase the probability of analyte interaction with the sensor surface or confinement within proximity to the sensor and analyte detection. FIG. 37 shows a top view (above) and a cross section (below) of a transistor configured as a biosensor. The labels in FIG. 37 are described as follows: (1) Silicon or semiconductor active channel; (2) Silicon or semiconductor or metal reference electrode; (3) Metal contacts; (4) Handle wafer or substrate (silicon, glass or other); (5) Insulator; (6) Insulating or protective coating (optional).

The active channel of a transistor is connected to source and drain regions. An AC electric field causing analyte trapping on the sensor surface or sensor edge may be applied to the metal contacts. The high frequency electric field (e.g., in the range from 300 Hz to 50 MHz) causes analyte transport to the sensor surface (for example, as shown in FIG. 20). Analyte contact with the sensor surface causes gate modulation or a capacitive or impedance change and as a result a change in the measured signal.

Bacteria trapped in a dielectrophoresis trap at the trapping electric field frequency FDEP(f2) are in contact with an edge of the sensor. Analyte trapping using dielectrophoresis results in analyte contact with the sensor and signal 'ON'. Bacteria trapped in an electroosmosis trap at the electric field frequency FEO(f1) are vertically aligned above the sensor surface, trapping using electroosmosis results in turned off analyte contact with the sensor and signal 'OFF'. Additionally, switching between the two electric fields frequencies FDEP(f2) and FEO(f1) at a switching frequency Fswitch may provide a ON an OFF switch to the sensor, as discussed above, and is the basis for a Dual AC Gate modulation technique described herein for analyte detection.

The conductivity of the electrode system changes when bacteria are trapped on the electrode edges or in the electrode center (intra electrode space). When the frequency Fswitch is applied to create an ON and OFF switch, the conductivity of the electrode system changes between the ON and OFF states. The measurement of the electrode system impedance at the frequency Fswitch as, for example, in a lock-in detector may enhance the sensitivity and limit of the bacterial detection.

The application of a low frequency electric field switching modulates the bacterial transport to the sensor surface and gate modulation for bacterial and analyte detection. One aspect allows for multiple electrodes (source, drain regions) in one device. Another aspect allows for use of planar silicon or semiconductor layer where the active channel of the transistor is formed.

FIG. 38 shows a device in which the source and drain contacts are electrodes, which geometry has high surface coverage to increase the probability of analyte interaction with the sensor surface or confinement within proximity to the sensor and analyte detection. The labels in FIG. 38 are described as follows: (1) Electrode; (2) Electrode; (3) Insulator; (4) Handle wafer or substrate (silicon, glass or other);

(5) Insulator; (6) Insulating or protective coating (optional); (7) Silicon or semiconductor layer.

Figure 39:
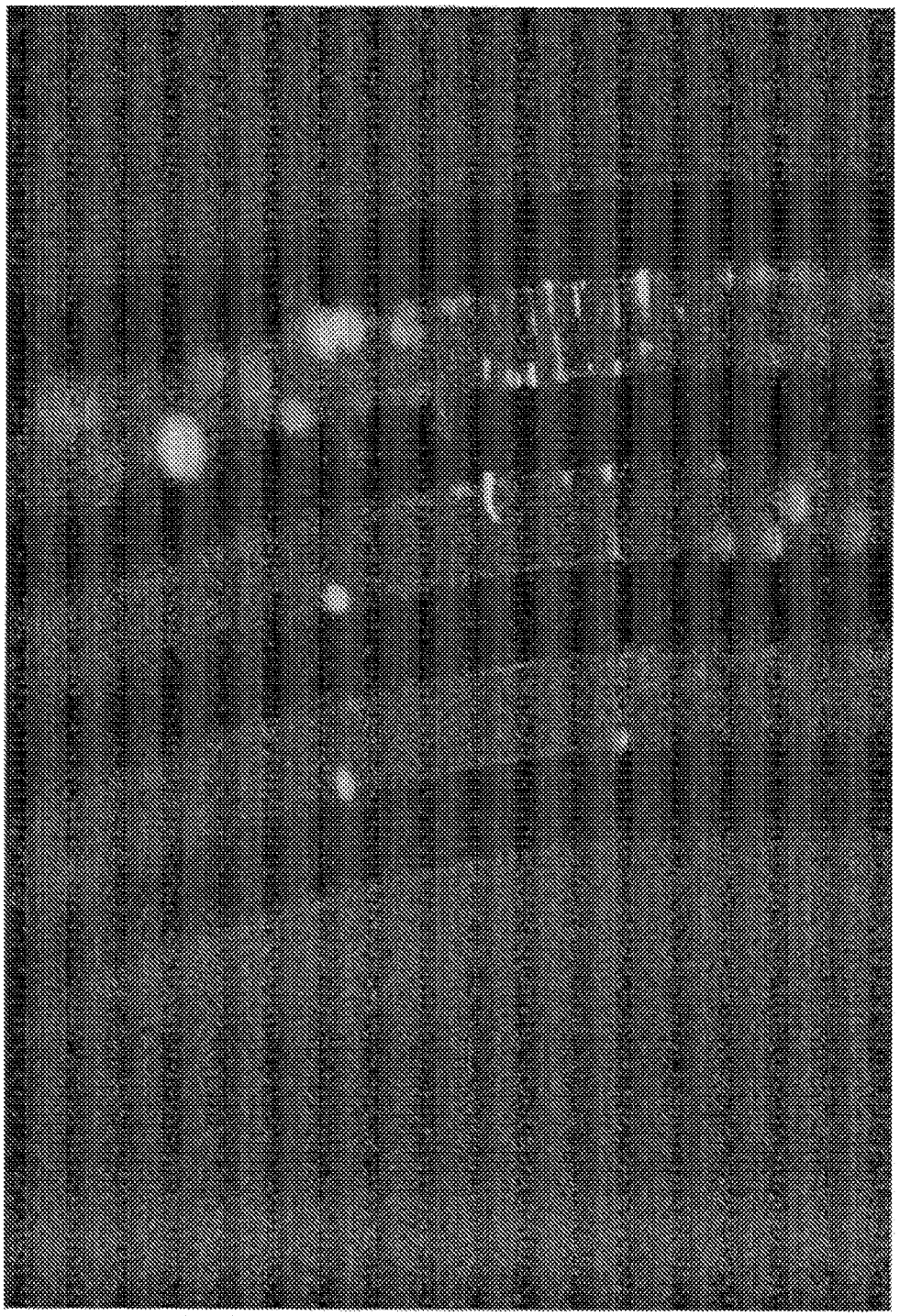
FIG. 39 shows capture of E. coli bacteria using the device shown in FIG. 38.
Figure 40:
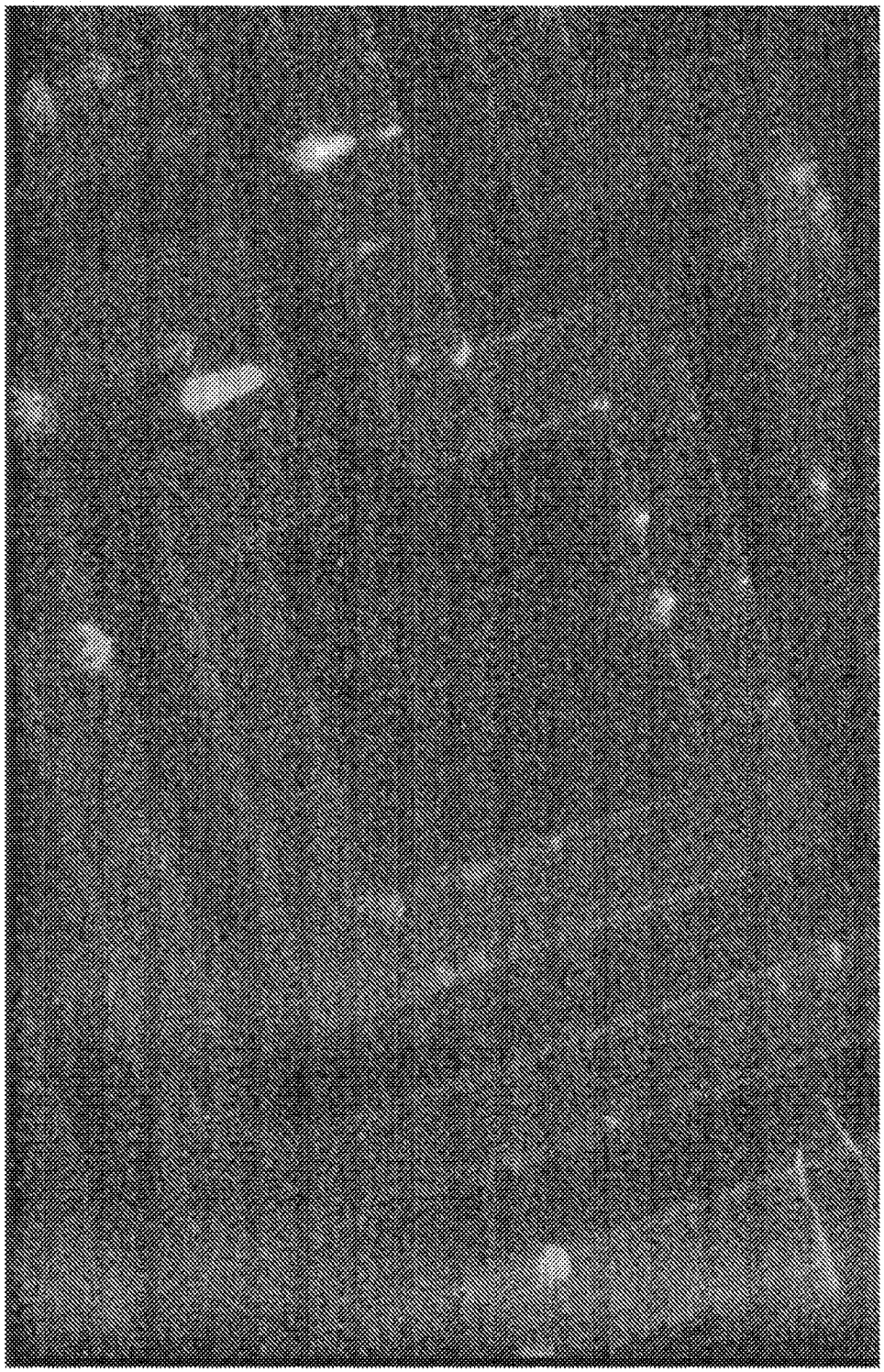
FIG. 40 shows capture of E. coli bacteria using a square electrode geometry rather than the circular electrode geometry used in the device of FIG. 38.

FIG. 39 shows capture of *E. coli* bacteria using the device shown in FIG. 38. FIG. 40 shows capture of *E. coli* bacteria using a square electrode geometry rather than the circular electrode geometry used in the device to capture the image in FIG. 39. High surface coverage and long/large features were chosen to enhance sensing. Conventional transistors tend toward minimization of feature sizes.

Yet another aspect allows for use of a protective coating, such as gate insulator or an anti-adhesion layer or an anticorrosive layer, over the active channel and or the electrodes and contacts.

FIGS. 41 and 42 show a device with a planar silicon or semiconductor layer where the active channel of the transistor is formed. The electrodes, e.g., solution gate electrodes, to which the AC electric field is applied, are configured to attract the analyte. The labels in FIG. 41 are described as follows: (1) Electrode; (2) Electrode; (3) Insulator; (4) Handle wafer or substrate (silicon, glass or other); (5) Insulator; (6) Insulating or protective coating (optional); (7) Silicon or semiconductor layer; (8) Electrodes for Source and Drain contacts. The labels in FIG. 42 are described as follows: (1) Electrode; (2) Electrode; (3) Insulator; (4) Handle wafer or substrate (silicon, glass or other); (5) Insulator; (6) Insulating or protective coating (optional); (7) Silicon or semiconductor layer; (8) Electrodes for Source and Drain contacts.

In some embodiments, the source and drain contacts are placed outside of the structure or from the inside to the outside. This allows for transistor operation with either AC or DC voltage bias applied to the Drain/Source and Gate/Source regions.

FIG. 43 shows a device, where the source and drain contacts are electrodes, which geometry has a high surface coverage to increase the probability of analyte interaction with the sensor surface or confinement within proximity to the sensor and analyte detection. The active sensor area is defined between the source and drain electrodes. The labels in FIG. 43 are described as follows: (1) Electrode for Source Drain contacts; (2) Electrode for Source Drain contacts; (3) Semiconductor Silicon or semiconductor layer; (4) Handle wafer or substrate (silicon, glass or other); (5) Insulator; (6) Insulating or protective coating (optional).

Yet another aspect allows for etching the active sensor area. This allows for formation of edges to improve analyte transport and contact with the sensor surface for detection, e.g., by analyte trapping using a dielectrophoresis trap for signal modulation.

Figure 44A:
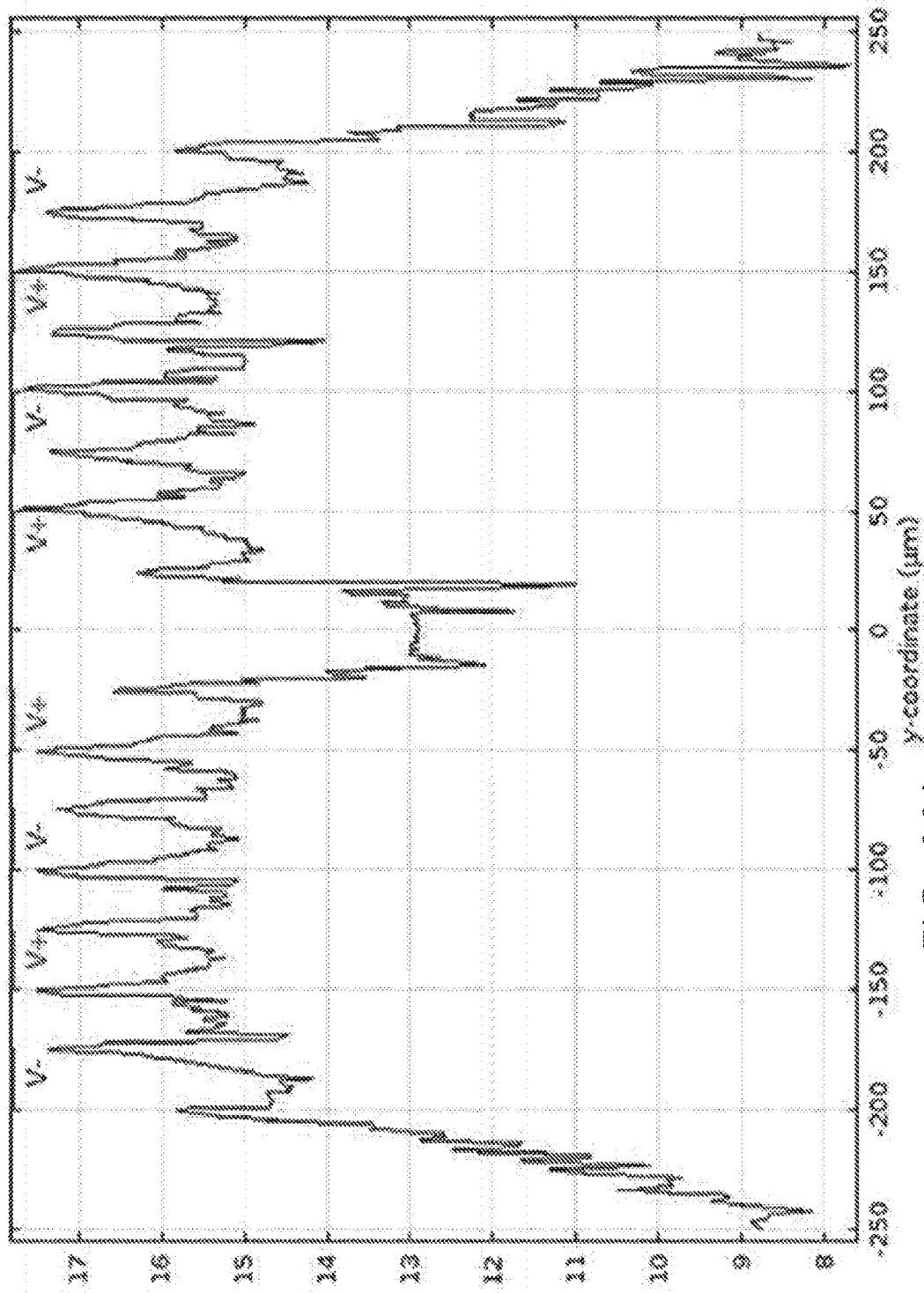
FIGS. 44A-C and FIGS. 45A-B show the magnitude of the gradient component z of the normalized electric field squared at 1 μm distance above the electrode surface along the symmetry axis plotted on the logarithmic scale in accordance with some embodiments.
Figure 44B:
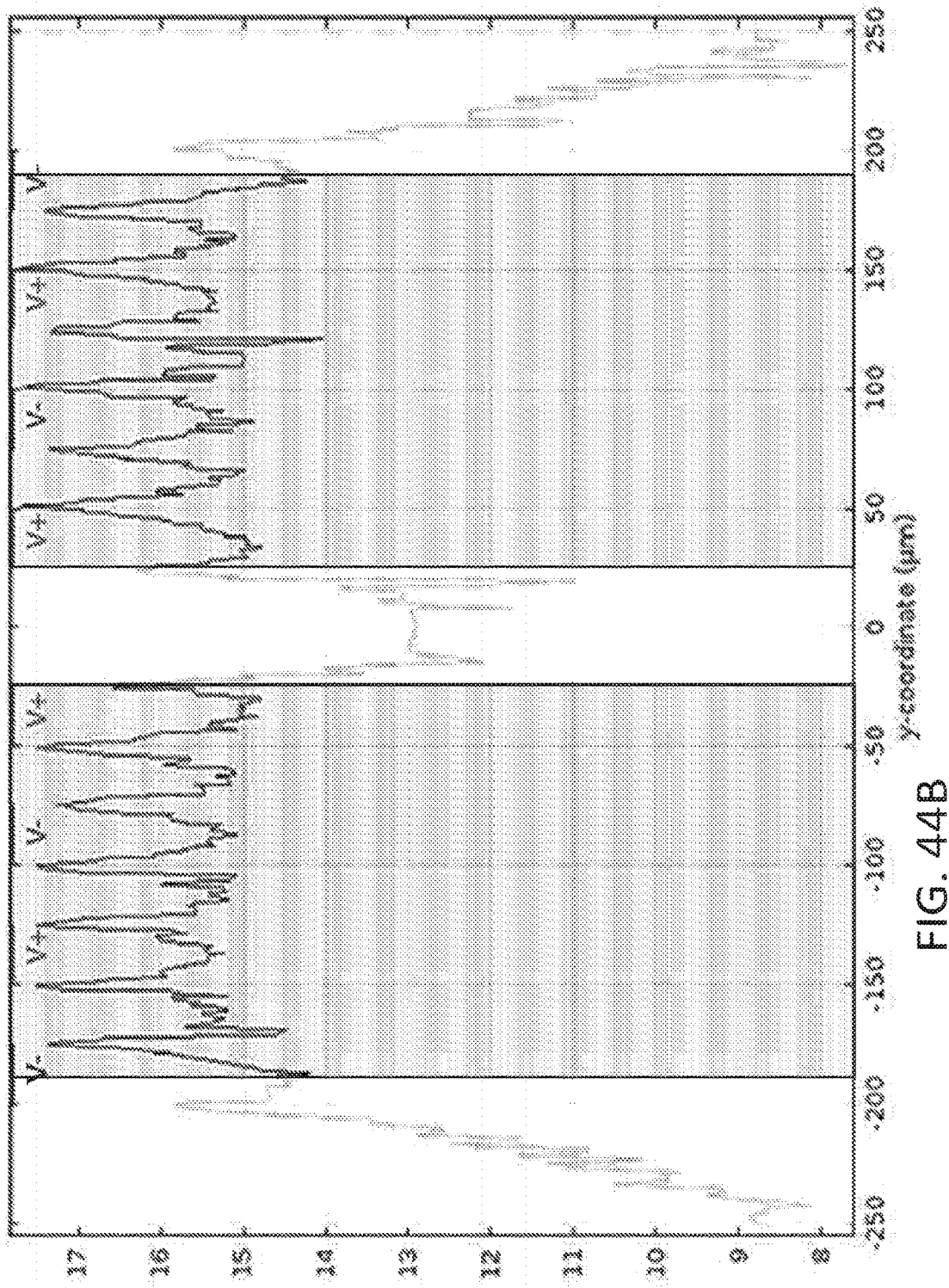
Figure 44C:
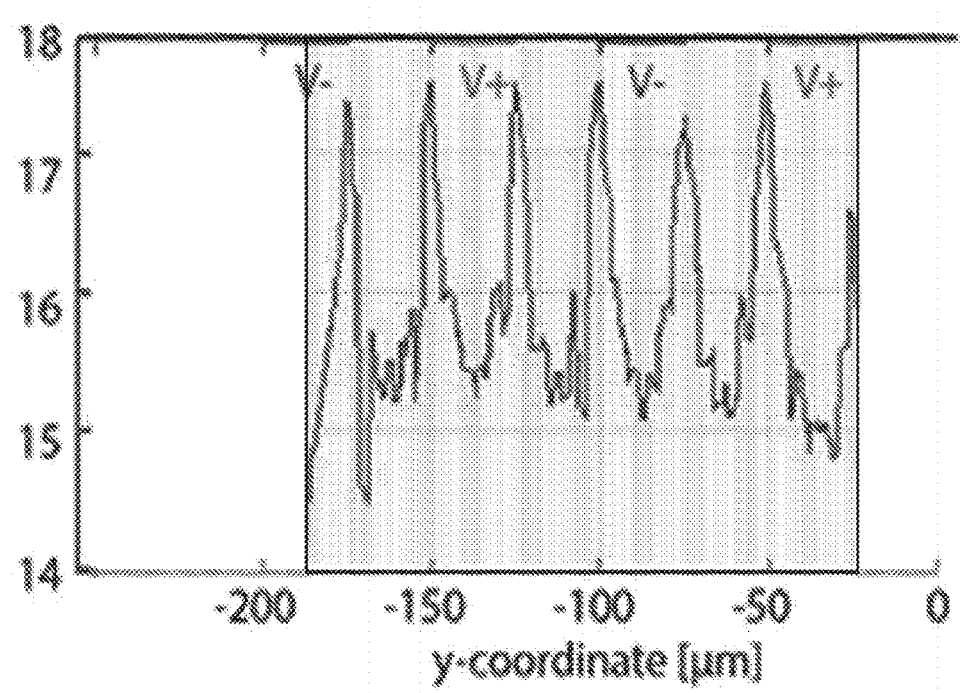
Figure 45A:
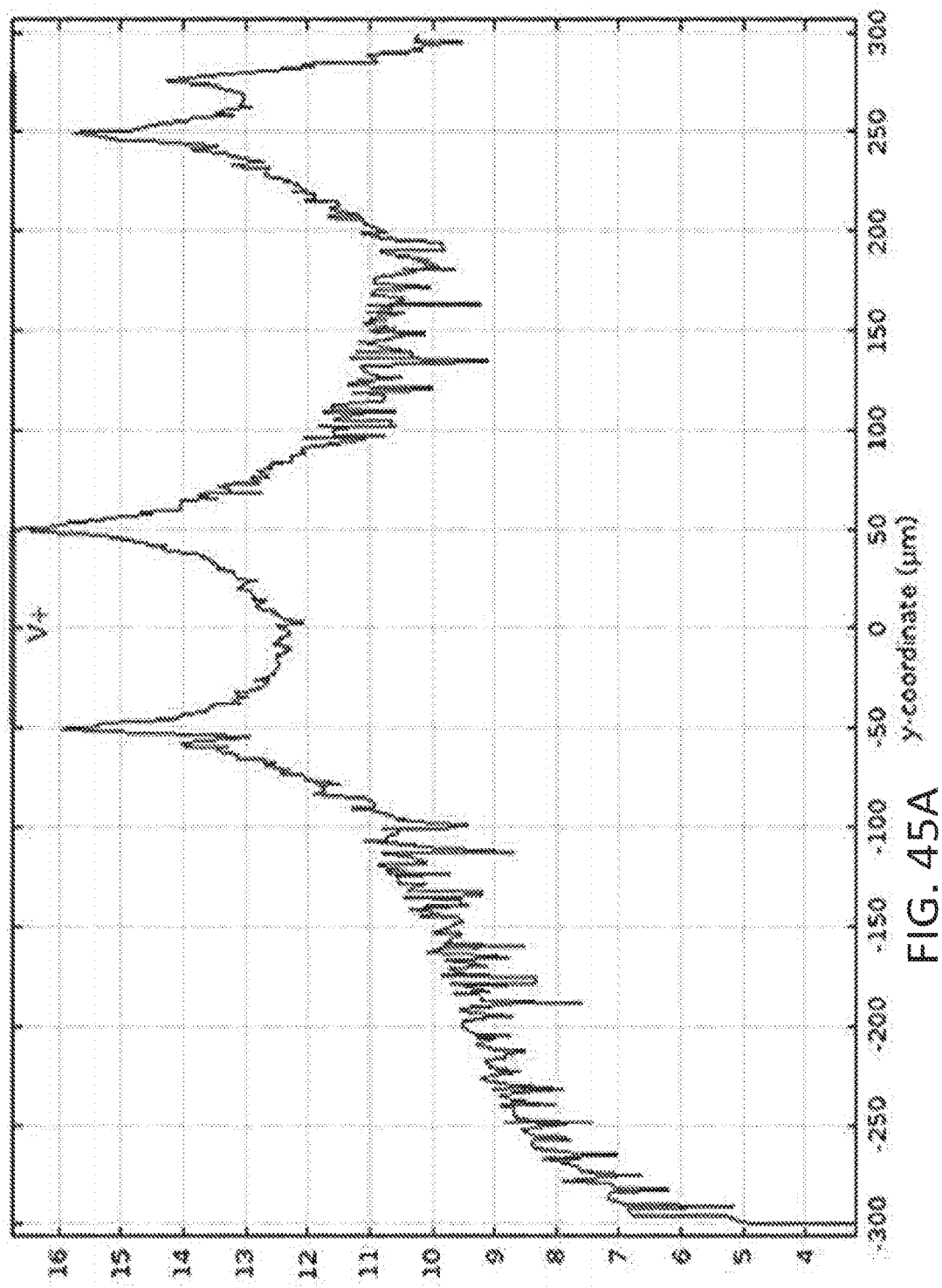

FIGS. 44 and 45 show the magnitude of the gradient component z of the normalized electric field squared at 1 µm distance above the electrode surface along the symmetry axis plotted on the logarithmic scale. As shown, the gradient of the electric field is strongest on the edges of the electrodes pointing towards the electrode of the opposite polarity. For the ring structure the magnitude of the gradient of the electric field is between $10^{17.5}$ $V^2/m^3$ and $10^{18}$ $V^2/m^3$ in the periodic structure and drops to around $10^{16}$ $V^2/m^3$ at the electrode edges at the end of the structure. In the center of the inner ring, where the boundaries of the region have the same potential value, the magnitude drops to as low as $10^{13}$ $V^2/m^3$. The field in the region between electrodes and in the electrode center is approximately $10^{15}$ $V^2/m^3$.

Figure 45B:
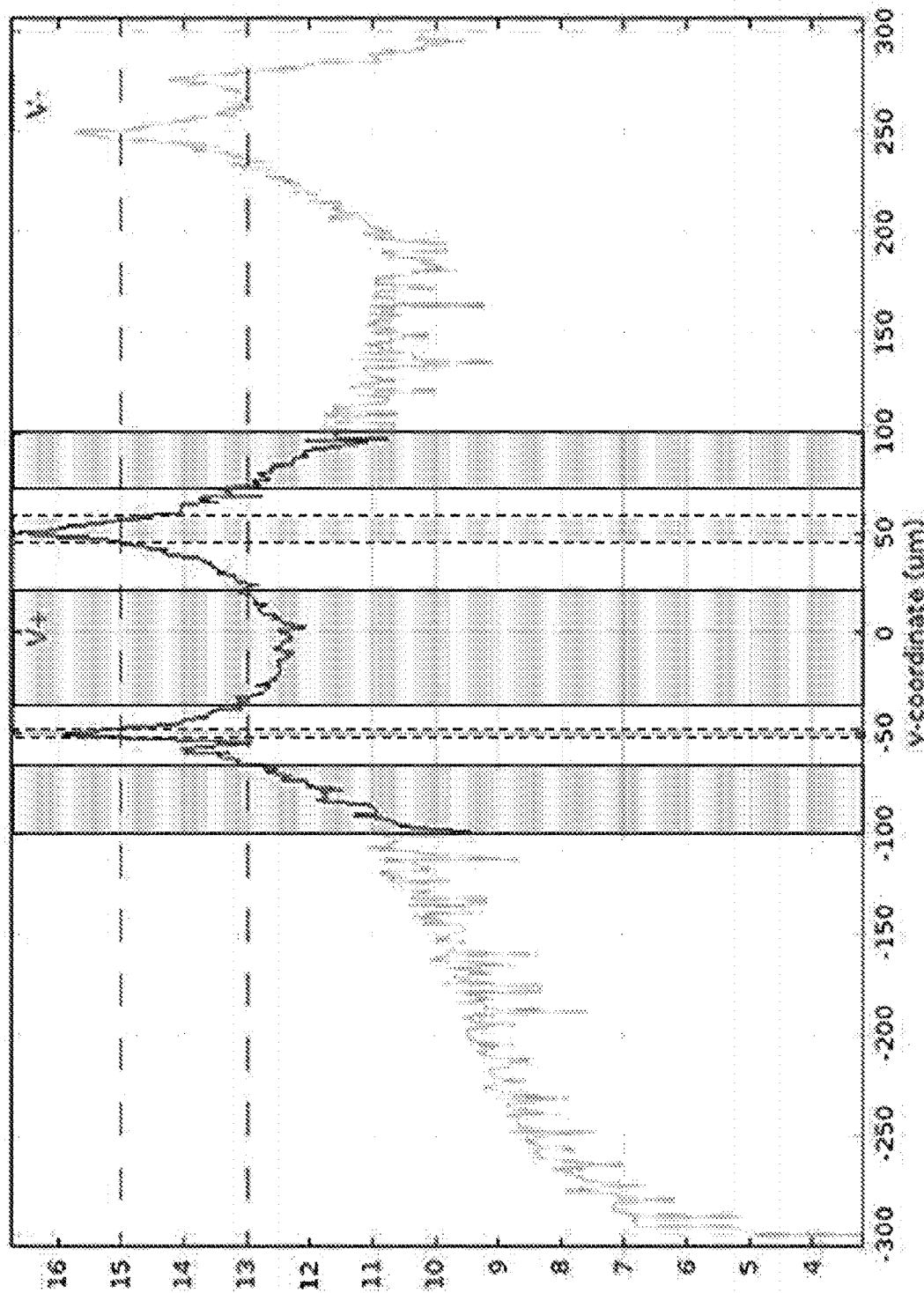

As shown in FIG. 45B, in the dotted structure the maximum magnitude of the gradient of the electric field squared is reached on the edge of the electrode pointing toward the counter electrode and is equal to $10^{16.5}$ $V^2/m^3$. The opposite edge has a magnitude value of $10^{16}$ $V^2/m^3$. In the electrode center the magnitude value is $10^{12.5}$ $V^2/m^3$. The magnitude of the gradient drops to $10^{11}$ $V^2/m^3$ in the distance between electrodes. The highlighted region in FIG. 45B is the region experimentally validated.

As evidenced in the data, a magnitude of the gradient equal to $10^{15.5}$ $V^2/m^3$ is a strong enough electric field to efficiently pull *E. coli* bacteria (τ<1 sec, $I_{t\to\infty}$=0), however, whereas a magnitude of the gradient of the electric field below $10^{13}$ $V^2/m^3$ is not (τ~50 sec, $I_{t\to\infty}$=constant). This observation enabled definition of a clearing zone also called the depletion zone and the resistance zone as shown in FIG. 45B and in FIG. 14.

Some embodiments are directed to an actionable spectrometer configured to provide label-free analyte (e.g., bacterial) fingerprinting using an electric field. As discussed above, the CM factor for an analyte has proved to be useful for differential analyte separation as shown in FIG. 46. However, measurement of the CM factor directly has not been possible using existing techniques. Identifying differential conditions where there is a different CM factor for two types of analytes to be separated is impractical with existing techniques. Some embodiments are directed to a technique for measuring the CM factor of an analyte by measuring the PDEP force acting on an analyte particle. The DEP force is proportional to the CM factor. All other parameters being known, the inventor has recognized that it is sufficient to measure the PDEP force acting on an analyte particle to determine its CM factor.

PDEP force from Newton's law of motion is proportional to the particle mass multiplied by the particle acceleration. The particle acceleration can be calculated from the particle's trajectory in time.

When analyte particles are attracted to the electrode system from the bulk of a solution their trajectory is 3 dimensional and as such difficult to measure. A microscope camera allows measuring a projection of a 3-dimensional motion onto a 2-dimensional plane. Accordingly, some embodiments are directed to measuring a motion of an analyte particular confined to a 2-dimensional plane.

In some embodiments, two or more AC kinetic traps are constructed and motion parameters of an analyte are determined as the analyte is moved between the two traps by changing conditions and measuring the particle trajectory.

Figure 47A:
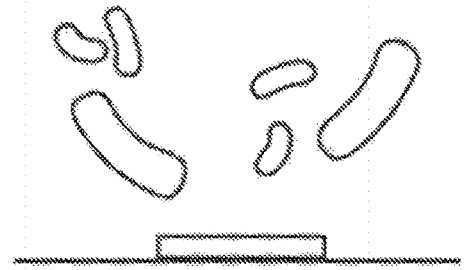
FIGS. 47A-H show a technique for measuring a bacterial response to an applied electric field in accordance with some embodiments.
Figure 47B:
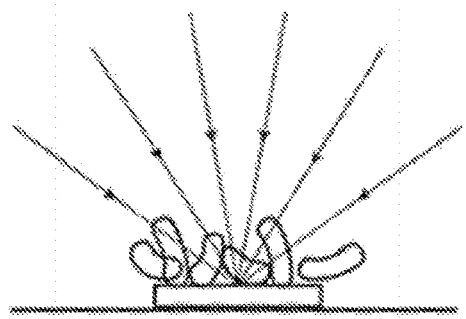

FIGS. 47A-H illustrate a technique for measuring the bacterial response to the electric field. FIG. 47A shows that analyte particles are randomly distributed in a solution before an electric field is applied. When an electric field is applied, as shown in FIG. 47B, analyte particles are captured on the electrodes. The lines with arrows indicate the direction of the electric field lines after the electric field is applied.

Figure 47C:
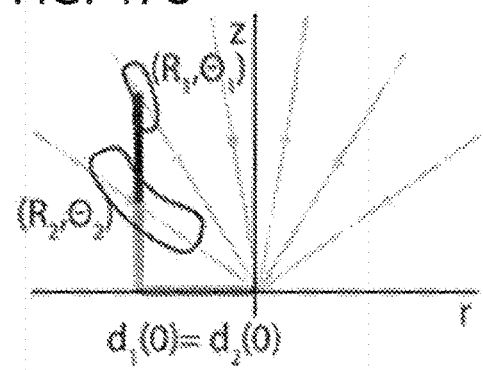
Figure 58:
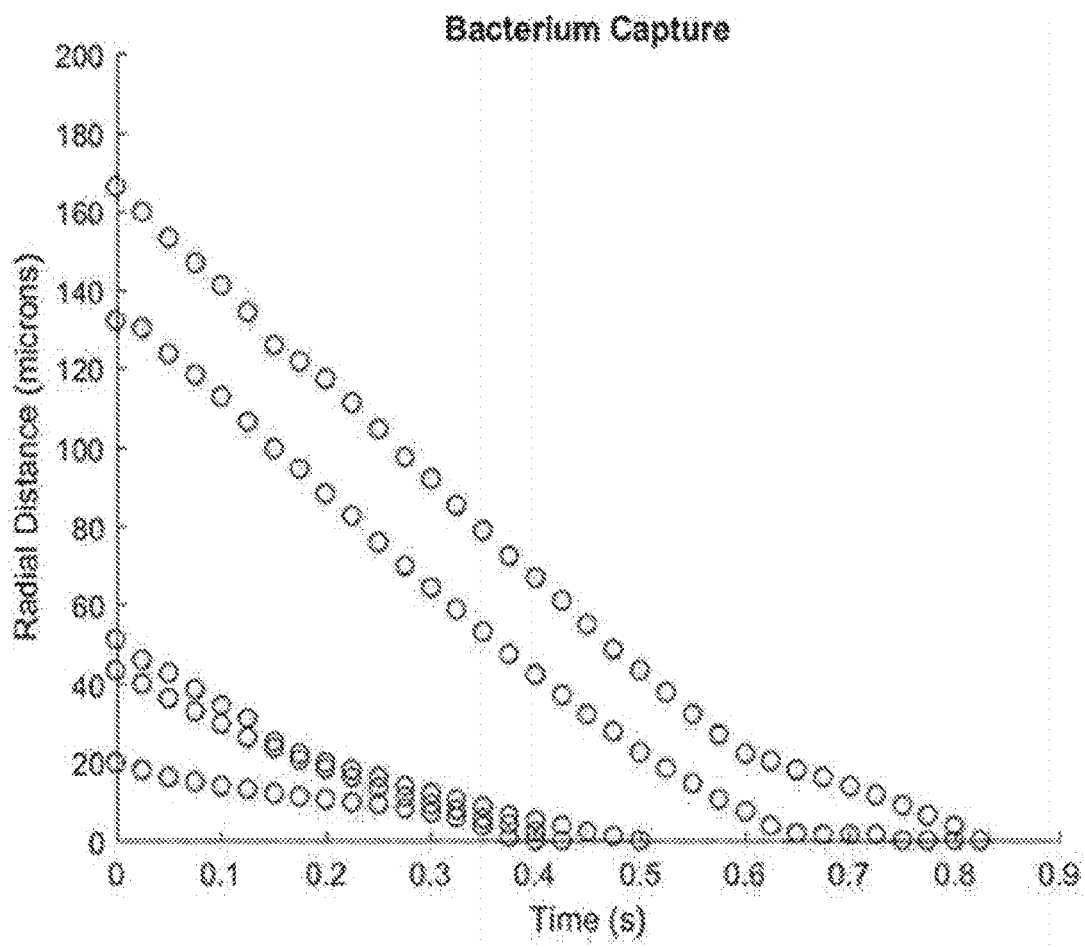
FIG. 58 shows trajectories of E. coli bacteria measured and captured from the bulk of the solution in a same experiment, but without the motion confinement between two traps; in accordance with some embodiments.

FIG. 47C shows that when analyte particles are captured from the bulk of the solution they move in three dimensions and are captured in the center of the trap, which is either on the electrode close to the center of the electrode or on the electrode edge. For an electrode system the trajectory of motion for every analyte particle has a radial component R(t), which is the distance between the analyte particle and the trapping center, and an angular component Θ(t), which is the angle between the line between the analyte particle, the trapping center and the plane normal to the electrode surface. FIG. 58 shows trajectories of *E. coli* bacteria captured from the bulk of the solution indicating that trajectories for the same type of bacterium may vary.

The trajectory of motion d(t) observed with the microscope is a projection of the analyte particle 3D motion onto a 2D plane: $d(t)=R(t)\sin(\Theta(t))$. Two analyte particles of the same type may have different starting positions, but the same projections: $d1(t)=R1(t)\sin(\Theta1(t))$ and $d2(t)=R2(t)\sin(\Theta2(t))$. In this case their trajectory length (traveled distance) is different, they are exposed to a different electric field or electric field gradient above the electrode system and hence have different travel times.

Figure 47D:
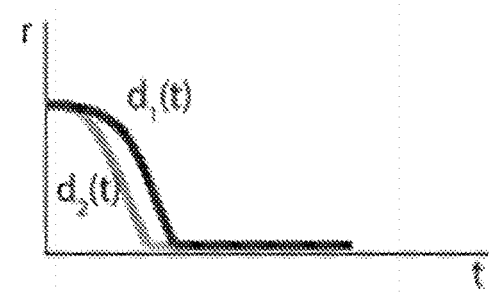

FIG. 47D shows, measures with a microscope, the 2D trajectory for two analyte particles of the same type, with the same starting 2D projection ($d1(0)=d2(0)$), but different starting distance from the trapping center ($R1 \neq R2$). The measured trajectories $d1(t)$ and $d2(t)$ are different for the same type of analyte particle, hence this measurement shows differences $d1(t) \neq d2(t)$ for the same type of particle, due to the difference in starting position and not due to the differences between particles. An accurate measurement would show the same trajectories for the same types of particles.

Figure 47E:
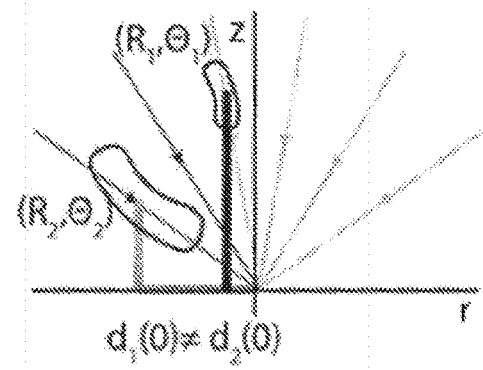

FIG. 47E shows two analyte particles of the same type may have different starting positions, and different projections. In this case their trajectory length (traveled distance) is different, they are exposed to a different electric field or electric field gradient above the electrode system and hence have different travel times.

Figure 47F:
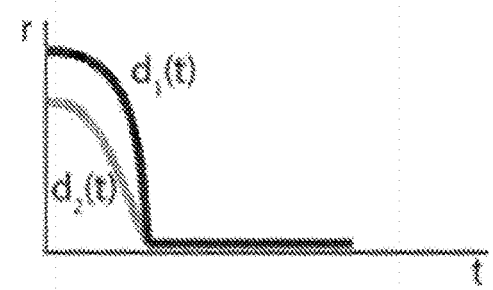

FIG. 47F shows, measured with the microscope, the 2D trajectory for two analyte particles of the same type, with different starting 2D projections ($d1(0) \neq d2(0)$), and different starting distance from the trapping center ($R1 \neq R2$). The measured trajectories $d1(t)$ and $d2(t)$ are different for the same type of analyte particle, hence this measurement shows differences $d1(t) \neq d2(t)$ for the same type of particle, due to the difference in starting position and not due to the differences between particles. An accurate measurement would show the same trajectories for the same types of particles.

Figure 47G:
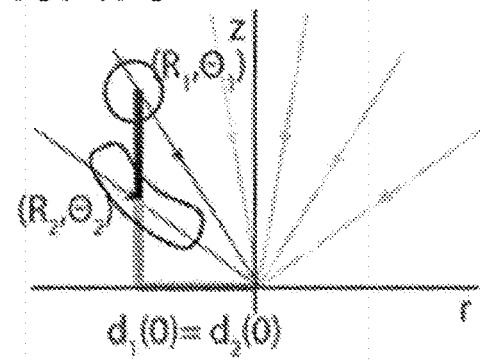

FIG. 47G shows two different analyte particles of different type may have different starting positions, and the same projections. In this case their trajectory length (traveled distance) is different, they are exposed to a different electric field or electric field gradient above the electrode system and may have the same response to the electric field.

Figure 47H:
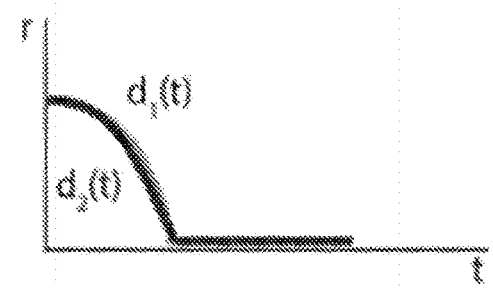

FIG. 47H shows, measured with the microscope, the 2D trajectory for two analyte particles of the different types, with the same starting 2D projections ($d1(0)=d2(0)$), and different starting distance from the trapping center ($R1 \neq R2$) and different response to the electric field. The measured trajectories $d1(t)$ and $d2(t)$ may be the same for different types of analyte particle, hence this measurement may show similarities $d1(t)=d2(t)$ for different type of particle. Their measured different travel times may be different or the same and hence the measurement may be inconclusive. An accurate measurement would show different trajectories for different types of particles.

This method of evaluating particle trajectories from particle capture from the bulk, may not be accurate enough to determine the particle type or particle properties, since the measured result depends on the starting position.

FIGS. 48A-F describe an alternative technique for determining particle trajectories in two dimensions in accordance with some embodiments. Fixing the distance bacteria travel to be the same for all bacteria as the distance between two trapping centers allows for all bacteria to have the same trajectories and be exposed to the same electric field. With all parameters being the same for all measured analyte particles but the differences between the particles themselves, the different measured travel times correspond to the differences between particles only.

Figure 48A:
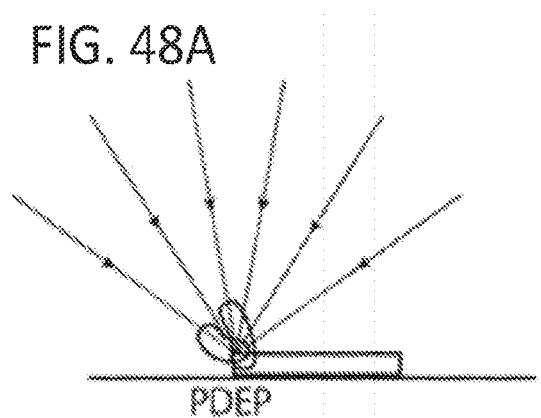
FIGS. 48A-F show a technique for measuring a bacterial response to an applied electric field when motion is restricted in two dimensions in accordance with some embodiments.
Figure 48B:
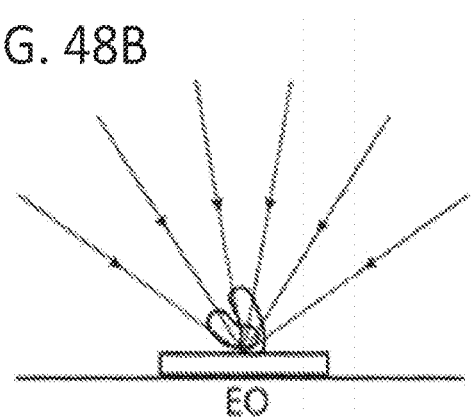

FIG. 48A shows a first capture mechanism due to positive dielectrophoresis (PDEP) which captures analyte particles on the edge of the electrode. In this capture mechanism, analyte particles are typically aligned in the horizontal plane, FIG. 48B shows a second capture mechanism due to electroosmosis (EO), which captures analyte particles in the center of the EO trap.

Figure 48C:
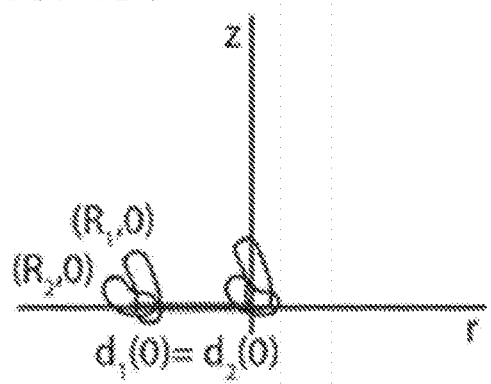

FIG. 48C shows that by switching the properties of the electric field to move analyte particles between the traps causes analyte particles to move between the two trapping centers. In some embodiments, the movement between the traps is linear, rotational, circular, or has another complex trajectory of motion within the trap. In accordance with some embodiments, the trapping centers are both PDEP traps, EO/PDEP traps, PDEP/EO traps, or other types of AC kinetic traps.

Figure 48D:
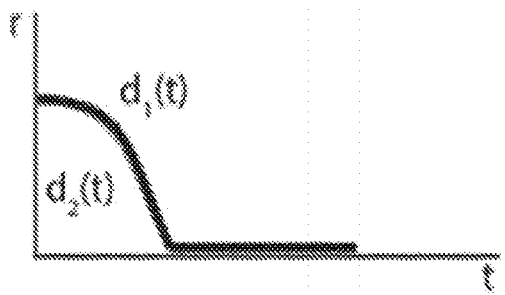

FIG. 48D shows that the measured 2D trajectory and travel times are the same for analyte particles of the same type.

Figure 48E:
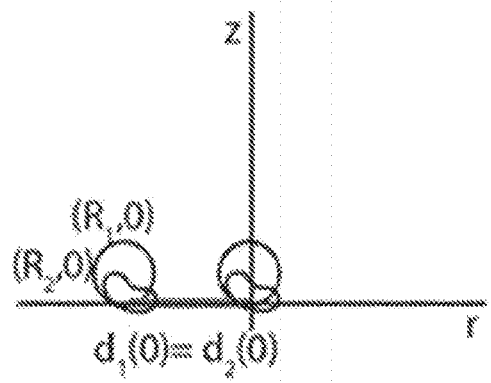
Figure 48F:
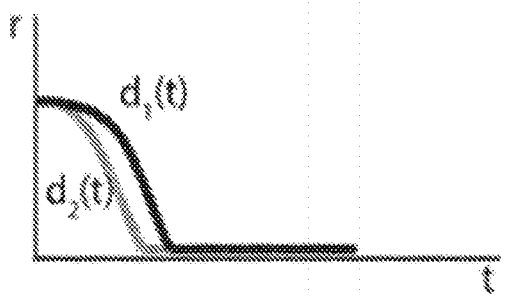
Figure 59:
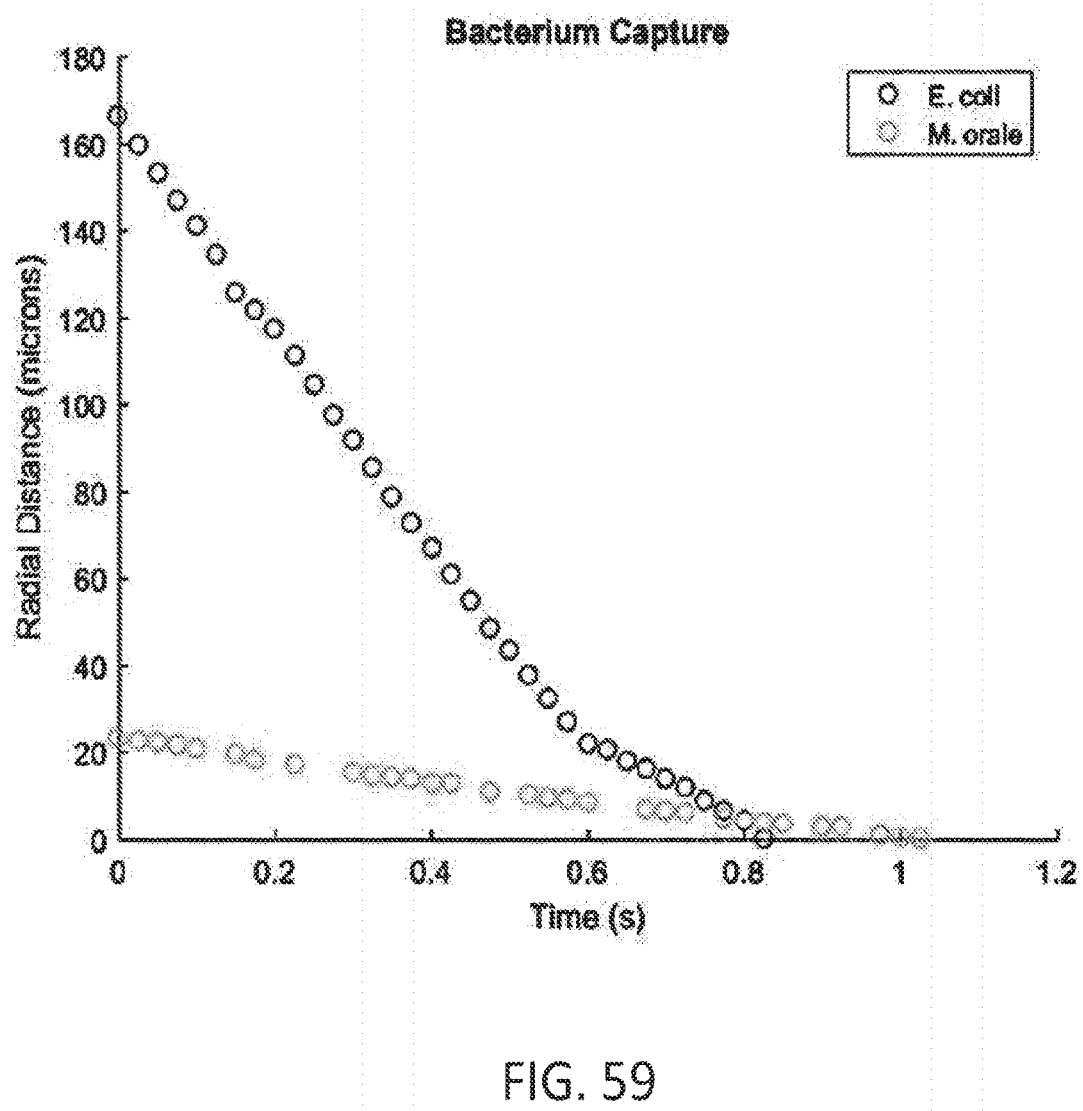
FIG. 59 shows trajectories of E. coli bacterium and M. orale bacterium measured and captured with the motion confinement between two traps in accordance with some embodiments.

FIG. 48E shows that different analyte particles are trapped in the same initial and final positions. FIG. 48F shows that travel times for the different analyte particles vary. FIG. 59 shows trajectories for two bacterial types, *E. coli* and *M. orali* measured while bacterial motion was confined between two traps. As shown, trajectories may vary for different bacterium types.

Confining the possible particle motion and trajectory to the controlled motion and displacement between two traps, allows to evaluate the observed dynamics of motion $d(t)$ and allows to determine from the observed trajectories differences in analyte particles based on their shape, morphology, and chemical composition.

Evaluating and analyzing the motion trajectory of an analyte confined between two traps allows to identify the analyte based on the signal shape, the trajectory, the time of motion, or the time of flight.

Universal Bacterial Capture

Some embodiments are directed to a device configured to capture a wide range of bacterial and other contaminants (e.g., viruses). In one example, the contaminant may be bacteria or viruses, and the sample may be a protein and/or cell matrix such as blood, urine, cell culture, protein suspension, beverage, recreational water, water, or purified water.

FIG. 49A shows different sections of a device from a top view in accordance with some embodiments. FIGS. 49B-J show cross section views of the device of FIG. 49A along the fluid flow direction. Referring to FIG. 49A, for continuous flow operation, inlets 1 and 2 may be coupled to a line, e.g., a manufacturing line, a tank, or an IV (intravenous) line. The sample may be pulled or pushed through inlet 2 into a mixing chamber 4, and the sample may be mixed with a reference solution to achieve parameters within a desired operating range. For example, a solution having low conductivity may be created. The reference solution may be introduced through inlet 1 to enable mixing in mixing chamber 4.

An unprocessed reference solution may include contaminants. FIG. 49B shows bacteria in a reference solution in a microfluidic channel. To avoid introducing contamination through the reference solution, chamber 3, which is option in some embodiments, is configured to filter the reference solution introduced via inlet 1 by removing bacteria or other contaminants. FIG. 49C shows that an electric field applied to chamber 3 may be set in such a way to capture contaminants on the electrode system or in the interelectrode space. Accordingly, the reference solution introduced via inlet 1 and passing through chamber 3 is purified from contaminants in the reference solution as shown in FIG. 49D.

The reference solution, whether purified or not, and the sample mix in chamber 4, as discussed above. FIG. 49E shows that the sample introduced via inlet 2 may include microscopic components different than the contaminant included in the reference solution.

In some embodiments, chamber 4 may include a conductivity sensor or other sensor to monitor solution conductivity and/or other electric or chemical parameters. The sensor may be configured to provide feedback to the rate of mixing in chamber 4 to adjust an appropriate operating parameter to bring the solution to a desired operational range. In some embodiments, the sensor is integrated with electrodes.

Upon entering chamber 5, the sample and reference solution mixture is subjected to an AC electric field generated by applying a voltage to a system of electrodes designed in accordance with one or more of the techniques described herein. The characteristics of the applied electric field are chosen in such a way to capture contaminants on the electrode system and to allow for microscopic components of the non-contaminants to flow by and be removed by the incoming flow. For example, the frequency of the electric field may be tuned in such a way to provide a strong AC kinetic force dominating flow forces on one component (e.g., the contaminant or analyte), and small or no force of opposite sign dominated by flow forces on another component in the solution. Flow may be adjusted as one of the operating parameters of the device to achieve separation of the components of the solution in accordance with some embodiments.

The sample having adjusted parameters then flows over an electrode array which may be located on one side or on opposing sides of one or more microfluidics channels. As shown in FIG. 49F, bacteria and other contaminants may be captured on the electrode system with AC kinetic forces due to the applied AC electric field. FIG. 49G illustrates introduction of a rinse, buffer solution, or reference solution to chamber 5 to wash off non-contaminants, while the contaminants or analytes remain captured on the electrode system.

In some embodiments, a stain is introduced into the microfluidic channel to stain contaminants or analytes such as bacteria to facilitate visual inspection. It may be determined, for example, if there is a presence or absence of contaminants or analytes in the sample, and additionally the contaminants or analytes may be quantified, e.g., optically.

Switching a voltage between traps, e.g., between an EO (electroosmosis trap) and a PDEP (positive dielectrophoresis trap) using the techniques described above, causes bacteria to move between two different positions. For example, as shown in FIG. 49H, a characteristic (e.g., voltage) of the applied AC electric field may be switched between two capture sites. The contaminant and or analytes may be detected by the motion resulting from the switching of the position of the contaminant or analytes between traps as a result of the switching as shown in FIG. 49I. This technique may eliminate the need for staining to be able to use optical detection. In some embodiments, a stain or other chemical agent is introduced inside of a microfluidic channel to modify a charge of bacteria or other analytes for subsequent electronic detection. FIG. 49J shows that the captured contaminant and/or analyte may be released after separation for further analysis. For example, FIG. 46F shows *E. coli* and *Enterococcus* bacteria being simultaneously captured with dielectrophoresis on electrode edges at 1 MHz.

Sample Sorting

Some embodiments are directed to selective capture from complex matrix (e.g., a bacterial species from fecal sample, indicator bacteria from drinking or river or cooling water, bacteria in sepsis, specific bacteria from blood (Lyme disease), etc.). The technique described in the previous section allows separation and capture of a broad range of contaminants and particles having a size similar to that of the contaminant. Some embodiments include an additional sorting technique that uses a series of traps with varied electric field characteristics (e.g., frequency or voltage) simultaneously or sequentially to achieve separation of an analyte in multiple steps, each achieving more selective separation. In some embodiments, chamber 5 in FIG. 49A is expanded into a series of electrode systems with optional additional mixing chambers to achieve sequential parameter (e.g., conductivity adjustment) between traps in each system.

Figure 50A:
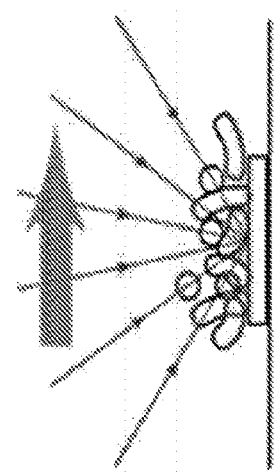
FIGS. 50A-F illustrate schematic views of a multi-stage separation in addition to the process illustrated in FIGS. 49A-J in accordance with some embodiments.
Figure 50D:
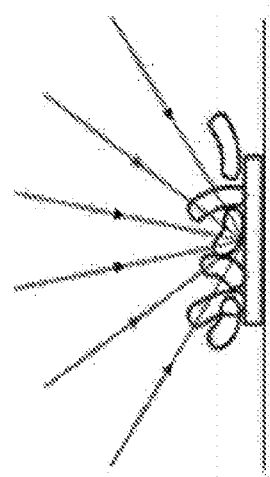
Figure 50B:
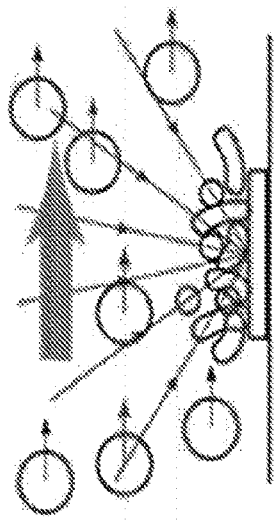
Figure 50E:
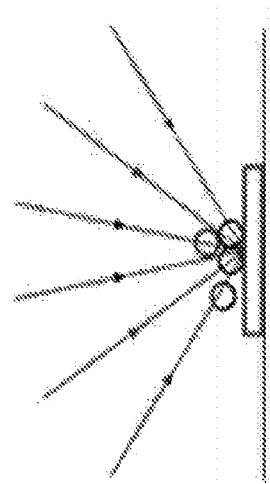
Figure 50C:
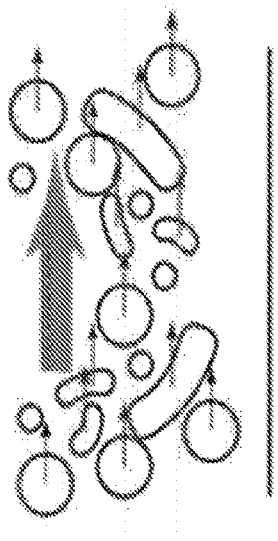
Figure 50F:
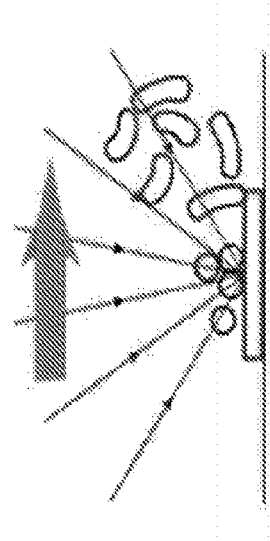

As shown in FIG. 50A, the solution introduced into chamber 5 may contain a mix of microscopic components. FIG. 50B shows a first separation and sample sorting step, in which a first electrode system having a set of operating parameters S1 is used to sort components of a certain size or having certain dielectric properties. As shown in FIG. 50C, a sequential system of electrodes may be configured to act as traps having a set of operating parameters S1 to purify the analyte of interest and some microscopic components which also respond and or are captured using the set of operating parameters S1. Another set of operating parameters S2 applied to the subsequent system of electrodes may be used to separate the previously-captured analyte and microscopic components into separate groups, as shown in FIG. 50D. FIGS. 50E and 50F show that one or multiple groups may remain captured as a result of applying an electric field having the second set of operating parameters S2. Following capture, one or more of the captured analytes or analyte groups may be released for further analysis. For example, FIG. 46D shows *Enterococcus* bacteria remaining captured, while *E. coli* detach from the electrodes at 80 MHz.

Filtration of Complex Matrices

Some embodiments are directed to a device configured to purify a substance from contaminants. For example, a set of filters described in accordance with FIGS. 49 and 50 may be configured in such a way to capture broad contamination and separate it from a sample for purification. To improve the accuracy of purification of controlled samples, which contain a small set of target microscopic components (e.g., a controlled cell or protein matrix, e.g., cultured in drug production) the set of operating parameters S1, S2 may be set in such a way so as not to capture the target microscopic components, but to capture the contaminant, which is every particle not having a desired characteristic. In such a technique, rather than capturing the analyte for further analysis, one or more contaminants are captured, for example, by performing a reverse operation of the sample sorting device described above. In some embodiments, the excess reference solution may be removed by e.g., centrifugation or another suitable technique.

Portable Device with Optical Readout

Some embodiments are directed to a portable device with an optical readout. In such embodiments, the device may include microchannels made out of an optically magnifying material with a higher refractive index than glass to facilitate viewing of bacteria moving through the device without the need to a highly calibrated microscope, thereby allowing for replacement of the microscope with a regular digital camera for portable and field applications.

High Volume Throughput Device

Some embodiments are directed to a high-volume throughput device. In such embodiments, the device may include repeated or elongated electrode pattern to extend the capture zone of the device for higher capture efficiency and higher volume throughput with, e.g., a larger height of the microfluidic chamber or a faster flow rate. FIGS. 52A and 52B show cross sections of a device where the direction of flow is from left to right. In FIG. 52A, particle 1 moves with velocity v1. If the length of the depletion zone is L, then particle 1 interacts with the electrode system during time tf=L/v. If the time tc needed for particle 1 to be captured by the electrode system under no flow conditions is longer than tf>tc, then particle 1 flows over the electrode system without being captured. The trajectory of particle 1 is affected by the electric field generated over the electrode system. The particle is attracted to the electrode system, however it moves away due to fluid flow before it reaches the electrode. By contrast, the initial position of particle 2 is closer to the electrode system, therefore tf<tc for particle 2 and the particle is captured. FIG. 52B shows an elongated structure with N=2 capture electrodes. In this scenario, the amount of time particle 3 is exposed to the electric field of the electrode system is N·tc. If N·tc>tf then even bacterial that are far away from the electrode system and/or fast moving bacteria may be captured.

Use of Edge Connectors

Figure 51C:
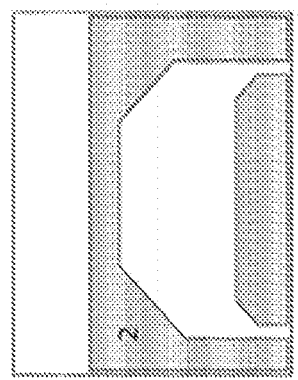
FIGS. 51A-F show schematic portion of a device with multiple configurations of microfluidic chambers and an electric contact to interface with an edge connector and external electronic device in accordance with some embodiments.
Figure 51F:
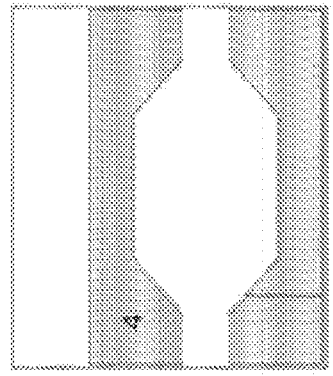
Figure 51B:
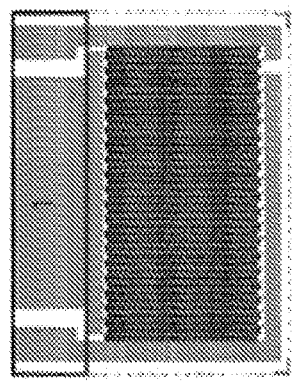
Figure 51E:
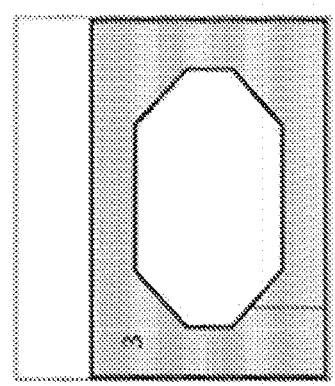
Figure 51A:
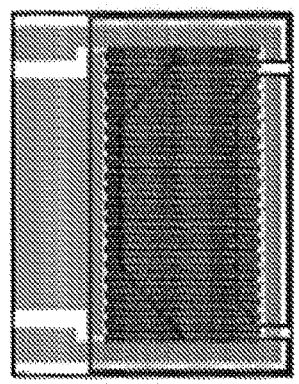
Figure 51D:
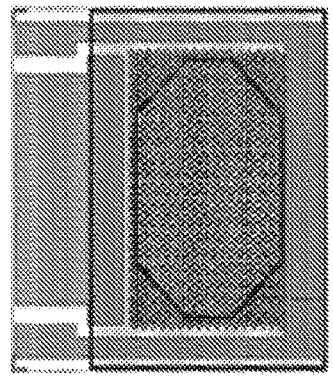

Some embodiments are directed to the use of edge connectors to provide an interface to an electronic/microfluidic device. FIG. 51A shows a schematic of a device with a contact fitting an edge connector in accordance with some embodiments. FIG. 51B shows a schematic of the metal pattern of the device in FIG. 51A. The metal contact that fits within the edge connector is indicated with the label 1. FIG. 51C shows a schematic of the microfluidic pattern of the device in FIG. 51A. The microfluidic structure is indicated with the label 2. The microfluidic device has side inlets located on one side of the device. FIG. 51D shows a schematic of a device with a contact fitting an edge connector and a different microfluidic pattern. FIG. 51E shows a schematic of the microfluidic pattern of the device shown in FIG. 51D. The microfluidic pattern has inlets from the top. FIG. 51F shows a schematic of the microfluidic pattern of the device shown in FIG. 51D. The microfluidic pattern has inlets from the side on opposing device walls.

Figure 57A:
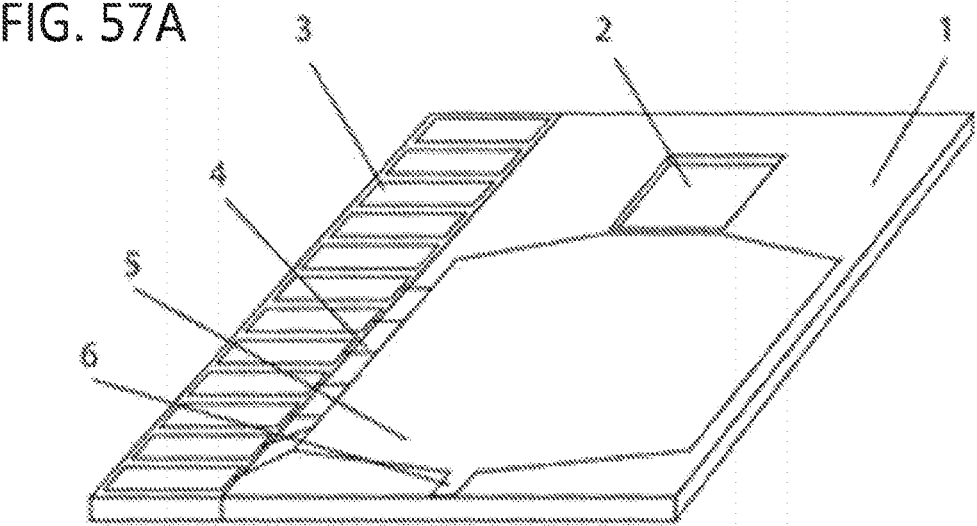
FIGS. 57A-D shows schematics of an integrated device for analyte capture and/or separation and detection in accordance with some embodiments.
Figure 57B:
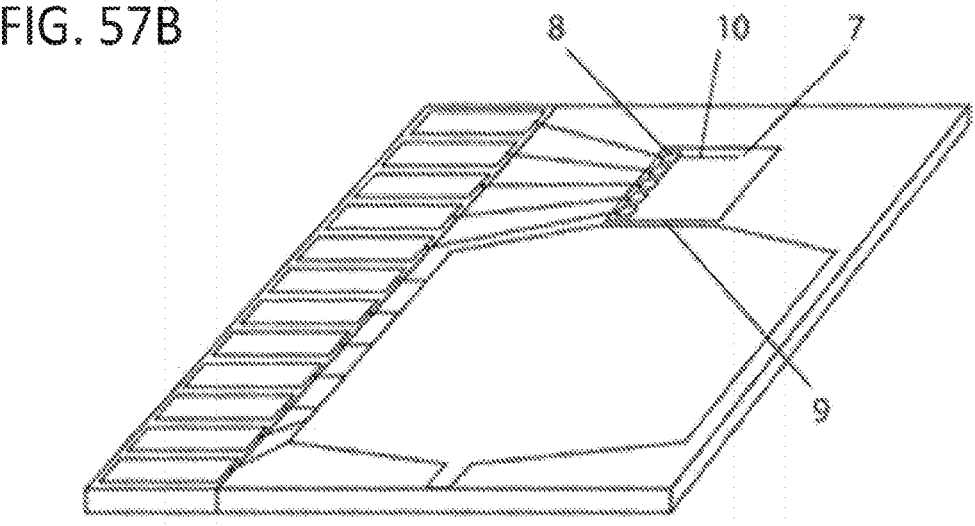
Figure 57C:
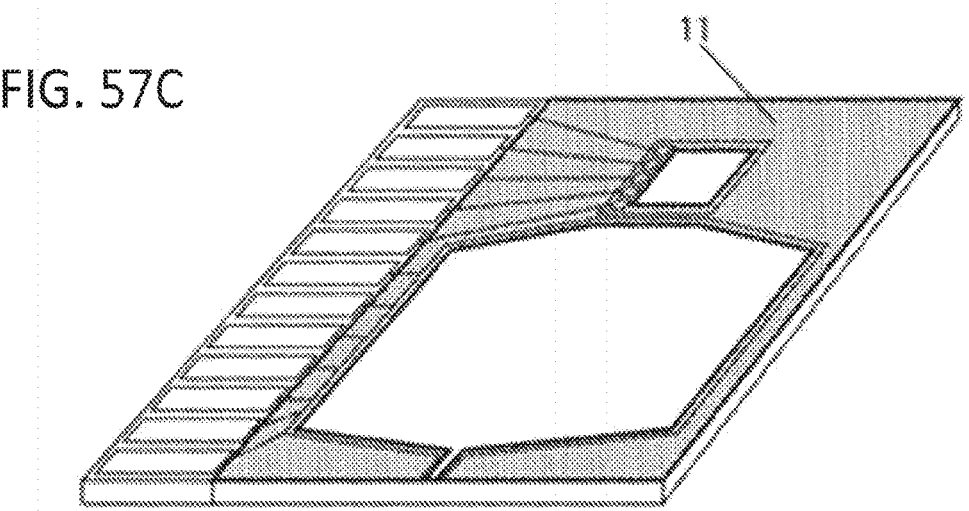
Figure 57D:
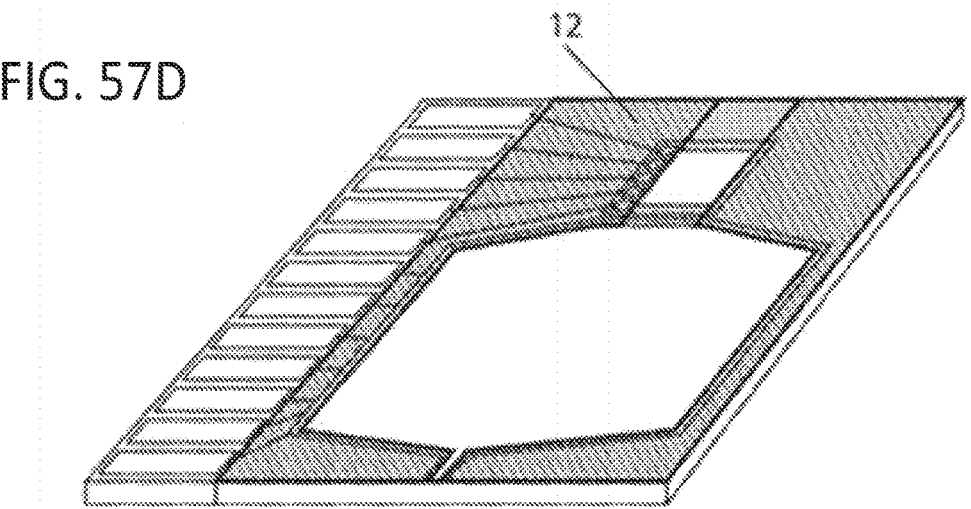

Some embodiments are directed to using an assembly of layers for integration of discrete components, such as two devices, as shown in FIGS. 57A-D. FIG. 57A shows a substrate being prepared for assembly. The substrate includes a device bottom part 1, that may be made, for example, of glass, silicon, or plastic; an opening 2 for a sensor; a contact pad 3; a lead 4 to a contact pad; an area 5 with electrode structures; an inlet 6; a sensor chip 7; a contact pad 8 on the sensor chip 7; a space 9 between the sensor die and the substrate where a fluid may be placed; an electrode 10 configured to act as a virtual valve preventing analyte from passing to waste; a sheet layer 11 (e.g., a dry film) patterned to connect a discrete component, the sensor, and the substrate; and a second sheet layer 12 patterned to define a flow path and microfluidic chamber. FIG. 57B shows a discrete component being placed on the substrate. FIG. 57C shows a sheet layer 11 (e.g., a dry film) with a defined pattern being placed to connect the substrate and the discrete component and to prevent sample leakage. FIG. 57D shows a second sheet layer 12 being placed to define the walls of a microfluidic chamber.

Below is an example of a fabrication process for fabricating the device shown in FIGS. 57A-D:
Wafer patterning for DEP filter
Cut openings for sensor
Place sensor in opening
Dry film or adhesive patterning on top of the wafer (to cover adjacent gaps)
Embedding & dicing
Elongated path for faster flow and higher volume throughput and efficient capture
Transfer to sensor at slow flow
High surface density coverage for high efficiency Various aspects of the apparatus and techniques described herein may be used alone, in combination, or in a variety of arrangements not specifically discussed in the embodiments described in the foregoing description and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The invention claimed is:

1. A spectrometer configured to determine an identity of analyte particles in solution, the spectrometer comprising:
    a circular-shaped or partially-center-symmetric electrode configured to be placed in an AC electric field;
    a controller configured to switch at least one property of the AC electric field from a first condition to a second condition, wherein the at least one property comprises an amplitude of the AC electric field, wherein when the AC electric field is in the first condition, the analyte particles are trapped in a first AC kinetic trap on the electrode and wherein when the AC electric field is in the second condition, the analyte particles are trapped in a second AC kinetic trap on the electrode;
    a detector configured to determine at least one motion characteristic of the analyte particles from the first AC kinetic trap to the second AC kinetic trap in response to switching the at least one property of the AC electric field; and
    at least one processor programmed to:
        compare the determined at least one motion characteristic to each of a plurality of stored analyte particle motion characteristics; and
        determine the identity of the analyte particles based, at least, in part on the comparisons.

2. The spectrometer of claim 1, wherein the at least one property further comprises a frequency of the AC electric field.

3. The spectrometer of claim 1, wherein the first AC kinetic trap is an electroosmosis trap and the second AC kinetic trap is a dielectrophoresis trap.

4. The spectrometer of claim 3, wherein the electroosmosis trap is located at a center of the electrode and the dielectrophoresis trap is located at an edge of the electrode.

5. The spectrometer of claim 1, wherein the detector is an optical detector.

6. The spectrometer of claim 1, further comprising:
a filtering stage configured to filter the analyte particles from other components in the solution to produce a filtered solution, and
wherein the electrode is arranged to trap the analyte particles in the filtered solution.

7. The spectrometer of claim 6, wherein the other components in the solution are blood cells.

8. The spectrometer of claim 1, wherein the analyte particles are viruses or bacteria.

9. The spectrometer of claim 1, wherein the electrode is configured to restrict motion of the analyte particles along the surface of the electrode.

10. The spectrometer of claim 1, wherein the at least one motion characteristic is a motion trajectory.

11. The spectrometer of claim 1, wherein the at least one motion characteristic is an amount of time that the analyte particles take to travel from the first AC kinetic trap to the second AC kinetic trap in response to the switching of the at least one property of the AC electric field.

12. A method of determining an identity of analyte particles in a solution, the method comprising:
placing a circular-shaped or partially-center symmetric electrode in an AC electric field;
switching at least one property of the AC electric field from a first condition to a second condition, wherein switching the at least one property comprises switching an amplitude of the AC electric field, wherein when the AC electric field is in the first condition, the analyte particles are trapped in a first AC kinetic trap on the electrode and wherein when the AC electric field is in the second condition, the analyte particles are trapped in a second AC kinetic trap on the electrode;
determining at least one motion characteristic of the analyte particles from the first AC kinetic trap to the second AC kinetic trap in response to switching the at least one property of the AC electric field;
comparing the determined at least one motion characteristic to each of a plurality of stored analyte particle motion characteristics; and
determining the identity of the analyte particles based, at least in part, on the comparisons.

13. The method of claim 12, wherein switching the at least one property further comprises switching a frequency of the AC electric field.

14. The method of claim 12, wherein determining at least one motion characteristic of the analyte particles comprises determining the at least one motion characteristic using an optical detector.

15. The method of claim 12, further comprising:
filtering the analyte particles from other components in the solution to produce a filtered solution, and
wherein determining at least one motion characteristic of the analyte particles from the first AC kinetic trap to the second AC kinetic trap in response to switching the at least one property of the AC electric field comprises determining the at least one motion characteristic of the analyte particles in the filtered solution.

16. The method of claim 12, wherein determining the at least one motion characteristic comprises determining a motion trajectory.

17. The method of claim 12, wherein determining the at least one motion characteristic comprises determining an amount of time that the analyte particles take to travel from the first AC kinetic trap to the second AC kinetic trap in response to the switching of the at least one property of the AC electric field.

18. A spectrometer configured to determine an identity of analyte particles in solution, the spectrometer comprising:
a circular-shaped or partially-center-symmetric electrode configured to be placed in an AC electric field;
a controller configured to switch at least one property of the AC electric field from a first condition to a second condition, wherein when the AC electric field is in the first condition, the analyte particles are trapped in a first AC kinetic trap on the electrode and wherein when the AC electric field is in the second condition, the analyte particles are trapped in a second AC kinetic trap on the electrode;
a detector configured to determine at least one motion characteristic of the analyte particles from the first AC kinetic trap to the second AC kinetic trap in response to switching the at least one property of the AC electric field; and
at least one processor programmed to:
compare the determined at least one motion characteristic to each of a plurality of stored analyte particle motion characteristics, wherein the at least one motion characteristic is an amount of time that the analyte particles take to travel from the first AC kinetic trap to the second AC kinetic trap in response to the switching of the at least one property of the AC electric field; and
determine the identity of the analyte particles based, at least, in part on the comparisons.

19. A method of determining an identity of analyte particles in a solution, the method comprising:
placing a circular-shaped or partially-center symmetric electrode in an AC electric field;
switching at least one property of the AC electric field from a first condition to a second condition, wherein when the AC electric field is in the first condition, the analyte particles are trapped in a first AC kinetic trap on the electrode and wherein when the AC electric field is in the second condition, the analyte particles are trapped in a second AC kinetic trap on the electrode;
determining at least one motion characteristic of the analyte particles from the first AC kinetic trap to the second AC kinetic trap in response to switching the at least one property of the AC electric field, wherein determining the at least one motion characteristic comprises determining an amount of time that the analyte particles take to travel from the first AC kinetic trap to the second AC kinetic trap in response to the switching of the at least one property of the AC electric field;
comparing the determined at least one motion characteristic to each of a plurality of stored analyte particle motion characteristics; and
determining the identity of the analyte particles based, at least in part, on the comparisons.

* * * * *